US012741968B2

(12) United States Patent
Higuchi et al.

(10) Patent No.: US 12,741,968 B2
(45) **Date of Patent: *Sep. 22, 2026**

(54) THERAPEUTIC AGENTS TARGETING GPR35

(71) Applicant: PROMETHEUS BIOSCIENCES, INC., San Diego, CA (US)

(72) Inventors: Robert Higuchi, San Diego, CA (US); Michael Bishop, San Diego, CA (US)

(73) Assignee: Prometheus Biosciences, Inc., San Diego, CA (US)

(*) Notice: Subject to any disclaimer, the term of this patent is extended or adjusted under 35 U.S.C. 154(b) by 646 days.

This patent is subject to a terminal disclaimer.

(21) Appl. No.: 18/157,686

(22) Filed: Jan. 20, 2023

(65) Prior Publication Data

US 2023/0151017 A1 May 18, 2023

Related U.S. Application Data

(63) Continuation of application No. PCT/US2021/042813, filed on Jul. 22, 2021.

(60) Provisional application No. 63/055,621, filed on Jul. 23, 2020.

(51) Int. Cl.
*C07D 487/04* (2006.01)
*A61P 1/04* (2006.01)

(52) U.S. Cl.
CPC .............. *C07D 487/04* (2013.01); *A61P 1/04* (2018.01)

(58) Field of Classification Search
None
See application file for complete search history.

(56) References Cited

U.S. PATENT DOCUMENTS

| | | | | |
|---|---|---|---|---|
| 3,933,822 | A | 1/1976 | Broughton et al. | |
| 3,987,160 | A | 10/1976 | Broughton et al. | |
| 4,052,390 | A | 10/1977 | Broughton et al. | |
| 4,167,568 | A | 9/1979 | Knowles et al. | |
| 4,923,874 | A * | 5/1990 | McMahon | A61K 31/505 544/254 |
| 5,474,796 | A | 12/1995 | Brennan | |
| 8,819,989 | B2 | 9/2014 | Paternoster et al. | |
| 9,353,115 | B2 | 5/2016 | Lipford et al. | |
| 10,519,373 | B2 | 12/2019 | Spittle et al. | |
| 11,053,251 | B2 * | 7/2021 | Higuchi | C07D 487/04 |
| 11,773,101 | B2 * | 10/2023 | Higuchi | C07D 487/04 514/261.1 |
| 2015/0273088 | A1 | 10/2015 | Piwnica-Worms et al. | |
| 2018/0305459 | A1 | 10/2018 | McGovern et al. | |
| 2020/0362025 | A1 | 11/2020 | Kruidenier et al. | |
| 2021/0395827 | A1 | 12/2021 | Bilsborough et al. | |
| 2022/0056106 | A1 | 2/2022 | Bilsborough et al. | |
| 2022/0290241 | A1 | 9/2022 | McGovern et al. | |

FOREIGN PATENT DOCUMENTS

| | | | |
|---|---|---|---|
| WO | WO-2004035584 | A1 | 4/2004 |
| WO | WO-2015021080 | A2 | 2/2015 |
| WO | WO-2019210203 | A1 | 10/2019 |
| WO | WO-2020154492 | A1 | 7/2020 |
| WO | WO-2022020617 | A1 | 1/2022 |
| WO | WO-2022103961 | A1 | 5/2022 |
| WO | WO-2022140283 | A1 | 6/2022 |

OTHER PUBLICATIONS

Broughton et al., Antiallergic Activity of 2-Phenyl-8-azapurin-6-ones, 1975, J. Med. Chem., 18, 1117-1122. (Year: 1975).*

6-(4-Chlorophenyl)-5-(4-pyrazin-2-ylphenyl)-3-(3-sulfanylphenyl)triazolo[4,5-d]pyrimidin-7-one. PubCham-CID-70962124. 7 pages (2013).

Berge et al. Pharmaceutical Salts. Journal of Pharmaceutical Sciences 66(1):1-19 (Jan. 1977).

Broughton et al.: Antiallergic Activity of 2-Pehnyl-8-azapurin-6-ones.J. Med. Chem. 18:1117-1122 (1975).

Jenkins et al.: Antagonists of GPR35 display high species ortholog selectivity and varying modes of action. J Pharmacol Exp Ther. 343(3):683-695 (2012).

MacKenzie et al.: "GPR35 as a novel therapeutic target" Review Article Nov. 9, 2011, vol. 2, Article 68 (pp. 1-10).

PCT/US2020/014777 International Preliminary Report on Patentability dated Aug. 5, 2021.

PCT/US2020/014777 International Search Report and Written Opinion dated Apr. 16, 2020.

PCT/US2021/042813 International Preliminary Report on Patentability dated Feb. 2, 2023.

PCT/US2021/042813 International Search Report and Written Opinion dated Nov. 15, 2021.

(Continued)

*Primary Examiner* — Jeffrey H Murray
*Assistant Examiner* — Luke Alan Boralsky
(74) *Attorney, Agent, or Firm* — Daniel Woods; John C. Todaro

(57) ABSTRACT

Described herein are compounds of Formula I

I

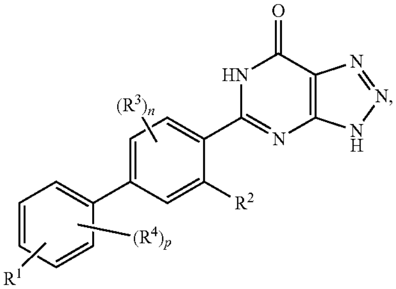

or a pharmaceutically acceptable salt thereof. The compounds of Formula I act as GPR35 modulators and can be useful in preventing, treating or acting as a remedial agent for GPR35 related diseases, disorders or conditions.

20 Claims, No Drawings

(56) References Cited

OTHER PUBLICATIONS

Prometheus Biosciences, Inc. Form S-1 Registration Statement as filed with the Securities and Exchange Commission on Feb. 19, 2021 (246 pages).
PubChem CID 137173496 (2019).
U.S. Appl. No. 16/751,092 Office Action dated Dec. 7, 2020.
U.S. Appl. No. 17/323,979 Restriction Requirement dated Jan. 20, 2023.

* cited by examiner

THERAPEUTIC AGENTS TARGETING GPR35

CROSS-REFERENCE

This application is a continuaton application of International Application No. PCT/US2021/042813 filed Jul. 22, 2021, which claims the benefit of U.S. Provisional Patent Application Ser. No. 63/055,621 filed Jul. 23, 2020, which is incorporated herein by reference in its entirety.

BACKGROUND OF THE INVENTION

Millions of people are affected by inflammatory disease or conditions. A prominent inflammatory disease is inflammatory bowel disease (IBD). IBD has two common forms, Crohn's disease (CD) and ulcerative colitis (UC), which are chronic, relapsing inflammatory disorders of the gastrointestinal tract. Each of these forms has various sub-conditions that are present in sub-populations of CD and UC patients. Some CD and UC patients experience a rapid onset of sub-conditions, while others experience a relative delay.

Few treatment options are available to patients that suffer from IBD. Further, selecting a therapy that is appropriate for any individual patient at any given stage of their disease is complicated by the unpredictability of each individual's prognosis. Current therapeutic regimens include one or more of anti-inflammatory medication (e.g., corticosteroids) and immunomodulatory therapy (e.g., anti-TNF therapy). However, nearly half of all patients treated with an anti-TNF therapy do not respond to the induction of the therapy, or experience a loss of response to the treatment after a period of time, during which, disease severity has progressed significantly. Therefore, there remains a significant need for targeted and effective treatment options that respond to the underlying immunopathogenesis of IBD.

SUMMARY OF THE INVENTION

In one aspect, provided herein are compounds of Formula (I):

Formula (I)

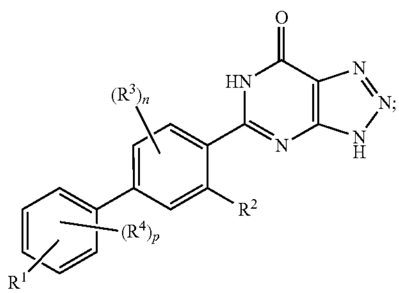

wherein:

$R^1$ is —$C_{1-6}$alkyl-C(O)N($R^{10}$)$_2$, —$C_{1-6}$alkyl-C(O)N(H)(OH), —$C_{1-6}$alkyl-C(O)N(H)($OCH_3$), —$C_{1-6}$alkyl-C(O)N(H)S(O)$_2$N($R^{10}$)$_2$, —O—$C_{1-6}$alkyl-C(O)N($R^{10}$)$_2$, —O—$C_{1-6}$alkyl-C(O)N(H)(OH), —O—$C_{1-6}$alkyl-C(O)N(H)($OCH_3$), —O—$C_{1-6}$alkyl-C(O)N(H)S(O)$_2$N($R^{10}$)$_2$, —C(H)═$R^5$, —$C_{1-6}$alkyl-$R^5$, or —$C_{1-6}$alkyl-$C_{1-9}$heteroaryl, wherein —$C_{1-6}$alkyl-$C_{1-9}$heteroaryl is optionally substituted with one, two, or three groups independently selected from halogen, $C_{1-6}$alkyl, $C_{1-6}$haloalkyl, and —C(O)O$R^{10}$;

$R^2$ is H, —OH, —N($R^{10}$)$_2$, —NHS(O)$_2R^9$, —S(O)$_2$N($R^{10}$)$_2$, —C(O)N($R^{10}$)$_2$, —OC(O)N($R^{10}$)$_2$, —O—$C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl;

each $R^3$ is independently selected from halogen, —CN, —OH, —O$R^9$, —S$R^9$, —N($R^{10}$)$_2$, —$NO_2$, —S(O)$R^9$, —S(O)$_2R^9$, —NHS(O)$_2R^9$, —S(O)$_2$N($R^{10}$)$_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each $R^4$ is independently selected from halogen, —CN, —OH, —O$R^9$, —S$R^9$, —N($R^{10}$)$_2$, —S(O)$R^9$, —S(O)$_2R^9$, —NHS(O)$_2R^9$, —S(O)$_2$N($R^{10}$)$_2$, —C(O)NHS(O)$_2$N($R^{10}$)$_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-$R^9$, —$C_{1-6}$alkyl-OH, —$C_{1-6}$alkyl-O$R^9$, —$C_{1-6}$alkyl-N($R^{10}$)$_2$, —$C_{1-6}$alkyl-C(O)O$R^{10}$, $C_{2-6}$alkenyl, —$C_{2-6}$alkenyl-C(O)O$R^{10}$, $C_{2-6}$alkynyl, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, and $C_{1-9}$heteroaryl; wherein $C_{3-8}$cycloalkyl, —$C_{1-6}$alkyl-$C_{3-8}$cycloalkyl, phenyl, —$C_{1-6}$alkyl-phenyl, and $C_{1-9}$heteroaryl are optionally substituted with one, two, or three groups independently selected from halogen, —C(O)O$R^{10}$, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl and —$C_{1-6}$alkyl-$C_{2-9}$heterocycloalkyl are optionally substituted with one, two, or three groups independently selected from halogen, —C(O)O$R^{10}$, $C_{1-6}$alkyl, $C_{1-6}$haloalkyl, and oxo;

$R^5$ is $C_{2-9}$heterocycloalkyl optionally substituted with one, two, or three groups independently selected from halogen, $C_{1-6}$alkyl, $C_{1-6}$haloalkyl, —C(O)O$R^{10}$, and oxo;

each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —O$R^{11}$, —N($R^{11}$)$_2$, $C_{1-6}$alkyl, $C_{3-8}$cycloalkyl, —N($R^{11}$)C(O)$R^{12}$, —C(O)$R^{12}$, and —C(O)O$R^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N($R^{11}$)$_2$, and —C(O)O$R^{12}$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each $R^{11}$ is independently selected from H and $C_{1-6}$alkyl;

each $R^{12}$ is independently selected from H and $C_{1-6}$alkyl;

n is 0, 1, 2, or 3; and p is 0, 1, 2, 3, or 4;

or a pharmaceutically acceptable salt or solvate thereof.

In some embodiments is a compound of Formula (I), or a pharmaceutically acceptable salt or solvate thereof, wherein $R^1$ is $—C_{1-6}$alkyl-$R^5$. In some embodiments is a compound of Formula (I), or a pharmaceutically acceptable salt or solvate thereof, wherein $R^1$ is $—C(H)═R^5$. In some embodiments is a compound of Formula (I), or a pharmaceutically acceptable salt or solvate thereof, wherein $R^5$ is $C_{2-9}$heterocycloalkyl substituted with one, two, or three groups independently selected from $C_{1-6}$alkyl and oxo. In some embodiments is a compound of Formula (I), or a pharmaceutically acceptable salt or solvate thereof, wherein $R^5$ is $C_{2-9}$heterocycloalkyl substituted with one, two, or three groups independently selected from $C_{1-6}$alkyl, $C_{1-6}$haloalkyl, and oxo. In some embodiments is a compound of Formula (I), or a pharmaceutically acceptable salt or solvate thereof, wherein $R^1$ is

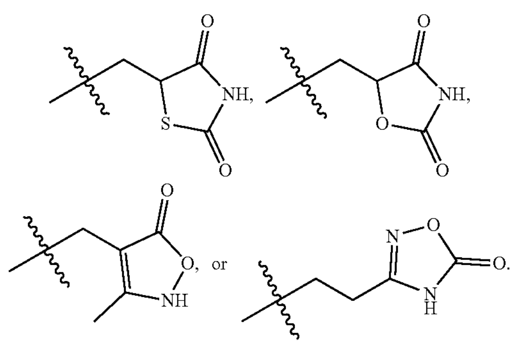

In some embodiments is a compound of Formula (I), or a pharmaceutically acceptable salt or solvate thereof, wherein $R^1$ is

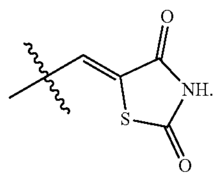

In some embodiments is a compound of Formula (I), or a pharmaceutically acceptable salt or solvate thereof, wherein $R^1$ is $—C_{1-6}$alkyl-$C(O)N(H)S(O)_2N(R^{10})_2$. In some embodiments is a compound of Formula (I), or a pharmaceutically acceptable salt or solvate thereof, wherein $R^1$ is $—CH_2CH_2—C(O)N(H)S(O)_2N(CH_3)_2$. In some embodiments is a compound of Formula (I), or a pharmaceutically acceptable salt or solvate thereof, wherein $R^1$ is $—C_{1-6}$alkyl-$C_{1-9}$heteroaryl optionally substituted with one, two, or three groups independently selected from halogen, $C_{1-6}$alkyl, $C_{1-6}$haloalkyl, and $—C(O)OR^{10}$. In some embodiments is a compound of Formula (I), or a pharmaceutically acceptable salt or solvate thereof, wherein each $R^4$ is independently selected from halogen, —OH, $—OR^9$, $—N(R^{10})_2$, $—C(O)OR^{10}$, $—C(O)N(R^{10})_2$, $C_{1-6}$alkyl, $—C_{1-6}$alkyl-OH, $—C_{1-6}$alkyl-$OR^9$, $—C_{1-6}$alkyl-$N(R^{10})_2$, $—C_{1-6}$alkyl-$C(O)OR^{10}$, and $C_{1-9}$heteroaryl. In some embodiments is a compound of Formula (I), or a pharmaceutically acceptable salt or solvate thereof, wherein each $R^4$ is independently selected from halogen, —OH, $—OR^9$, $C_{1-6}$alkyl, and $—C_{1-6}$alkyl-OH. In some embodiments is a compound of Formula (I), or a pharmaceutically acceptable salt or solvate thereof, wherein p is 0, 1, or 2. In some embodiments is a compound of Formula (I), or a pharmaceutically acceptable salt or solvate thereof, wherein p is 1. In some embodiments is a compound of Formula (I), or a pharmaceutically acceptable salt or solvate thereof, wherein p is 0. In some embodiments is a compound of Formula (I), or a pharmaceutically acceptable salt or solvate thereof, wherein $R^2$ is H, —OH, $—N(R^{10})_2$, or $—O—C_{1-6}$alkyl. In some embodiments is a compound of Formula (I), or a pharmaceutically acceptable salt or solvate thereof, wherein $R^2$ is $—O—C_{1-6}$alkyl. In some embodiments is a compound of Formula (I), or a pharmaceutically acceptable salt or solvate thereof, wherein $R^2$ is $—OCH_2CH_3$. In some embodiments is a compound of Formula (I), or a pharmaceutically acceptable salt or solvate thereof, wherein $R^2$ is H. In some embodiments is a compound of Formula (I), or a pharmaceutically acceptable salt or solvate thereof, wherein n is 0.

In another aspect described herein is a pharmaceutical composition comprising a compound of Formula (I), or a pharmaceutically acceptable salt or solvate thereof, and a pharmaceutically acceptable excipient.

In another aspect described herein is a method of treating an inflammatory bowel disease in a patient in need thereof, comprising administering to the patient a therapeutically effective amount of a compound of Formula (I), or a pharmaceutically acceptable salt or solvate thereof. In some embodiments is a method of treating an inflammatory bowel disease in a patient in need thereof, comprising administering to the patient a therapeutically effective amount of a compound of Formula (I), or a pharmaceutically acceptable salt or solvate thereof, wherein the inflammatory bowel disease is selected from Crohn's disease, ulcerative colitis, and perianal Crohn's disease. In some cases, the ulcerative colitis is a severe form of ulcerative colitis. In some cases, the severe form of ulcerative colitis is medically refractory ulcerative colitis.

In another aspect described herein is a method of modulating GPR35 activity comprising contacting GPR35, or portion thereof, with a compound of Formula (I), or a pharmaceutically acceptable salt or solvate thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the context of this disclosure, a number of terms shall be utilized.

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein.

The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, C1-Cx includes C1-C2, C1-C3 . . . C1-Cx. C1-Cx refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$alkyl" or similar designations. By way of example only, "$C_1$-$C_6$alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a type of alkyl group in which the first two atoms of the alkyl group form a double bond that is not part of an aromatic group. That is, an alkenyl group begins with the atoms $—C(R)═CR_2$, wherein R refers to the remaining portions of the alkenyl group, which may be the same or different. Non-limiting examples of an alkenyl group include $—CH═CH_2$, $—C(CH_3)═CH_2$, $—CH═CHCH_3$, $—CH═C(CH_3)_2$ and $—C(CH_3)═CHCH_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, $—C≡CCH_3$, $—C≡CCH_2CH_3$ and $—C≡CCH_2CH_2CH_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a $—NH_2$ group.

The term "alkylamine" or "alkylamino" refers to the —N(alkyl)xHy group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a $—N(alkyl)_2$ group, where alkyl is as defined herein.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —$CO_2H$. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

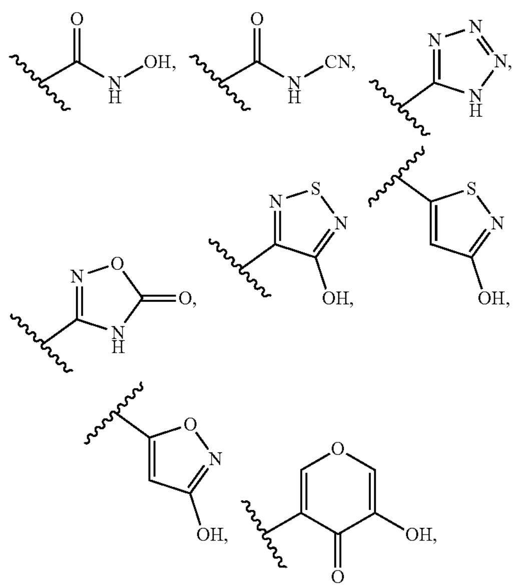

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include —$CH_2Cl$, —$CF_3$, —$CHF_2$, —$CH_2CF_3$, —$CF_2CF_3$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_2$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—$N(CH_3)$—$CH_3$, —$CH_2$—$CH_2$—NH—$CH_3$, —$CH_2$—$CH_2$—$N(CH_3)$—$CH_3$, —$CH_2$—S—$CH_2$—$CH_3$, —$CH_2$—$CH_2$—S(O)—$CH_3$, —$CH_2$—$CH_2$—$S(O)_2$—$CH_3$, —$CH_2$—NH—$OCH_3$, —$CH_2$—O—$Si(CH_3)_3$, —$CH_2$—CH═N—$OCH_3$, and —CH═CH—$N(CH_3)$—$CH_3$. In addition, up to two heteroatoms may be consecutive, such as, by way of example, —$CH_2$—NH—$OCH_3$ and —$CH_2$—O—$Si(CH_3)_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

"Optional" or "optionally" means that a subsequently described event or circumstance may or may not occur and that the description includes instances when the event or circumstance occurs and instances in which it does not.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —$N(R)_2$), and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, above.

As used herein, the term "about" or "approximately" means within 20%, preferably within 10%, and more preferably within 5% of a given value or range.

The term a "therapeutically effective amount" as used herein refers to the amount of a compound of Formula (I) that, when administered to a mammal in need, is effective to at least partially treat the conditions described herein.

The term "modulate" encompasses either a decrease or an increase in activity depending on the target molecule.

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

The term "patient" or "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts, and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable.

These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

As used herein, "medically refractory," or "refractory," as used herein, refers to the failure of a standard treatment to induce remission of a disease. In some embodiments, the disease comprises an inflammatory disease disclosed herein. A non-limiting example of refractory inflammatory disease includes refractory Crohn's disease, and refractory ulcerative colitis (e.g., medically refractory UC, or mrUC). Non-limiting examples of standard treatment include glucocorticosteroids, anti-TNFalpha therapy, anti-a4-b7 therapy (vedolizumab), anti-IL12p40 therapy (ustekinumab), Thalidomide, and Cytoxin.

G Protein-Coupled Receptor 35 (GPR35)

G Protein-Coupled Receptor 35 (GPR35) is a receptor for kynurenic acid, an intermediate in the tryptophan metabolic pathway. GPR35 mediates calcium mobilization and inositol phosphate production. GPR35, and nucleic acids encoding GPR35, are characterized by NCBI Entrez Gene ID 2859. Studies show that GPR35 is linked to inflammatory regulation, either by the presence of the receptor at the surface of immune specific cells, or by agonists activation leading to changes in immune response. Accordingly, it is hypothesized that GPR35, and nucleic acids encoding GPR35, play a role is inflammatory disease pathology making GPR35 an attractive therapeutic target to treat inflammatory diseases or conditions.

The compounds of Formula (I) described herein are GPR35 modulators. In some embodiments, compounds of Formula (I) described herein are GPR35 agonists. In some embodiments, compounds of Formula (I) described herein are GPR35 inverse agonists. In some embodiments, compounds of Formula (I) described herein are GPR35 antagonists. The compounds of Formula (I) described herein, and compositions comprising these compounds, are useful for the treatment of an inflammatory bowel disease.

In some embodiments, provided herein is a compound of Formula (I), or a pharmaceutically acceptable salt or solvate thereof:

Formula (I)

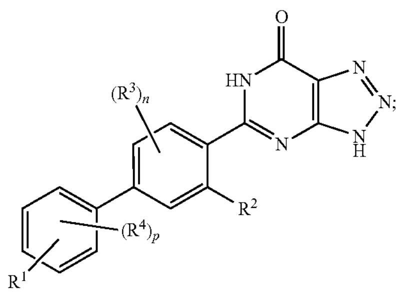

wherein:

$R^1$ is —$C_{1-6}$alkyl-C(O)N($R^{10}$)$_2$, —$C_{1-6}$alkyl-C(O)N(H)(OH), —$C_{1-6}$alkyl-C(O)N(H)($OCH_3$), —$C_{1-6}$alkyl-C(O)N(H)S(O)$_2$N($R^{10}$)$_2$, —O—$C_{1-6}$alkyl-C(O)N($R^{10}$)$_2$, —O—$C_{1-6}$alkyl-C(O)N(H)(OH), —O—$C_{1-6}$alkyl-C(O)N(H)($OCH_3$), —O—$C_{1-6}$alkyl-C(O)N(H)S(O)$_2$N($R^{10}$)$_2$, —C(H)═$R^5$, —$C_{1-6}$alkyl-$R^5$, or —$C_{1-6}$alkyl-$C_{1-9}$heteroaryl, wherein —$C_{1-6}$alkyl-$C_{1-9}$heteroaryl is optionally substituted with one, two, or three groups independently selected from halogen, $C_{1-6}$alkyl, $C_{1-6}$haloalkyl, and —C(O)O$R^{10}$;

$R^2$ is H, —OH, —N($R^{10}$)$_2$, —NHS(O)$_2R^9$, —S(O)$_2$N($R^{10}$)$_2$, —C(O)N($R^{10}$)$_2$, —OC(O)N($R^{10}$)$_2$, —O—$C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl;

each $R^3$ is independently selected from halogen, —CN, —OH, —O$R^9$, —S$R^9$, —N($R^{10}$)$_2$, —$NO_2$, —S(O)$R^9$, —S(O)$_2R^9$, —NHS(O)$_2R^9$, —S(O)$_2$N($R^{10}$)$_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each $R^4$ is independently selected from halogen, —CN, —OH, —O$R^9$, —S$R^9$, —N($R^{10}$)$_2$, —S(O)$R^9$, —S(O)$_2R^9$, —NHS(O)$_2R^9$, —S(O)$_2$N($R^{10}$)$_2$, —C(O)NHS(O)$_2$N($R^{10}$)$_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-$R^9$, —$C_{1-6}$alkyl-OH, —$C_{1-6}$alkyl-O$R^9$, —$C_{1-6}$alkyl-N($R^{10}$)$_2$, —$C_{1-6}$alkyl-C(O)O$R^{10}$, $C_{2-6}$alkenyl, —$C_{2-6}$alkenyl-C(O)O$R^{10}$, $C_{2-6}$alkynyl, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, and $C_{1-9}$heteroaryl; wherein $C_{3-8}$cycloalkyl, —$C_{1-6}$alkyl-$C_{3-8}$cycloalkyl, phenyl, —$C_{1-6}$alkyl-phenyl, and $C_{1-9}$heteroaryl are optionally substituted with one, two, or three groups independently selected from halogen, —C(O)O$R^{10}$, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl and —$C_{1-6}$alkyl-$C_{2-9}$heterocycloalkyl are optionally substituted with one, two, or three groups independently selected from halogen, —C(O)O$R^{10}$, $C_{1-6}$alkyl, $C_{1-6}$haloalkyl, and oxo;

$R^5$ is $C_{2-9}$heterocycloalkyl optionally substituted with one, two, or three groups independently selected from halogen, $C_{1-6}$alkyl, $C_{1-6}$haloalkyl, —C(O)O$R^{10}$, and oxo;

each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —O$R^{11}$, —N($R^{11}$)$_2$, $C_{1-6}$alkyl, $C_{3-8}$cycloalkyl, —N($R^{11}$)C(O)$R^{12}$, —C(O)$R^{12}$, and —C(O)O$R^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N($R^{11}$)$_2$, and —C(O)O$R^{12}$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each $R^{11}$ is independently selected from H and $C_{1-6}$alkyl;

each $R^{12}$ is independently selected from H and $C_{1-6}$alkyl;

n is 0, 1, 2, or 3; and p is 0, 1, 2, 3, or 4;

or a pharmaceutically acceptable salt or solvate thereof.

In some embodiments is a compound of Formula (I), or a pharmaceutically acceptable salt or solvate thereof, wherein $R^1$ is —C(H)═$R^5$. In some embodiments is a compound of Formula (I), or a pharmaceutically acceptable salt or solvate thereof, wherein $R^1$ is —$C_{1-6}$alkyl-$R^5$.

In some embodiments is a compound of Formula (I), or a pharmaceutically acceptable salt or solvate thereof, wherein $R^5$ is $C_{2-9}$heterocycloalkyl optionally substituted with one, two, or three groups independently selected from halogen, $C_{1-6}$alkyl, $C_{1-6}$haloalkyl, —C(O)O$R^{10}$, and oxo, wherein $C_{2-9}$heterocycloalkyl is selected from thiazolidinyl, oxazolidinyl, 2,5-dihydroisoxazolyl, and 4,5-dihydro-1,2,4-oxadiazolyl, piperidinyl, piperazinyl, morpholinyl, tetrahydropyranyl, tetrahydrofuranyl, pyrrolidinyl, oxetanyl, and azetidinyl. In some embodiments is a compound of Formula (I), or a pharmaceutically acceptable salt or solvate thereof, wherein $R^5$ is $C_{2-9}$heterocycloalkyl optionally substituted with one, two, or three groups independently selected from halogen, $C_{1-6}$alkyl, $C_{1-6}$haloalkyl, —C(O)OR$^{10}$, and oxo, wherein $C_{2-9}$heterocycloalkyl is selected from thiazolidinyl, oxazolidinyl, 2,5-dihydroisoxazolyl, and 4,5-dihydro-1,2,4-oxadiazolyl.

In some embodiments is a compound of Formula (I), or a pharmaceutically acceptable salt or solvate thereof, wherein $R^1$ is

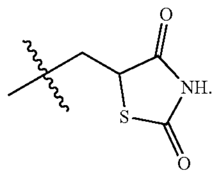 [SMILES: *CC1SC(=O)NC1=O]

In some embodiments is a compound of Formula (I), or a pharmaceutically acceptable salt or solvate thereof, wherein $R^1$ is

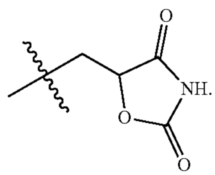 [SMILES: *CC1OC(=O)NC1=O]

In some embodiments is a compound of Formula (I), or a pharmaceutically acceptable salt or solvate thereof, wherein $R^1$ is

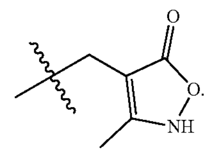 [SMILES: *Cc1c(C)[nH]oc1=O]

In some embodiments is a compound of Formula (I), or a pharmaceutically acceptable salt or solvate thereof, wherein $R^1$ is

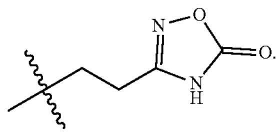 [SMILES: *CCc1noc(=O)[nH]1]

In some embodiments is a compound of Formula (I), or a pharmaceutically acceptable salt or solvate thereof, wherein $R^1$ is —$C_{1-6}$alkyl-C(O)N(R$^{10}$)$_2$. In some embodiments is a compound of Formula (I), or a pharmaceutically acceptable salt or solvate thereof, wherein $R^1$ is —$C_{1-6}$alkyl-C(O)NH$_2$.

In some embodiments is a compound of Formula (I), or a pharmaceutically acceptable salt or solvate thereof, wherein $R^1$ is

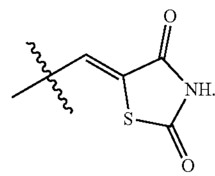 [SMILES: */C=C1\SC(=O)NC1=O]

In some embodiments is a compound of Formula (I), or a pharmaceutically acceptable salt or solvate thereof, wherein $R^1$ is

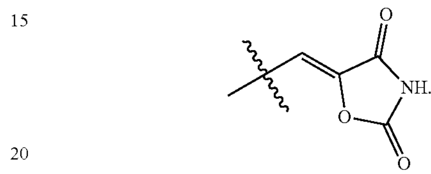

In some embodiments is a compound of Formula (I), or a pharmaceutically acceptable salt or solvate thereof, wherein $R^1$ is —$C_{1-6}$alkyl-C(O)N(H)(OH).

In some embodiments is a compound of Formula (I), or a pharmaceutically acceptable salt or solvate thereof, wherein $R^1$ is —$C_{1-6}$alkyl-C(O)N(H)(OCH$_3$).

In some embodiments is a compound of Formula (I), or a pharmaceutically acceptable salt or solvate thereof, wherein $R^1$ is —$C_{1-6}$alkyl-C(O)N(H)S(O)$_2$N(R$^{10}$)$_2$. In some embodiments is a compound of Formula (I), or a pharmaceutically acceptable salt or solvate thereof, wherein $R^1$ is —$C_{1-6}$alkyl-C(O)N(H)S(O)$_2$N(CH$_3$)$_2$. In some embodiments is a compound of Formula (I), or a pharmaceutically acceptable salt or solvate thereof, wherein $R^1$ is —$C_{1-6}$alkyl-C(O)N(H)S(O)$_2$NH$_2$.

In some embodiments is a compound of Formula (I), or a pharmaceutically acceptable salt or solvate thereof, wherein $R^1$ is —O—$C_{1-6}$alkyl-C(O)N(R$^{10}$)$_2$. In some embodiments is a compound of Formula (I), or a pharmaceutically acceptable salt or solvate thereof, wherein $R^1$ is —O—$C_{1-6}$alkyl-C(O)NH$_2$.

In some embodiments is a compound of Formula (I), or a pharmaceutically acceptable salt or solvate thereof, wherein $R^1$ is —O—$C_{1-6}$alkyl-C(O)N(H)(OH).

In some embodiments is a compound of Formula (I), or a pharmaceutically acceptable salt or solvate thereof, wherein $R^1$ is —O—$C_{1-6}$alkyl-C(O)N(H)(OCH$_3$).

In some embodiments is a compound of Formula (I), or a pharmaceutically acceptable salt or solvate thereof, wherein $R^1$ is —O—$C_{1-6}$alkyl-C(O)N(H)S(O)$_2$N(R$^{10}$)$_2$. In some embodiments is a compound of Formula (I), or a pharmaceutically acceptable salt or solvate thereof, wherein $R^1$ is —O—$C_{1-6}$alkyl-C(O)N(H)S(O)$_2$N(CH$_3$)$_2$. In some embodiments is a compound of Formula (I), or a pharmaceutically acceptable salt or solvate thereof, wherein $R^1$ is —O—$C_{1-6}$alkyl-C(O)N(H)S(O)$_2$NH$_2$.

In some embodiments is a compound of Formula (I), or a pharmaceutically acceptable salt or solvate thereof, wherein $R^1$ is —$C_{1-6}$alkyl-$C_{1-9}$heteroaryl optionally substituted with one, two, or three groups independently selected from halogen, $C_{1-6}$alkyl, $C_{1-6}$haloalkyl, and —C(O)OR$^{10}$. In some embodiments is a compound of Formula (I), or a pharmaceutically acceptable salt or solvate thereof, wherein $R^1$ is —$C_{1-6}$alkyl-$C_{1-9}$heteroaryl optionally substituted with one, two, or three groups independently selected from halogen, $C_{1-6}$alkyl, $C_{1-6}$haloalkyl, and —C(O)$OR^{10}$, wherein the $C_{1-9}$heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl. In some embodiments is a compound of Formula (I), or a pharmaceutically acceptable salt or solvate thereof, wherein $R^1$ is an unsubstituted —$C_{1-6}$alkyl-$C_{1-9}$heteroaryl. In some embodiments is a compound of Formula (I), or a pharmaceutically acceptable salt or solvate thereof, wherein $R^1$ is an unsubstituted —$C_{1-6}$alkyl-$C_{1-9}$heteroaryl, wherein the $C_{1-9}$heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl.

In some embodiments is a compound of Formula (I), or a pharmaceutically acceptable salt or solvate thereof, wherein $R^2$ is H, —OH, —$N(R^{10})_2$, or —O—$C_{1-6}$alkyl. In some embodiments is a compound of Formula (I), or a pharmaceutically acceptable salt or solvate thereof, wherein $R^2$ is —O—$C_{1-6}$alkyl. In some embodiments is a compound of Formula (I), or a pharmaceutically acceptable salt or solvate thereof, wherein $R^2$ is —$OCH_2CH_3$. In some embodiments is a compound of Formula (I), or a pharmaceutically acceptable salt or solvate thereof, wherein $R^2$ is H. In some embodiments is a compound of Formula (I), or a pharmaceutically acceptable salt or solvate thereof, wherein $R^2$ is —OH. In some embodiments is a compound of Formula (I), or a pharmaceutically acceptable salt or solvate thereof, wherein $R^2$ is —$N(R^{10})_2$.

In some embodiments is a compound of Formula (I), or a pharmaceutically acceptable salt or solvate thereof, wherein n is 0.

In some embodiments is a compound of Formula (I), or a pharmaceutically acceptable salt or solvate thereof, wherein n is 1, 2, or 3. In some embodiments is a compound of Formula (I), or a pharmaceutically acceptable salt or solvate thereof, wherein n is 1, 2, or 3 and each $R^3$ is independently selected from halogen, —CN, —$OR^9$, —$N(R^{10})_2$, —$S(O)_2R^9$, —$NHS(O)_2R^9$, —$S(O)_2N(R^{10})_2$, —C(O)$R^9$, —C(O)$OR^{10}$, —OC(O)$R^9$, —C(O)$N(R^{10})_2$, —$NR^{10}$C(O)N$(R^{10})_2$, —$NR^{10}$C(O)$R^9$, $C_{1-6}$alkyl, —$C_{1-6}$alkyl-OH, —$C_{1-6}$alkyl-$OR^9$, —$C_{1-6}$alkyl-$N(R^{10})_2$, $C_{1-6}$haloalkyl, $C_{3-8}$cycloalkyl, and —$C_{1-6}$alkyl-$C_{3-8}$cycloalkyl. In some embodiments is a compound of Formula (I), or a pharmaceutically acceptable salt or solvate thereof, wherein n is 1, 2, or 3 and each $R^3$ is independently selected from halogen, —$OR^9$, —$N(R^{10})_2$, —C(O)$OR^{10}$, —C(O)$N(R^{10})_2$, and $C_{1-6}$alkyl. In some embodiments is a compound of Formula (I), or a pharmaceutically acceptable salt or solvate thereof, wherein n is 1, 2, or 3 and each $R^3$ is independently selected from halogen and $C_{1-6}$alkyl. In some embodiments is a compound of Formula (I), or a pharmaceutically acceptable salt or solvate thereof, wherein n is 1. In some embodiments is a compound of Formula (I), or a pharmaceutically acceptable salt or solvate thereof, wherein n is 1 and $R^3$ is selected from halogen, —OH, —$OR^9$, —$N(R^{10})_2$, $C_{1-6}$alkyl, —$C_{1-6}$alkyl-OH, —$C_{1-6}$alkyl-$OR^9$, and $C_{1-6}$haloalkyl. In some embodiments is a compound of Formula (I), or a pharmaceutically acceptable salt or solvate thereof, wherein n is 1 and $R^3$ is selected from halogen, —$OR^9$, and $C_{1-6}$alkyl. In some embodiments is a compound of Formula (I), or a pharmaceutically acceptable salt or solvate thereof, wherein n is 1 and $R^3$ is selected from halogen, —$OR^9$, and $C_{1-6}$alkyl. In some embodiments is a compound of Formula (I), or a pharmaceutically acceptable salt or solvate thereof, wherein n is 1 and $R^3$ is —$OR^9$. In some embodiments is a compound of Formula (I), or a pharmaceutically acceptable salt or solvate thereof, wherein n is 1, $R^3$ is —$OR^9$, and $R^9$ is $C_{3-8}$cycloalkyl. In some embodiments is a compound of Formula (I), or a pharmaceutically acceptable salt or solvate thereof, wherein n is 1, $R^3$ is —$OR^9$, and $R^9$ is cyclopentyl.

In some embodiments, provided herein is a compound selected from:

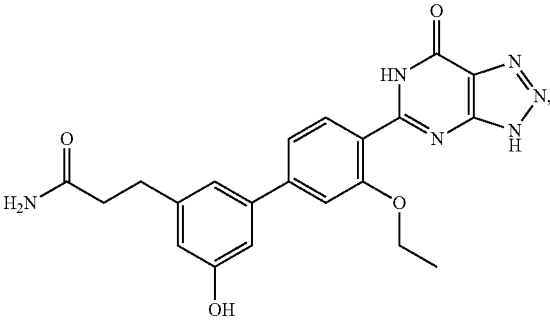

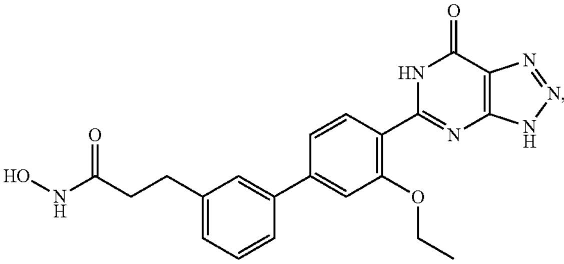

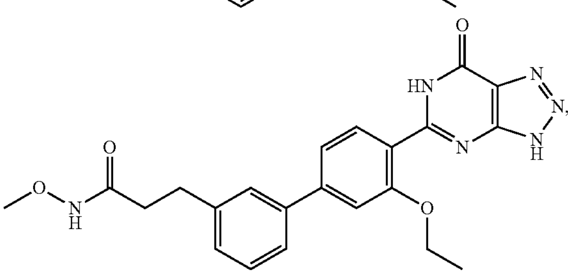

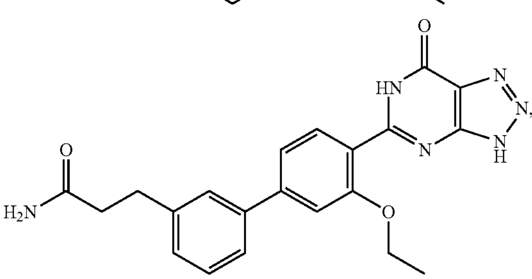

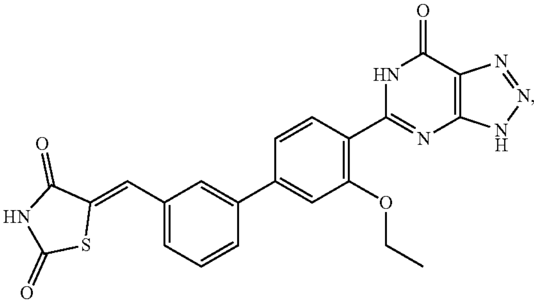

-continued
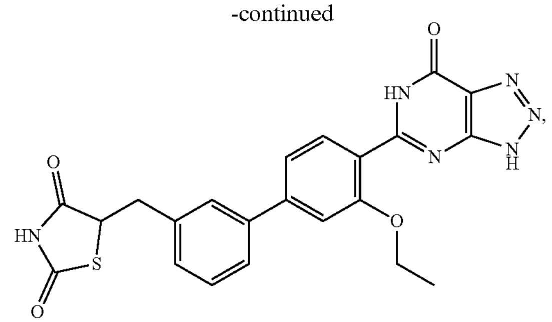
,
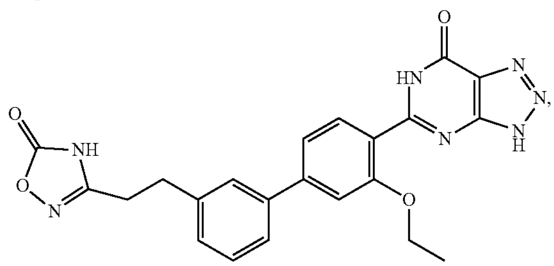
,
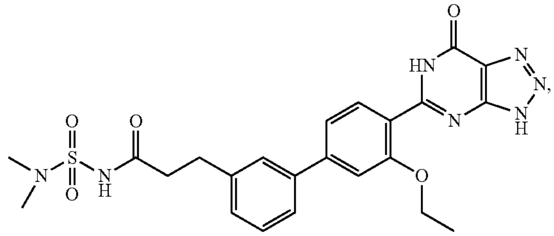
,
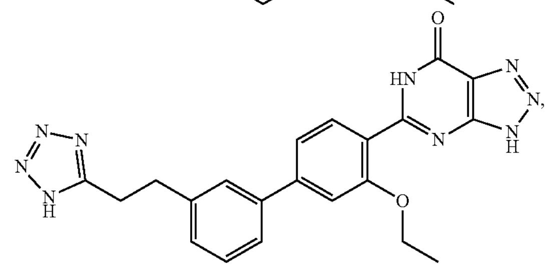
,
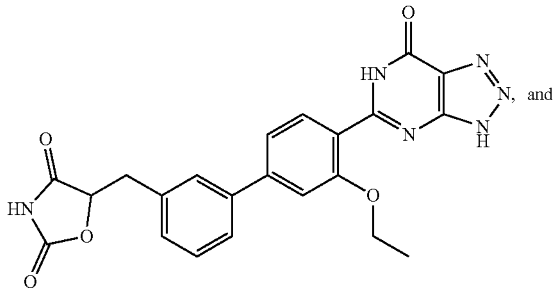
, and
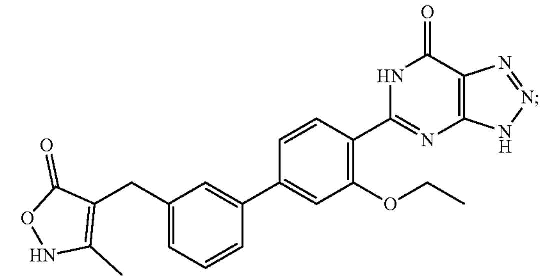
;
or a pharmaceutically acceptable salt or solvate thereof.
In some embodiments, provided herein is a compound selected from:
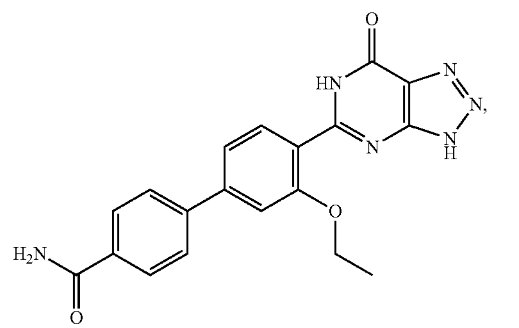
,
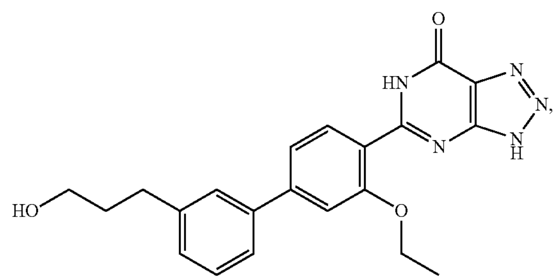
,
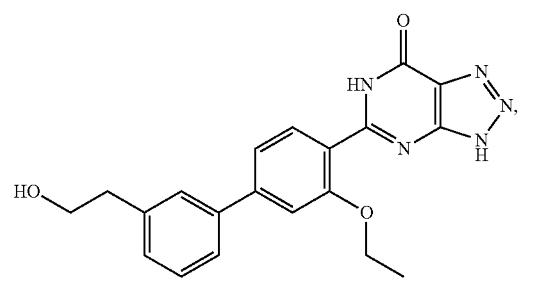
,
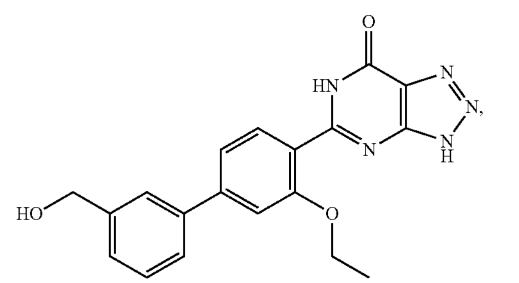
,
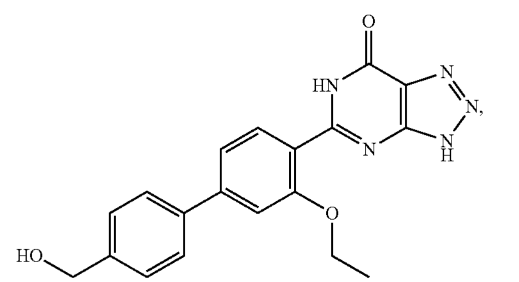
,
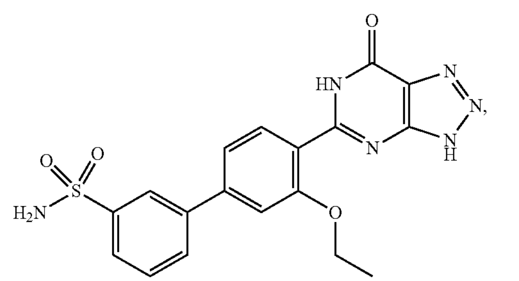
, -continued
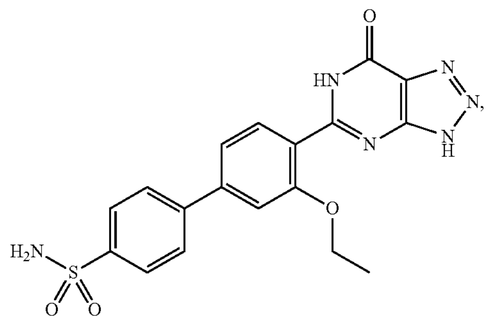
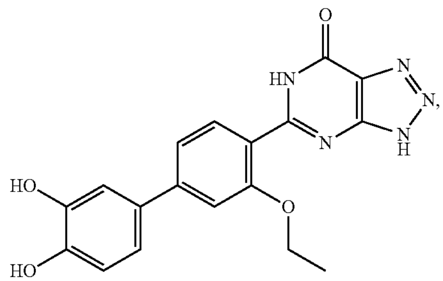
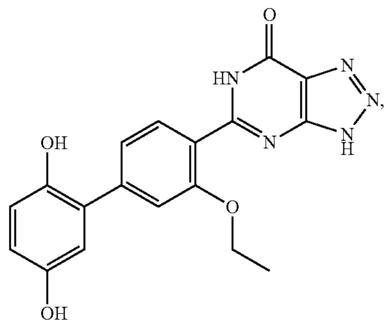
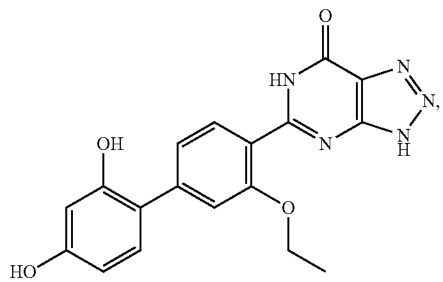
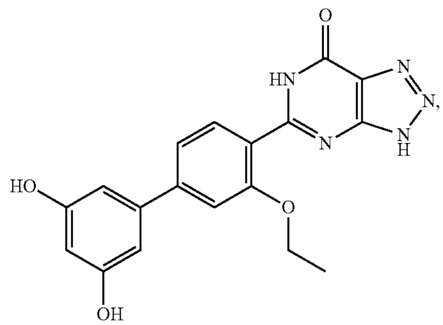
-continued
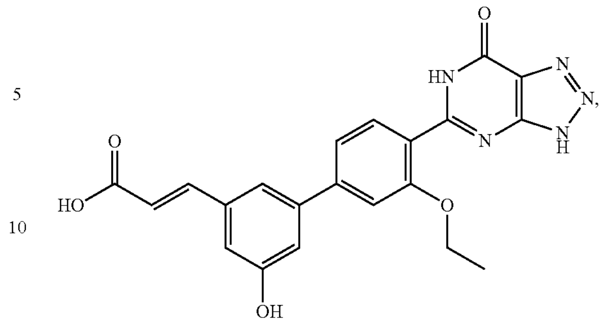
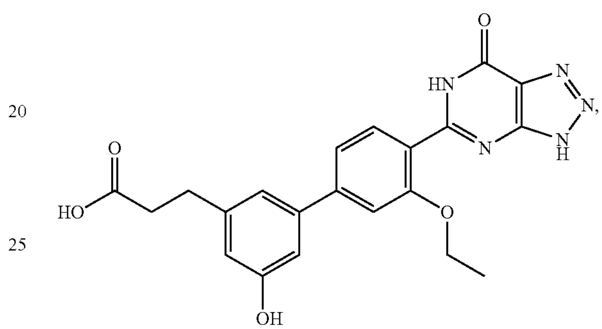
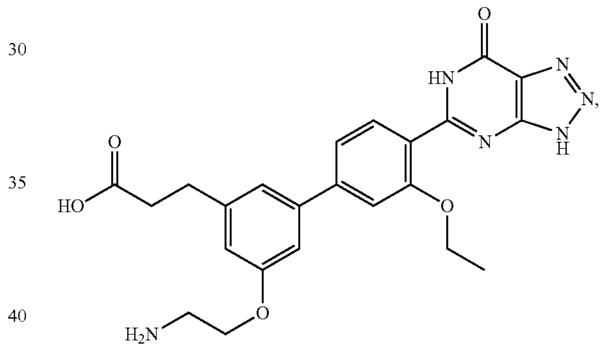
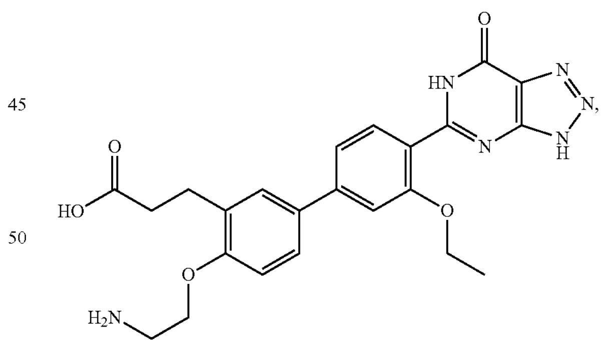
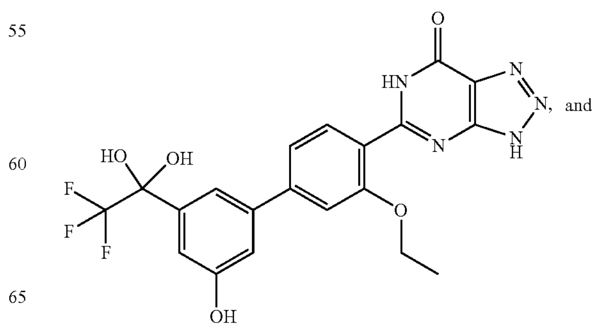
and -continued

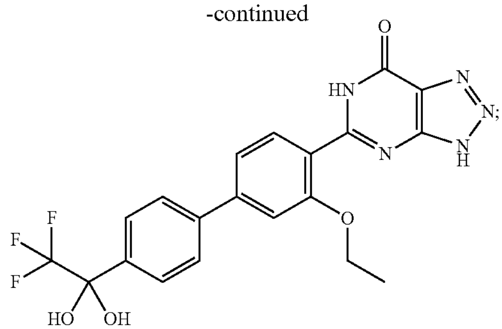

or a pharmaceutically acceptable salt or solvate thereof.

In some embodiments, provided herein is a compound selected from:

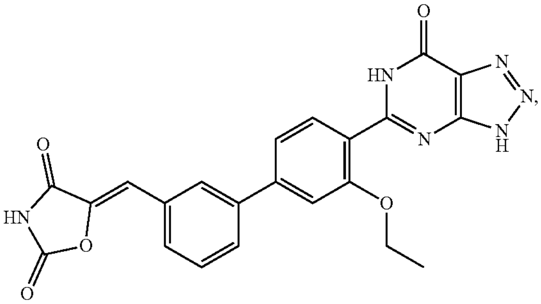

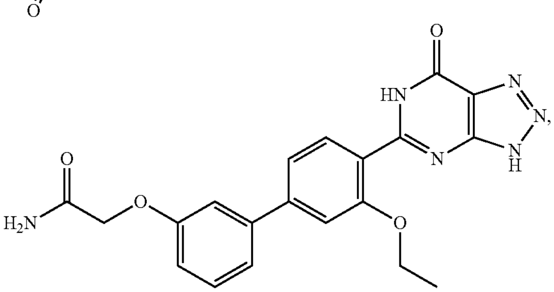

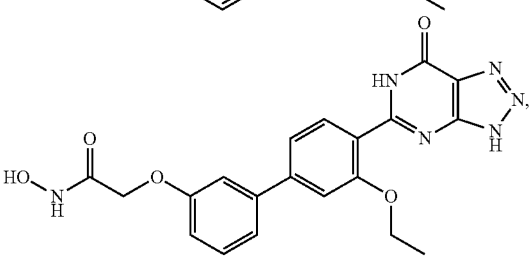

and

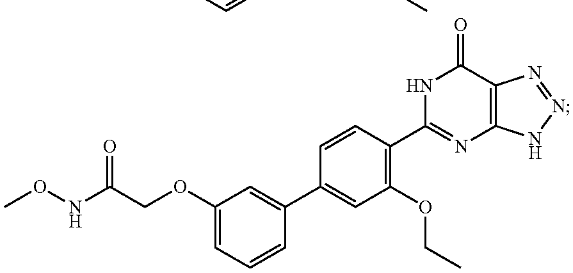

or a pharmaceutically acceptable salt or solvate thereof.

Any combination of the groups described above for the various variables is contemplated herein. Throughout the specification, groups and substituents thereof can be chosen by one skilled in the field to provide stable moieties and compounds.

In some embodiments, the therapeutic agent(s) (e.g. compound of Formula (I)) is present in the pharmaceutical composition as a pharmaceutically acceptable salt. In some embodiments, any compound described above is suitable for any method or composition described herein.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein.

In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^{2}H$, $^{3}H$, $^{13}C$, $^{14}C$, $^{5}N$, $^{17}O$, $^{18}O$, $^{31}P$ $^{32}P$, $^{35}S$, $^{18}F$, and $^{36}Cl$, respectively. Compounds described herein, and pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i. e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. As a guide the following synthetic methods may be utilized.

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a $Pd^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

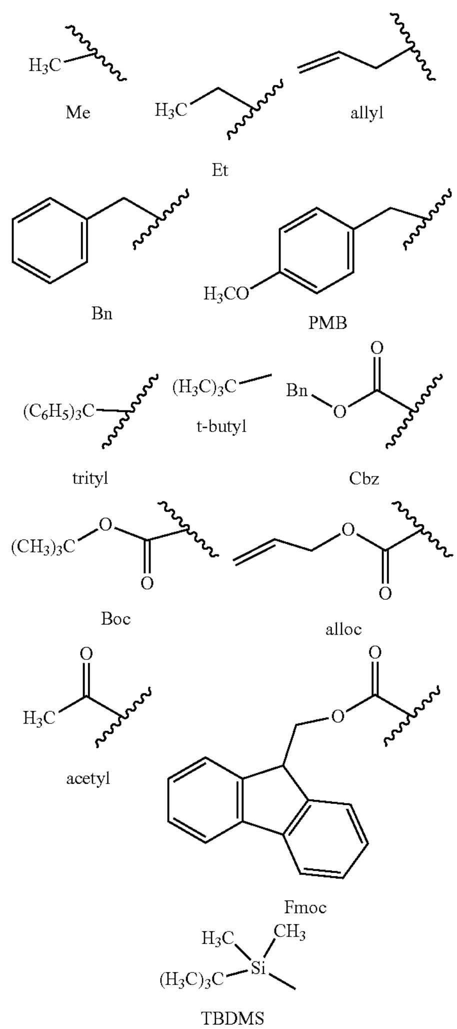

Me Et allyl

Bn PMB trityl t-butyl Cbz

Boc alloc acetyl Fmoc

TBDMS

Other protecting groups, plus a detailed description of techniques applicable to the creation of protecting groups and their removal are described in Greene and Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure).

Methods of Treatment and Prevention

In some embodiments is a method of treating an inflammatory bowel disease in a patient in need thereof, comprising administering to the patient a therapeutically effective amount of a compound of Formula (I), or a pharmaceutically acceptable salt or solvate thereof. In some embodiments is a method of treating an inflammatory bowel disease in a patient in need thereof, comprising administering to the patient a therapeutically effective amount of a compound of Formula (I), or a pharmaceutically acceptable salt or solvate thereof, wherein the inflammatory bowel disease is selected from Crohn's disease, ulcerative colitis, and perianal Crohn's disease. In some embodiments is a method of treating an inflammatory bowel disease in a patient in need thereof, comprising administering to the patient a therapeutically effective amount of a compound of Formula (I), or a pharmaceutically acceptable salt or solvate thereof, wherein the inflammatory bowel disease is Crohn's disease. In some embodiments is a method of treating an inflammatory bowel disease in a patient in need thereof, comprising administering to the patient a therapeutically effective amount of a compound of Formula (I), or a pharmaceutically acceptable salt or solvate thereof, wherein the inflammatory bowel disease is ulcerative colitis. In some cases, the ulcerative colitis is a severe form of ulcerative colitis. In some cases, the severe form of ulcerative colitis is medically refractory ulcerative colitis. In some embodiments is a method of treating an inflammatory bowel disease in a patient in need thereof, comprising administering to the patient a therapeutically effective amount of a compound of Formula (I), or a pharmaceutically acceptable salt or solvate thereof, wherein the inflammatory bowel disease is perianal Crohn's disease.

Pharmaceutical Compositions and Methods of Administration

In certain embodiments, the compounds described herein are administered as a pure chemical. In other embodiments, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, PA (2005)).

Accordingly, provided herein is a pharmaceutical composition comprising at least one compound described herein, or a pharmaceutically acceptable salt, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

In some embodiments is a pharmaceutical composition comprising a pharmaceutically acceptable carrier and a compound of Formula (I), or a pharmaceutically acceptable salt or solvate thereof.

Another embodiment provides a pharmaceutical composition consisting essentially of a pharmaceutically acceptable carrier and a compound of Formula (I), or a pharmaceutically acceptable salt or solvate thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, topical, buccal, parenteral (e.g., subcutaneous, intramuscular, intradermal, or intravenous), or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

In some embodiments, compositions and compounds described herein are administered to subjects in a biologically compatible form suitable for topical administration. Topical administration may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Dermal or skin patches are another method for transdermal delivery of the therapeutic or pharmaceutical compositions described herein. Patches can provide an absorption enhancer such as DMSO to increase the absorption of the compounds. Patches can include those that control the rate of drug delivery to the skin.

Ointments, pastes, creams and gels also can contain excipients, such as starch, tragacanth, cellulose derivatives, polyethylene glycols, silicones, bentonites, silicic acid, and talc, or mixtures thereof. Powders and sprays also can contain excipients such as lactose, talc, silicic acid, aluminum hydroxide, calcium silicates and polyamide powder, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such a chlorofluorohydrocarbons and volatile unsubstituted hydrocarbons, such as butane and propane.

The dose of the composition comprising at least one compound described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the compound of Formula (I) and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of a compound of Formula (I) can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

EXAMPLES

The following examples are offered for purposes of illustration and are not intended to limit the scope of the claims provided herein.

As used above, and throughout the description of the invention, the following abbreviations, unless otherwise indicated, shall be understood to have the following meanings:

ACN or MeCN acetonitrile
AcOH acetic acid
$AlMe_3$ trimethylaluminum
Bn benzyl
BOC or Boc t-butyl carbamate
CDI 1,1'-carbonyldiimidazole
$Cy_3P\ BF_4$ tricyclohexylphosphonium tetrafluoroborate
DCE dichloroethane
DCM dichloromethane
DDQ 2,3-dichloro-5,6-dicyano-p-benzoquinone
DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl EtOH ethanol
EA or EtOAc ethyl acetate
h hour
HPLC high performance liquid chromatography
LAH lithium aluminum hydride
Me methyl
MeOH methanol
MS mass spectroscopy
MSA methanesulfonic acid
NMM N-methylmorpholine
NMR nuclear magnetic resonance
$Pd(dppf)Cl_2$ [1,1'-bis(diphenylphosphino)ferrocene]dichloropalladium(II)
$Pd(DTBPF)Cl_2$ [1,1'-bis(di-tert-butylphosphino)ferrocene]dichloropalladium(II)
$Pd(OAc)_2$ palladium(II) acetate
PMB para-methoxybenzyl
rt room temperature
SEM 2-(trimethylsilyl)ethoxymethyl
TEA triethylamine
TFA trifluoroacetic acid
TFAA trifluoroacetic anhydride
THF tetrahydrofuran Example 1: Synthesis of 3'-Ethoxy-4'-(7-oxo-6,7-dihydro-3H-[1,2,3]triazolo[4,5-d]pyrimidin-5-yl)-[1,1'-biphenyl]-4-carboxamide (Compound 101)

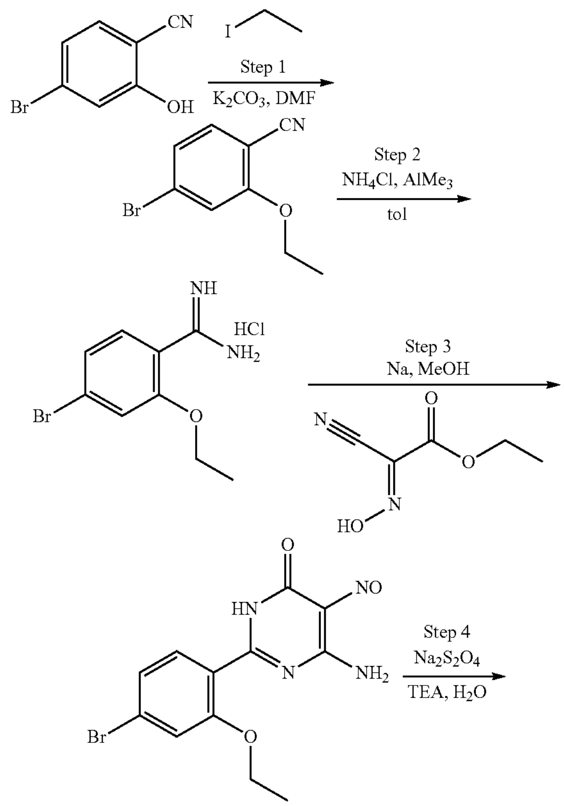

-continued

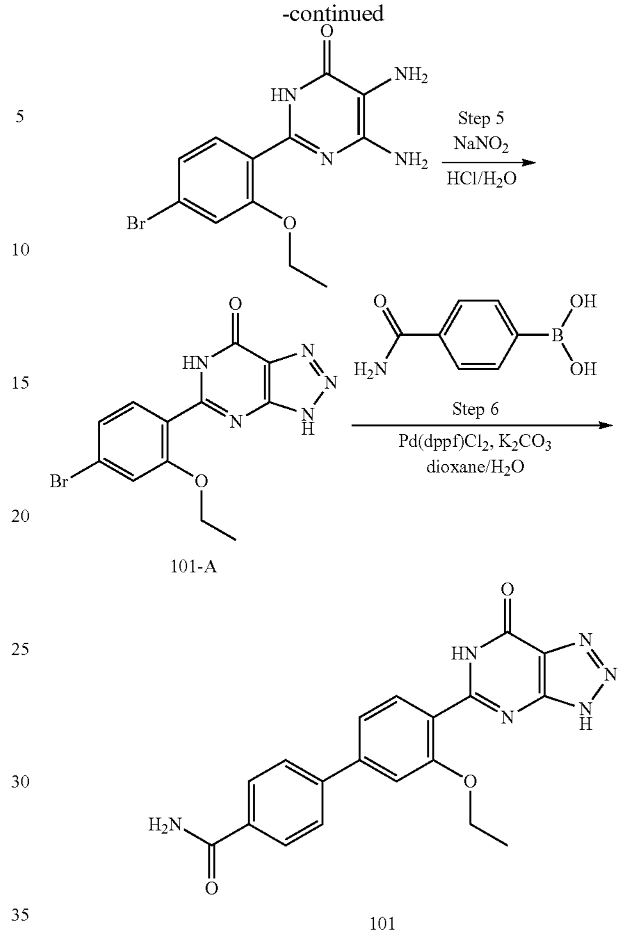

101-A

101

Step 1: To a stirred solution of 4-bromo-2-hydroxybenzonitrile (3.00 g, 15.2 mmol, 1.0 equiv) and $K_2CO_3$ (4.19 g, 30.3 mmol, 2.0 equiv) in DMF (30 mL) was added ethyl iodide (3.07 g, 19.7 mmol, 1.3 equiv) at room temperature and the resulting mixture was stirred overnight. The mixture was diluted with water (100 mL). The precipitated solids were collected by filtration and washed with water (2×20 mL). The resulting solid was dried under a heat lamp to afford 4-bromo-2-ethoxybenzonitrile (3 g, 88%) as an off-white solid.

Step 2: To a stirred mixture of $NH_4Cl$ (2.37 g, 44.2 mmol, 4.0 equiv) in toluene (20 mL) was added $AlMe_3$ (22.1 mL, 44.2 mmol, 4.0 equiv) dropwise at room temperature under nitrogen. The resulting mixture was stirred for 30 min at room temperature. To the above mixture was added 4-bromo-2-ethoxybenzonitrile (2.50 g, 11.1 mmol, 1.0 equiv) and the resulting mixture was stirred for additional 16 h at 110° C. The mixture was cooled to 0° C., and the reaction was quenched by the addition of methanol (50 mL) dropwise. The solid was filtered and the filter cake was washed with methanol (3×30 mL) and DCM (3×30 mL). The filtrate was concentrated under reduced pressure until a small amount of solvent remained. The residue was diluted with EA (30 mL) and the precipitated solids were collected by filtration and washed with EA (2×20 mL). The resulting solid was dried with an infrared lamp. This resulted in 4-bromo-2-ethoxybenzenecarboximidamide hydrochloride (3 g, 97%) as a white solid. LCMS (ESI)=243.1, 245.1 $[M+H]^+$.

Step 3: To a stirred solution of MeOH (30 mL) was added Na (0.99 g, 42.9 mmol, 4.0 equiv) in portions at room temperature under nitrogen. The resulting mixture was stirred until the solid was dissolved completely at room temperature. To the above mixture was added 4-bromo-2-ethoxybenzenecarboximidamide hydrochloride (3.00 g, 10.7 mmol, 1.0 equiv) and (E)-(ethyl cyano(hydroxyimino)formate) (3.05 g, 21.5 mmol, 2.0 equiv). The resulting mixture was refluxed overnight. The mixture was allowed to cool to room temperature and was quenched by the addition of water (100 mL). The mixture was acidified to pH 5.0 with AcOH. The precipitated solids were collected by filtration and washed with water (3×20 mL). The resulting solid was dried with an infrared lamp. This resulted in 6-amino-2-(4-bromo-2-ethoxyphenyl)-5-nitroso-3H-pyrimidin-4-one (3 g, 82%) as a green solid. LCMS (ESI)=338.8, 340.8 $[M+H]^+$.

Step 4: To a stirred solution of 6-amino-2-(4-bromo-2-ethoxyphenyl)-5-nitroso-3H-pyrimidin-4- one (2.00 g, 5.90 mmol, 1.0 equiv) in water (20 mL) and TEA (4.00 mL) was added $Na_2S_2O_4$ (3.08 g, 17.7 mmol, 3.0 equiv) at room temperature. The resulting mixture was stirred for 30 min. The resulting mixture was diluted with water (20 mL) then acidified to pH 5.0 with AcOH. The precipitated solids were collected by filtration and washed with water (2×10 mL). The resulting solid was dried with an infrared lamp. This resulted in 5,6-diamino-2-(4-bromo-2-ethoxyphenyl)-3H-pyrimidin-4-one (1 g, 52%) as a green solid. LCMS (ESI)=325.1, 327.1 $[M+H]^+$.

Step 5: To a stirred solution of 5,6-diamino-2-(4-bromo-2-ethoxyphenyl)-3H-pyrimidin-4-one) (1.0 g, 3.1 mmol) in HCl (6M) (10.0 mL) was added sodium nitrite (0.42 g, 6.15 mmol, 2.0 equiv) in portions at 0° C. The resulting mixture was stirred for 1 h at room temperature. The mixture was diluted with water (30 mL). The precipitated solids were collected by filtration and washed with water (2×10 mL). The crude product was purified by preparative HPLC to afford 5-(4-bromo-2-ethoxyphenyl)-3,6-dihydro-7H-[1,2,3]triazolo[4,5-d]pyrimidin-7-one (600 mg, 58%) as a white solid. LCMS (ESI)=336.0, 337.9 $[M+H]^+$. 1H NMR (300 MHz, DMSO-d6) δ 12.26 (s, 1H), 7.63 (d, J=8.2 Hz, 1H), 7.41 (d, J=1.7 Hz, 1H), 7.30 (dd, J=8.3, 1.7 Hz, 1H), 4.17 (q, J=6.9 Hz, 2H), 1.32 (t, J=6.9 Hz, 3H).

Step 6: To a solution of 5-(4-bromo-2-ethoxyphenyl)-3,6-dihydro-7H-[1,2,3]triazolo[4,5-d]pyrimidin-7-one (50.0 mg, 0.149 mmol, 1.0 equiv) and (4-carbamoylphenyl)boronic acid (29.4 mg, 0.178 mmol, 1.2 equiv) in dioxane (1.0 mL) and $H_2O$ (0.10 mL) was added $K_2CO_3$ (61.7 mg, 0.446 mmol, 3.0 equiv) and $Pd(DTBPF)Cl_2$ (9.7 mg, 0.015 mmol, 0.10 equiv). After stirring for 16 h at 100° C. under nitrogen, the resulting mixture was concentrated under reduced pressure. The mixture was purified by preparative HPLC (C18, 19*150 mm, A, water with 0.1% FA; B, ACN) to afford 3'-ethoxy-4'-(7-oxo-6,7-dihydro-3H-[1,2,3]triazolo[4,5-d]pyrimidin-5-yl)-[1,1'-biphenyl]-4-carboxamide (10.9 mg, 18.9%) as a white solid. LCMS (ESI)=375.1 $[M-H]^-$. $^1H$ NMR (300 MHz, DMSO-$d_6$) δ 12.1 (broad s, 1H), 8.07 (s, 1H), 8.01 (d, J=8.4 Hz, 2H), 7.94-7.84 (m, 3H), 7.50 (s, 1H), 7.49-7.40 (m, 2H), 4.33 (q, J=6.9 Hz, 2H), 1.41 (t, J=6.9 Hz, 3H).

Example 2: Synthesis of 5-(3-Ethoxy-3'-(3-hydroxypropyl)-[1,1'-biphenyl]-4-yl)-3,6-dihydro-7H-[1,2,3]triazolo[4,5-d]pyrimidin-7-one (Compound 102)

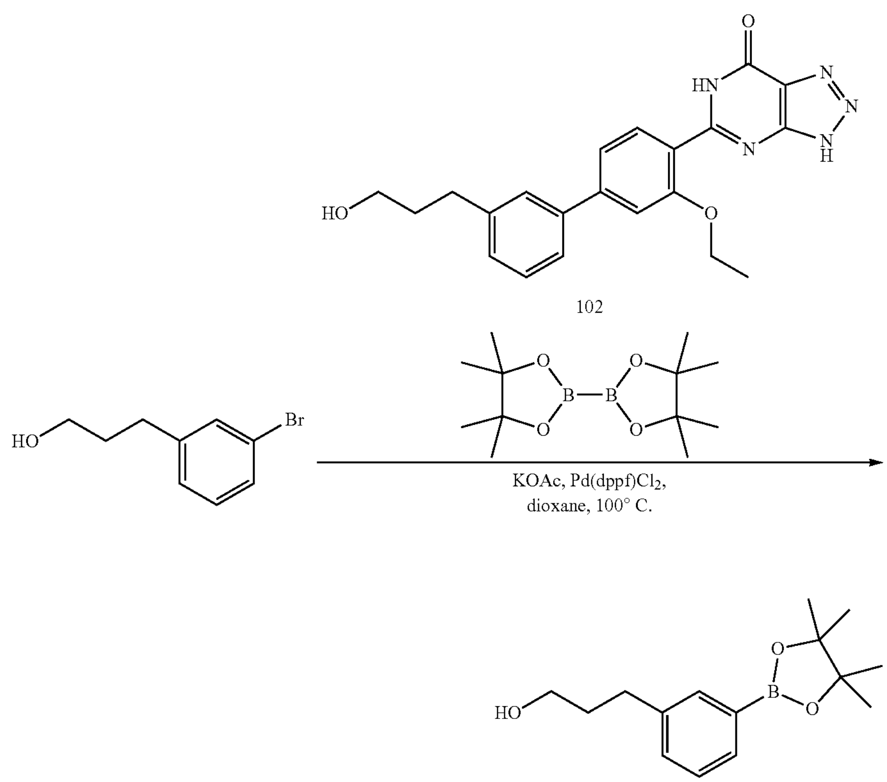

102

To a solution of 3-(3-bromophenyl)propan-1-ol (300 mg, 1.40 mmol, 1.0 equiv) and bis(pinacolato)diboron (531 mg, 2.09 mmol, 1.5 equiv) in dioxane (5.0 mL) was added KOAc (411 mg, 4.18 mmol, 3.0 equiv) and $Pd(dppf)Cl_2$-DCM (114 mg, 0.139 mmol, 0.10 equiv). After stirring for 3 h at 100° C. under nitrogen, the resulting mixture was concentrated under reduced pressure. The residue was purified by silica gel column chromatography, eluted with EA:PE (1:1) to afford 3-(3-(4,4,5,5-tetramethyl-1,3,2-dioxaborolan-2-yl)phenyl)propan-1-ol (500 mg) as an off-white solid. $^1H$ NMR (300 MHz, DMSO-$d_6$) δ 7.38 (d, J=1.7 Hz, 1H), 7.39-7.25 (m, 1H), 7.30-7.10 (m, 2H), 3.69 (t, J=6.4 Hz, 2H), 2.71 (dd, J=8.7, 6.8 Hz, 2H), 2.00-1.82 (m, 2H), 1.35 (s, 12H).

5-(3-Ethoxy-3'-(3-hydroxypropyl)-[1,1'-biphenyl]-4-yl)-3,6-dihydro-7H-[1,2,3]triazolo[4,5-d]pyrimidin-7-one was prepared using the procedures of Example 1. LCMS (ESI)=392.2 $[M+H]^+$. $^1H$ NMR (300 MHz, DMSO-$d_6$) δ 12.0 (broad s, 1H), 7.90 (d, J=8.5 Hz, 1H), 7.60 (s, 1H), 7.60-7.55 (m, 1H), 7.47-7.35 (m, 3H), 7.26 (d, J=7.5 Hz, 1H), 4.53-4.45 (m, 1H), 4.31 (q, J=6.9 Hz, 2H), 3.50-3.40 (m, 2H), 2.71 (t, J=7.8 Hz, 2H), 1.86-1.71 (m, 2H), 1.40 (t, J=6.9 Hz, 3H).

Example 3: Synthesis of 5-(3-Ethoxy-3'-(2-hydroxyethyl)-[1,1'-biphenyl]-4-yl)-3,6-dihydro-7H-[1,2,3]triazolo[4,5-d]pyrimidin-7-one (Compound 103)

103

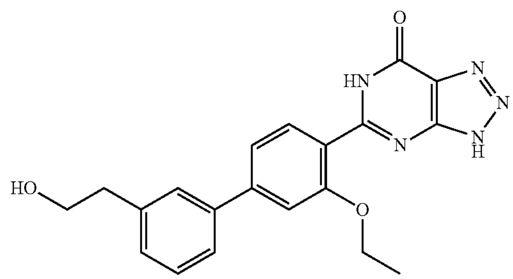

5-(3-Ethoxy-3'-(2-hydroxyethyl)-[1,1'-biphenyl]-4-yl)-3,6-dihydro-7H-[1,2,3]triazolo[4,5-d]pyrimidin-7-one was prepared using the procedures of Example 2 from 2-(3-bromophenyl)ethan-1-ol. LCMS (ESI)=378.2 $[M+H]^+$. $^1H$ NMR (300 MHz, DMSO-$d_6$) δ 7.93 (d, J=8.5 Hz, 1H), 7.64-7.56 (m, 2H), 7.46-7.35 (m, 3H), 7.27 (dt, J=7.5, 1.4 Hz, 1H), 4.29 (q, J=6.9 Hz, 2H), 3.66 (d, J=13.9 Hz, 1H), 2.82 (t, J=6.9 Hz, 2H), 1.40 (t, J=6.9 Hz, 3H).

Example 4: Synthesis of 5-(3-Ethoxy-3'-(hydroxymethyl)-[1,1'-biphenyl]-4-yl)-3,6-dihydro-7H-[1,2,3]triazolo[4,5-d]pyrimidin-7-one (Compound 104)

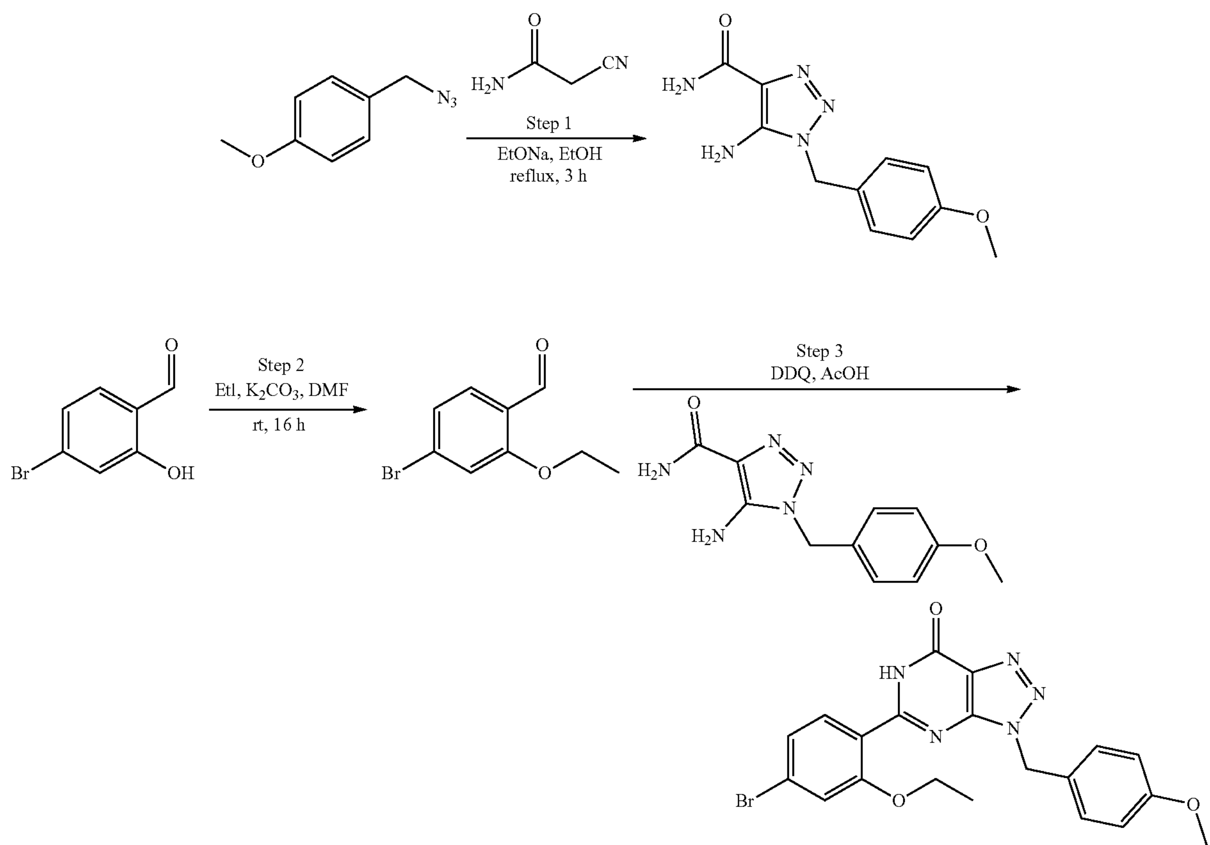

104-A

-continued

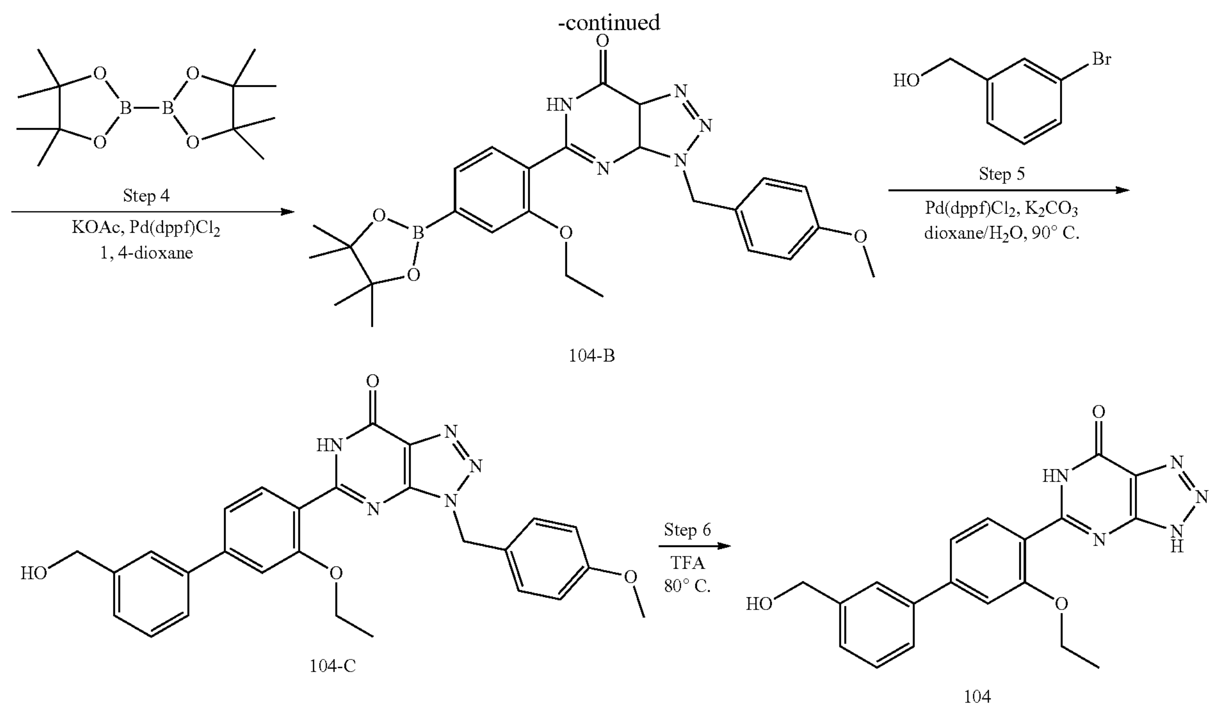

104-B

104-C

104

Step 1: To a stirred solution of 1-(azidomethyl)-4-methoxybenzene (5.00 g, 30.6 mmol, 1.0 equiv) and cyanoacetamide (2.58 g, 30.6 mmol, 1.0 equiv) in EtOH (50 mL) was added EtONa (6.26 g, 91.9 mmol, 3.0 equiv) at room temperature under nitrogen. The resulting mixture was heated at reflux for 3 h. The mixture was allowed to cool to room temperature. The precipitated solids were collected by filtration and washed with EtOH (2×10 mL). The resulting solid was dried under an infrared lamp. This resulted in 5-amino-1-[(4-methoxyphenyl)methyl]-1,2,3-triazole-4-carboxamide (3 g, 40%) as a grey solid.

Step 2: To a stirred solution of 4-bromo-2-hydroxybenzaldehyde (2.00 g, 9.95 mmol, 1.0 equiv) and $K_2CO_3$ (2.75 g, 19.9 mmol, 2.0 equiv) in DMF (20 mL) was added ethyl iodide (1.86 g, 11.9 mmol, 1.2 equiv) at room temperature and the resulting mixture was stirred overnight. The mixture was diluted with water (100 mL), and the precipitated solids were collected by filtration and washed with water (2×20 mL). The resulting solid was dried under an infrared lamp. This resulted in 4-bromo-2-ethoxybenzaldehyde (1.9 g, 83%) as a white solid.

Step 3: To a stirred solution of 5-amino-1-[(4-methoxyphenyl)methyl]-1,2,3-triazole-4-carboxamide (1.50 g, 6.07 mmol, 1.0 equiv) and 4-bromo-2-ethoxybenzaldehyde (2.08 g, 9.10 mmol, 1.5 equiv) in AcOH (20 mL) was added DDQ (2.75 g, 12.1 mmol, 2.0 equiv) at room temperature. The resulting mixture was stirred for 24 h at 80° C. The mixture was allowed to cool to room temperature. The resulting mixture was diluted with water (50 mL). The precipitated solids were collected by filtration and washed with water (2×10 mL). The residue was re-dissolved with sodium bicarbonate aqueous solution (50 mL). The precipitated solids were collected by filtration and washed with sodium bicarbonate aqueous solution (2×10 mL) and water (2×10 mL). The resulting solid was dried under an infrared lamp. This resulted in 5-(4-bromo-2-ethoxyphenyl)-3-(4-methoxybenzyl)-3,6-dihydro-7H-[1,2,3]triazolo[4,5-d]pyrimidin-7-one (1.5 g, crude) as a grey solid. The crude product (30 mg) was purified by preparative HPLC to afford 5-(4-bromo-2-ethoxyphenyl)-3-(4-methoxybenzyl)-3,6-dihydro-7H-[1,2,3]triazolo[4,5-d]pyrimidin-7-one (7 mg) as a white solid for analysis. LCMS (ESI)=456 $[M+H]^+$. $^1H$ NMR (300 MHz, DMSO-$d_6$) δ 12.44 (s, 1H), 7.68 (d, J=8.3 Hz, 1H), 7.43 (d, J=1.5 Hz, 1H), 7.35 (d, J=8.4 Hz, 3H), 6.92 (d, J=8.7 Hz, 2H), 5.69 (s, 2H), 4.18 (q, J=6.9 Hz, 2H), 3.73 (s, 3H), 1.32 (t, J=6.9 Hz, 3H).

Step 4: Into a 40 mL vial was added 5-(4-bromo-2-ethoxyphenyl)-3-(4-methoxybenzyl)-3,6-dihydro-7H-[1,2,3]triazolo[4,5-d]pyrimidin-7-one (1.00 g, 2.19 mmol, 1.0 equiv), bis(pinacolato)diboron (1.11 g, 4.37 mmol, 2.0 equiv), KOAc (645 mg, 6.57 mmol, 3.0 equiv) and Pd(dppf)$Cl_2$ (160 mg, 0.219 mmol, 0.10 equiv) in 1,4-dioxane (10 mL) at rt under N2. The resulting mixture was heated for 2 h at 100° C., then the reaction was quenched by the addition of water (100 mL) at rt. The precipitated solids were collected by filtration and washed with water (2×10 mL) and petroleum ether (2×10 mL) and dried to afford 5-(2-ethoxy-4-(4,4,5,5-tetramethyl-1,3,2-dioxaborolan-2-yl)phenyl)-3-(4-methoxybenzyl)-3,6-dihydro-7H-[1,2,3]triazolo[4,5-d]pyrimidin-7-one (1.3 g, crude) as a brown solid. LCMS (ESI)=502.2 $[M+H]^+$.

Step 5: To a solution of 5-(2-ethoxy-4-(4,4,5,5-tetramethyl-1,3,2-dioxaborolan-2-yl)phenyl)-3-(4-methoxybenzyl)-3,6-dihydro-7H-[1,2,3]triazolo[4,5-d]pyrimidin-7-one (60.0 mg, 0.119 mmol, 1.0 equiv) and (3-bromophenyl)methanol (26.8 mg, 0.143 mmol, 1.2 equiv) in dioxane (1.0 mL) and $H_2O$ (0.10 mL) was added $K_2CO_3$ (33.0 mg, 0.238 mmol, 2.0 equiv) and Pd(dppf)$Cl_2$-DCM (9.7 mg, 0.012 mmol, 0.10 equiv). After stirring for 3 h at 90° C. under nitrogen, the resulting mixture was concentrated under reduced pressure. The residue was purified by silica gel column chromatography, eluted with EA/PE (0%-100%) to afford 5-(3-ethoxy-3'-(hydroxymethyl)-[1,1'-biphenyl]-4-yl)-3-(4-methoxybenzyl)-3,6-dihydro-7H-[1,2,3]triazolo[4,5-d]pyrimidin-7-one (40 mg, 69%) as an off-white solid. LCMS (ESI)=484.3 $[M+H]^+$.

Step 6: A solution of 5-(3-ethoxy-3'-(hydroxymethyl)-[1,1'-biphenyl]-4-yl)-3-(4-methoxybenzyl)-3,6-dihydro-7H-[1,2,3]triazolo[4,5-d]pyrimidin-7-one (45.0 mg, 0.093 mmol, 1.0 equiv) in TFA (1.0 mL) was stirred for 3 h at 80° C. The mixture was allowed to cool to room temperature. The resulting mixture was concentrated under reduced pressure and the residue was purified by preparative HPLC to afford 5-(3-ethoxy-3'-(hydroxymethyl)-[1,1'-biphenyl]-4-yl)-3,6-dihydro-7H-[1,2,3]triazolo[4,5-d]pyrimidin-7-one (14.9 mg, 43.3%) as a white solid. LCMS (ESI)=364.2 $[M+H]^+$. $^1$H NMR (300 MHz, DMSO-$d_6$) δ 11.9 (broad s, 1H), 7.93 (d, J=8.4 Hz, 1H), 7.72 (s, 1H), 7.66 (d, J=7.7 Hz, 1H), 7.47 (t, J=7.6 Hz, 1H), 7.46-7.35 (m, 3H), 5.28 (broad s, 1H), 4.61 (s, 2H), 4.32 (q, J=6.9 Hz, 2H), 1.42 (t, J=6.9 Hz, 3H).

Example 5: Synthesis of 5-(3-Ethoxy-4'-(hydroxymethyl)-[1,1'-biphenyl]-4-yl)-3,6-dihydro-7H-[1,2,3]triazolo[4,5-d]pyrimidin-7-one (Compound 105)

105

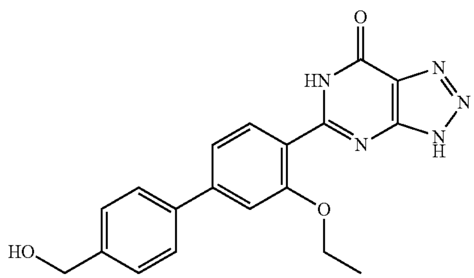

5-(3-Ethoxy-4'-(hydroxymethyl)-[1,1'-biphenyl]-4-yl)-3,6-dihydro-7H-[1,2,3]triazolo[4,5-d]pyrimidin-7-one was prepared using the procedures in Example 4 from (4-bromophenyl)methanol. LCMS (ESI)=364.2 $[M+H]^+$. $^1$H NMR (300 MHz, DMSO-$d_6$) δ 11.8 (broad s, 1H), 7.94 (d, J=8.4 Hz, 1H), 7.76 (d, J=8.1 Hz, 2H), 7.50-7.37 (m, 4H), 5.26 (broad s, 1H), 4.57 (d, J=4.8 Hz, 2H), 4.32 (q, J=6.8 Hz, 2H), 1.42 (t, J=6.9 Hz, 3H).

Example 6: Synthesis of 3'-Ethoxy-4'-(7-oxo-6,7-dihydro-3H-[1,2,3]triazolo[4,5-d]pyrimidin-5-yl)-[1,1'-biphenyl]-3-sulfonamide (Compound 106)

106

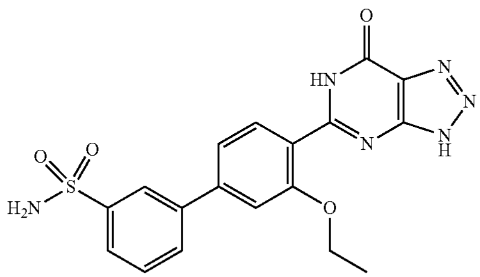

3'-Ethoxy-4'-(7-oxo-6,7-dihydro-3H-[1,2,3]triazolo[4,5-d]pyrimidin-5-yl)-[1,1'-biphenyl]-3-sulfonamide was prepared using the procedures in Example 4 from 3-bromobenzenesulfonamide. LCMS (ESI)=413.2 $[M+H]^+$. $^1$H NMR (300 MHz, DMSO-$d_6$) δ 8.18 (broad s, 1H), 8.06-7.96 (m, 2H), 7.86 (d, J=7.8 Hz, 1H), 7.70 (t, J=7.8 Hz, 1H), 7.43 (d, J=6.8 Hz, 2H), 4.31 (q, J=6.9 Hz, 2H), 1.42 (t, J=6.9 Hz, 3H).

Example 7: Synthesis of 3'-Ethoxy-4'-(7-oxo-6,7-dihydro-3H-[1,2,3]triazolo[4,5-d]pyrimidin-5-yl)-[1,1'-biphenyl]-4-sulfonamide (Compound 107)

107

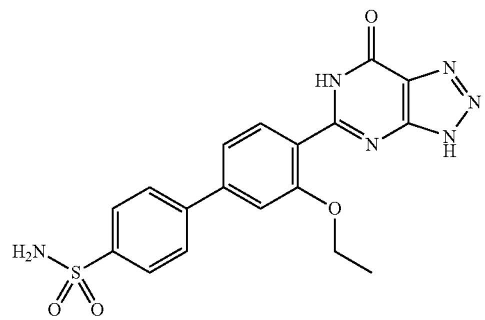

3'-Ethoxy-4'-(7-oxo-6,7-dihydro-3H-[1,2,3]triazolo[4,5-d]pyrimidin-5-yl)-[1,1'-biphenyl]-4-sulfonamide was prepared using the procedures in Example 4 from 4-bromobenzenesulfonamide. LCMS (ESI)=413.2 $[M+H]^+$. $^1$H NMR (300 MHz, DMSO-$d_6$) δ 8.10-7.90 (m, 5H), 7.49 (s, 1H), 7.49-7.43 (m, 1H), 4.31 (q, J=6.9 Hz, 2H), 1.40 (t, J=6.9 Hz, 3H).

Example 8: Synthesis of 5-(3-Ethoxy-3',4'-dihydroxy-[1,1'-biphenyl]-4-yl)-3,6-dihydro-7H-[1,2,3]triazolo[4,5-d]pyrimidin-7-one (Compound 108)

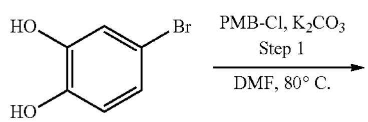

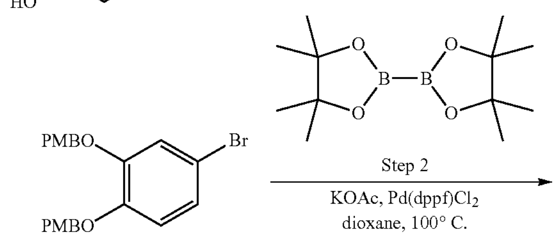

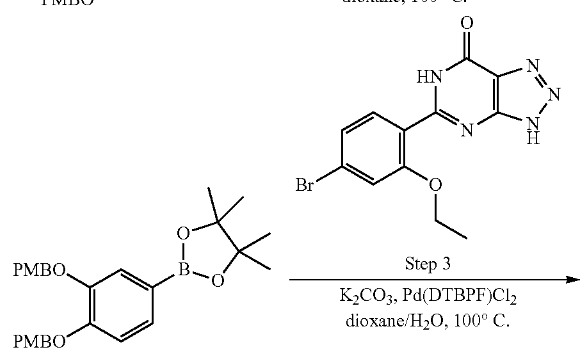

-continued

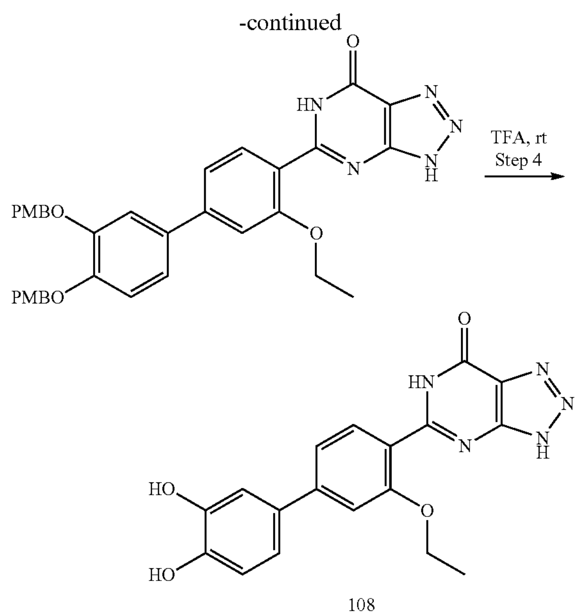

108

Step 1: To a stirred solution of 4-bromocatechol (500 mg, 2.64 mmol, 1.0 equiv) and $K_2CO_3$ (1.10 g, 7.94 mmol, 3.0 equiv) in DMF (10 mL) was added 4-methoxybenzyl chloride (911 mg, 5.82 mmol, 2.2 equiv) at room temperature. The resulting mixture was stirred for 2 h at 80° C.

The mixture was diluted with water (50 mL) and extracted with EA (2×10 mL). The combined organic layers were washed with brine (20 mL), dried over anhydrous $Na_2SO_4$, filtered, and concentrated under reduced pressure. The residue was purified by silica gel column chromatography, eluted with EA:PE (1:10) to afford 4,4'-(((4-bromo-1,2-phenylene)bis(oxy))bis(methylene))bis(methoxybenzene) (550 mg, 48.4%) as a white solid.

Step 2: To a solution of 4,4'-(((4-bromo-1,2-phenylene)bis(oxy))bis(methylene))bis(methoxybenzene) (200 mg, 0.466 mmol, 1.0 equiv) and bis(pinacolato)diboron (142 mg, 0.559 mmol, 1.2 equiv) in dioxane (2.0 mL) was added KOAc (137 mg, 1.40 mmol, 3.0 equiv) and $Pd(dppf)Cl_2$-DCM (38.0 mg, 0.047 mmol, 0.10 equiv). After stirring for 2 h at 100° C. under nitrogen, the resulting mixture was concentrated under reduced pressure. The residue was purified by silica gel column chromatography, eluted with EA:PE (1:10) to afford 2-(3,4-bis((4-methoxybenzyl)oxy)phenyl)-4,4,5,5-tetramethyl-1,3,2-dioxaborolane (210 mg, 94.6%) as a white solid.

Step 3: To a solution of 5-(4-bromo-2-ethoxyphenyl)-3,6-dihydro-7H-[1,2,3]triazolo[4,5-d]pyrimidin-7-one (50.0 mg, 0.149 mmol, 1.0 equiv) and 2-(3,4-bis((4-methoxybenzyl)oxy)phenyl)-4,4,5,5-tetramethyl-1,3,2-dioxaborolane (85.0 mg, 0.178 mmol, 1.2 equiv) in dioxane (1.0 mL) and $H_2O$ (0.30 mL) was added $K_2CO_3$ (61.7 mg, 0.446 mmol, 3.0 equiv) and $Pd(DTBPF)Cl_2$ (9.7 mg, 0.015 mmol, 0.10 equiv). After stirring for 16 h at 90° C. under nitrogen, the resulting mixture was allowed to cool to room temperature. The resulting mixture was purified by reverse phase flash chromatography to afford 5-(3-ethoxy-3',4'-bis((4-methoxybenzyl)oxy)-[1,1'-biphenyl]-4-yl)-3,6-dihydro-7H-[1,2,3]triazolo[4,5-d]pyrimidin-7-one (50 mg, 56%) as a yellow solid. LCMS (ESI)=606.4 $[M+H]^+$.

Step 4: A solution of 5-(3-ethoxy-3',4'-bis((4-methoxybenzyl)oxy)-[1,1'-biphenyl]-4-yl)-3,6-dihydro-7H-[1,2,3]triazolo[4,5-d]pyrimidin-7-one (50.0 mg, 0.083 mmol, 1.0 equiv) in TFA (1.5 mL) was stirred for 16 h at room temperature. The resulting mixture was concentrated under reduced pressure. The residue was purified by preparative HPLC to afford 5-(3-ethoxy-3',4'-dihydroxy-[1,1'-biphenyl]-4-yl)-3,6-dihydro-7H-[1,2,3]triazolo[4,5-d]pyrimidin-7-one (6.5 mg, 21%) as a yellow solid. LCMS (ESI)=366.2 $[M+H]^+$. $^1H$ NMR (300 MHz, DMSO-$d_6$) δ 12.11 (s, 1H), 9.24 (s, 1H), 9.06 (s, 1H), 7.85 (d, J=8.5 Hz, 1H), 7.33-7.23 (m, 2H), 7.15 (d, J=2.2 Hz, 1H), 7.08 (dd, J=8.2, 2.2 Hz, 1H), 6.86 (d, J=8.2 Hz, 1H), 4.29 (q, J=6.9 Hz, 2H), 1.40 (t, J=6.9 Hz, 3H).

Example 9: Synthesis of 5-(3-Ethoxy-2',5'-dihydroxy-[1,1'-biphenyl]-4-yl)-3,6-dihydro-7H-[1,2,3]triazolo[4,5-d]pyrimidin-7-one (Compound 109)

109

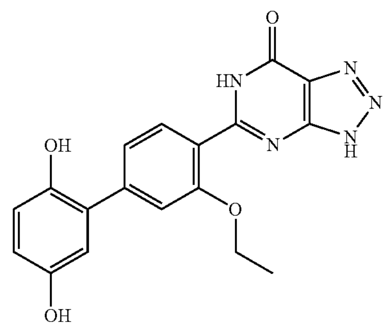

5-(3-Ethoxy-2',5'-dihydroxy-[1,1'-biphenyl]-4-yl)-3,6-dihydro-7H-[1,2,3]triazolo[4,5-d]pyrimidin-7-one was prepared using the procedures in Example 8 from 2-bromo-1,4-benzenediol. LCMS (ESI)=366.2 $[M+H]^+$. $^1H$ NMR (300 MHz, DMSO-$d_6$) δ 12.1 (s, 1H), 7.84 (d, J=8.1 Hz, 1H), 7.32 (d, J=1.5 Hz, 1H), 7.26 (dd, J=8.1, 1.5 Hz, 1H), 6.83-6.73 (m, 2H), 6.64 (dd, J=8.6, 3.0 Hz, 1H), 4.21 (q, J=6.9 Hz, 2H), 1.38 (t, J=6.9 Hz, 3H).

Example 10: Synthesis of 5-(3-Ethoxy-2',4'-dihydroxy-[1,1'-biphenyl]-4-yl)-3,6-dihydro-7H-[1,2,3]triazolo[4,5-d]pyrimidin-7-one (Compound 110)

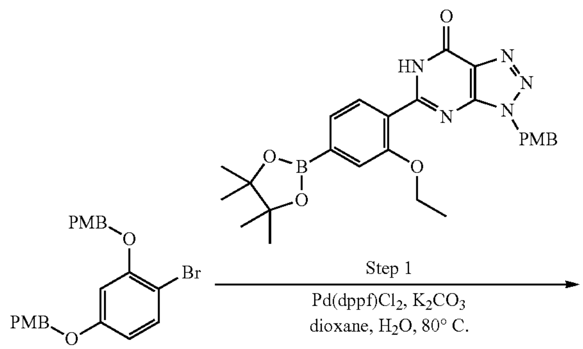

-continued

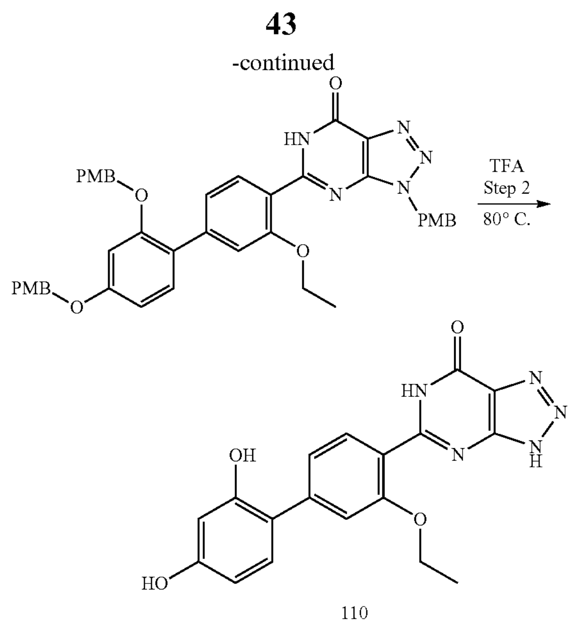

110

Step 1: To a solution of 5-(2-ethoxy-4-(4,4,5,5-tetramethyl-1,3,2-dioxaborolan-2-yl)phenyl)-3-(4-methoxybenzyl)-3,6-dihydro-7H-[1,2,3]triazolo[4,5-d]pyrimidin-7-one (50.0 mg, 0.099 mmol, 1.0 equiv) and 4,4'-(((4-bromo-1,3-phenylene)bis(oxy))bis(methylene))bis(methoxybenzene) (prepared using the procedure from Example 8, Step 1) (51.2 mg, 0.119 mmol, 1.2 equiv) in dioxane (1.0 mL) and water (0.10 mL) was added $K_2CO_3$ (41.2 mg, 0.298 mmol, 3.0 equiv) and Pd(dppf)$Cl_2$ (7.3 mg, 0.010 mmol, 0.1 equiv). After stirring for 2 h at 80° C. under nitrogen, the resulting mixture was concentrated under reduced pressure. The residue was purified by silica gel column chromatography, eluted with EA/PE (0-50%) to afford 5-(3-ethoxy-2',4'-bis((4-methoxybenzyl)oxy)-[1,1'-biphenyl]-4-yl)-3-(4-methoxybenzyl)-3,6-dihydro-7H-[1,2,3]triazolo[4,5-d]pyrimidin-7-one (60 mg, 67%) as a yellow solid. LCMS (ESI)=726.3 $[M+H]^+$.

Step 2: A solution of 5-(3-ethoxy-2',4'-bis((4-methoxybenzyl)oxy)-[1,1'-biphenyl]-4-yl)-3-(4-methoxybenzyl)-3,6-dihydro-7H-[1,2,3]triazolo[4,5-d]pyrimidin-7-one (60.0 mg, 0.083 mmol, 1.0 equiv) in TFA (2 mL) was stirred for 3 h at 80° C. The resulting mixture was concentrated under vacuum. The mixture was purified by preparative HPLC to afford 5-(3-ethoxy-2',4'-dihydroxy-[1,1'-biphenyl]-4-yl)-3,6-dihydro-7H-[1,2,3]triazolo[4,5-d]pyrimidin-7-one (2.3 mg, 7.2%) as a white solid. LCMS (ESI)=413.2 $[M+H]^+$. $^1$H NMR (300 MHz, DMSO-$d_6$+$D_2O$ exchange) δ 8.26 (s, 1H), 7.93 (d, J=8.1 Hz, 1H), 7.32-7.15 (m, 3H), 6.43 (d, J=2.4 Hz, 1H), 6.35 (dd, J=8.4, 2.4 Hz, 1H), 4.22 (q, J=6.9 Hz, 2H), 1.41 (t, J=6.9 Hz, 3H).

Example 11: Synthesis of 5-(3-Ethoxy-3',5'-dihydroxy-[1,1'-biphenyl]-4-yl)-3,6-dihydro-7H-[1,2,3]triazolo[4,5-d]pyrimidin-7-one (Compound 111)

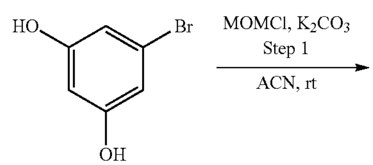

-continued

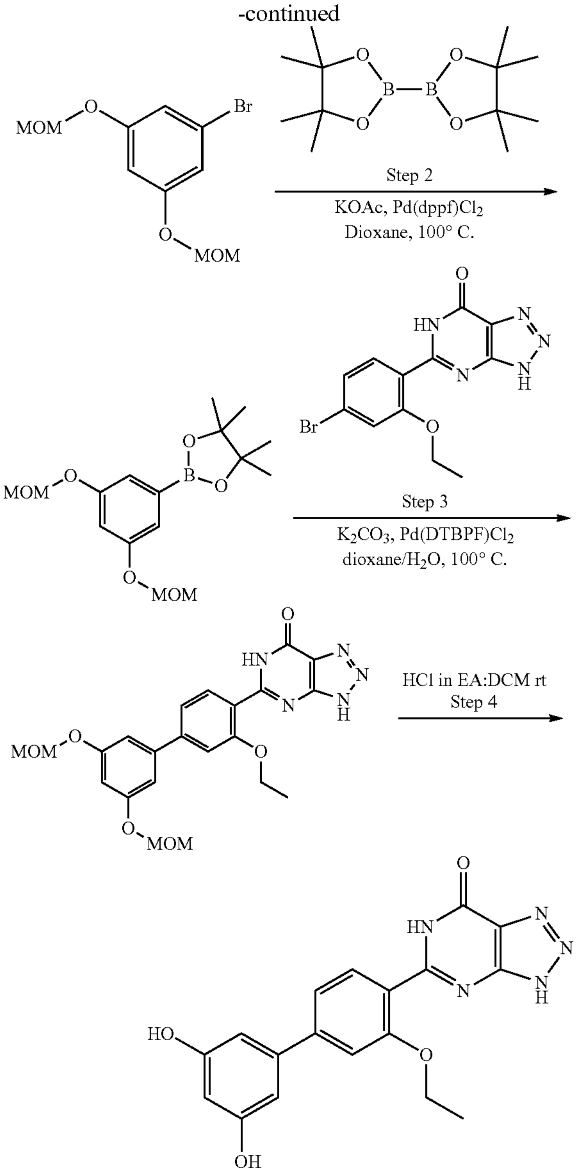

111

Step 1: To a stirred solution of 5-bromobenzene-1,3-diol (500 mg, 2.64 mmol, 1.0 equiv) and $K_2CO_3$ (1.10 g, 7.94 mmol, 3.0 equiv) in ACN (5.0 mL) was added MOM-Cl (387 mg, 5.82 mmol, 2.2 equiv) dropwise at 0° C. The resulting mixture was allowed to warm to rt and stirred for 12 h. The reaction was cooled to 0° C. and quenched with water (20 mL). The resulting mixture was extracted with EA (2×40 mL). The combined organic layers were washed with brine (20 mL), dried over anhydrous $Na_2SO_4$, filtered, and concentrated under reduced pressure. The residue was purified by silica gel column chromatography, eluted with EA/PE (0-20%) to afford 1-bromo-3,5-bis(methoxymethoxy)benzene (400 mg, 45.3%) as a white oil. $^1$H NMR (300 MHz, $CDCl_3$) δ 6.90 (s, 2H), 6.65 (s, 1H), 5.13 (s, 4H), 3.49 (s, 6H).

Step 2: To a solution of 1-bromo-3,5-bis(methoxymethoxy)benzene (200 mg, 0.722 mmol, 1.0 equiv) and bis(pinacolato)diboron (219 mg, 0.866 mmol, 1.2 equiv) in dioxane (2.0 mL) was added KOAc (142 mg, 1.44 mmol, 2.0 equiv) and Pd(dppf)$Cl_2$ (52.8 mg, 0.072 mmol, 0.1 equiv). After stirring for 4 h at 100° C. under nitrogen, the resulting mixture was concentrated under reduced pressure. The residue was purified by silica gel column chromatography, eluted with EA/PE (0-20%) to afford 2-(3,5-bis(methoxymethoxy)phenyl)-4,4,5,5-tetramethyl-1,3,2-dioxaborolane (150 mg, 62.5%) as a yellow oil. $^1$H NMR (300 MHz, $CDCl_3$) δ 7.12 (s, 2H), 6.80 (s, 1H), 5.15 (s, 4H), 3.50 (s, 6H), 1.32 (s, 12H).

Step 3: To a solution of 5-(4-bromo-2-ethoxyphenyl)-3,6-dihydro-7H-[1,2,3]triazolo[4,5-d]pyrimidin-7-one (40.0 mg, 0.119 mmol, 1.0 equiv) and 2-(3,5-bis(methoxymethoxy)phenyl)-4,4,5,5-tetramethyl-1,3,2-dioxaborolane (46.3 mg, 0.143 mmol, 1.2 equiv) in dioxane (1.0 mL) and $H_2O$ (0.30 mL) was added $K_2CO_3$ (49.3 mg, 0.357 mmol, 3.0 equiv) and Pd(DTBPF)$Cl_2$ (7.8 mg, 0.012 mmol, 0.1 equiv). After stirring for 16 h at 100° C. under nitrogen, the resulting mixture was concentrated under reduced pressure. The residue was purified by reverse-phase flash chromatography to afford 5-(3-ethoxy-3',5'-bis(methoxymethoxy)-[1,1'-biphenyl]-4-yl)-3,6-dihydro-7H-[1,2,3]triazolo[4,5-d]pyrimidin-7-one (25 mg, 46.3%) as a yellow solid. LCMS (ESI)=454.2 [M+H]$^+$.

Step 4: A solution of 5-(3-ethoxy-3',5'-bis(methoxymethoxy)-[1,1'-biphenyl]-4-yl)-3,6-dihydro-7H-[1,2,3]triazolo[4,5-d]pyrimidin-7-one (25.0 mg, 0.055 mmol, 1.0 equiv) and HCl(g) in EA (1.0 mL) in DCM (1.0 mL) was stirred for 2 h at rt. The resulting mixture was concentrated under reduced pressure. The residue was purified by preparative HPLC to afford 5-(3-ethoxy-3',5'-dihydroxy-[1,1'-biphenyl]-4-yl)-3,6-dihydro-7H-[1,2,3]triazolo[4,5-d]pyrimidin-7-one (10 mg, 49%) as a white solid. LCMS (ESI)=364.1 [M−H]$^-$. $^1$H NMR (300 MHz, DMSO-$d_6$) δ 12.2 (broad s, 1H), 9.43 (s, 2H), 7.86 (d, J=8.0 Hz, 1H), 7.32-7.22 (m, 2H), 6.57 (d, J=2.2 Hz, 2H), 6.28 (t, J=2.1 Hz, 1H), 4.26 (q, J=6.9 Hz, 2H), 1.38 (t, J=6.9 Hz, 3H).

Example 12: Synthesis of 3-(3'-Ethoxy-5-hydroxy-4'-(7-oxo-6,7-dihydro-3H-[1,2,3]triazolo[4,5-d]pyrimidin-5-yl)-[1,1'-biphenyl]-3-yl)propanoic acid (Compound 112)

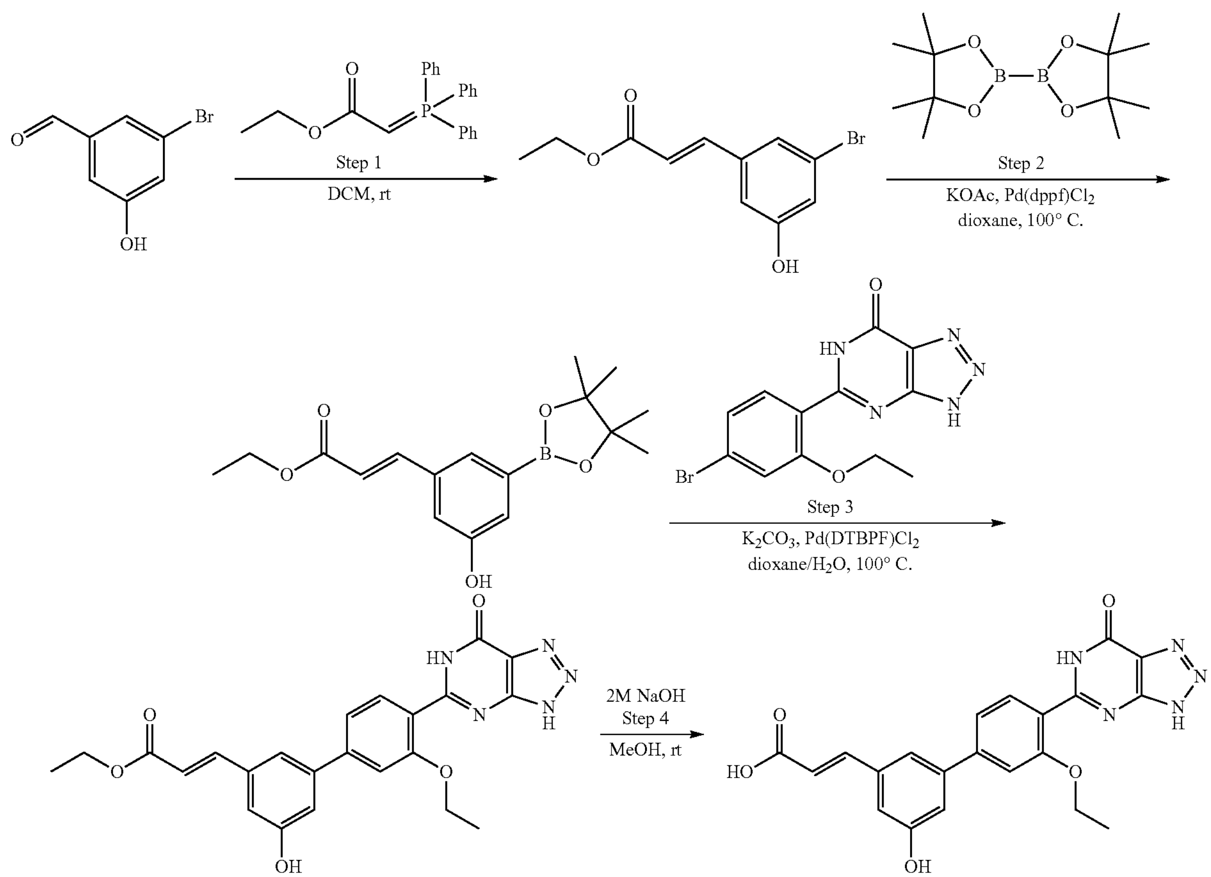

112

Step 1: A solution of 3-bromo-5-hydroxybenzaldehyde (200 mg, 0.995 mmol, 1.0 equiv) and ethyl 2-(triphenyl-2'-phosphanylidene)acetate (416 mg, 1.19 mmol, 1.2 equiv) in DCM (2.0 mL) was stirred for 3 h at room temperature. The resulting mixture was purified by silica gel column chromatography, eluted with EA:PE (1:3) to afford ethyl (E)-3-(3-bromo-5-hydroxyphenyl)acrylate (220 mg, 81.6%) as an off-white solid.

Step 2: To a solution of ethyl (E)-3-(3-bromo-5-hydroxyphenyl)acrylate (220 mg, 0.811 mmol, 1.0 equiv) and bis(pinacolato)diboron (309 mg, 1.22 mmol, 1.5 equiv) in dioxane (2.5 mL) were added KOAc (239 mg, 2.43 mmol, 3.0 equiv) and Pd(dppf)$Cl_2$-DCM (66.3 mg, 0.081 mmol, 0.10 equiv). After stirring for 2 h at 100° C. under nitrogen, the resulting mixture was allowed to cool to room temperature. The resulting mixture was purified by silica gel column chromatography, eluted with EA:PE (1:3) to afford ethyl (E)-3-(3-hydroxy-5-(4,4,5,5-tetramethyl-1,3,2-dioxaborolan-2-yl)phenyl)acrylate (250 mg, 96.8%) as an off-white solid.

Step 3: To a solution of ethyl (E)-3-(3-hydroxy-5-(4,4,5,5-tetramethyl-1,3,2-dioxaborolan-2-yl)phenyl)acrylate (60.0 mg, 0.189 mmol, 1.0 equiv) and 5-(4-bromo-2-ethoxyphenyl)-3,6-dihydro-7H-[1,2,3]triazolo[4,5-d]pyrimidin-7-one (76.1 mg, 0.226 mmol, 1.2 equiv) in dioxane (1.0 mL) and water (0.10 mL) was added $K_2CO_3$ (78.2 mg, 0.566 mmol, 3.0 equiv) and Pd(DTBPF)$Cl_2$ (12.3 mg, 0.019 mmol, 0.1 equiv). After stirring for 16 h at 100° C. under nitrogen, the resulting mixture was concentrated under reduced pressure. The residue was purified by silica gel column chromatography, eluted with MeOH/DCM (0-20%) to afford ethyl (E)-3-(3'-ethoxy-5-hydroxy-4'-(7-oxo-6,7-dihydro-3H-[1,2,3]triazolo[4,5-d]pyrimidin-5-yl)-[1,1'-biphenyl]-3-yl)acrylate (50 mg, 52%) as a yellow solid.

Step 4: A solution of ethyl (E)-3-(3'-ethoxy-5-hydroxy-4'-(7-oxo-6,7-dihydro-3H-[1,2,3]triazolo[4,5-d]pyrimidin-5-yl)-[1,1'-biphenyl]-3-yl)acrylate (50.0 mg, 0.112 mmol, 1.0 equiv) and 2M NaOH (0.30 mL) in MeOH (2.0 mL) was stirred for 2 h at rt. The mixture was acidified to pH 5-6 with FA. The mixture was purified by preparative HPLC to afford (E)-3-(3'-ethoxy-5-hydroxy-4'-(7-oxo-6,7-dihydro-3H-[1,2,3]triazolo[4,5-d]pyrimidin-5-yl)-[1,1'-biphenyl]-3-yl) acrylic acid (15 mg, 30%) as a white solid. LCMS (ESI)=418.1 $[M-H]^-$. $^1$H NMR (300 MHz, methanol-$d_4$) δ 8.30 (s, 1H), 7.99 (d, J=7.9 Hz, 1H), 7.59 (d, J=15.9 Hz, 1H), 7.51 (s, 1H), 7.40 (s, 1H), 7.40-7.35 (m, 1H), 7.19 (t, J=1.9 Hz, 1H), 7.07 (t, J=1.9 Hz, 1H), 6.57 (d, J=15.9 Hz, 1H), 4.40 (q, J=6.9 Hz, 2H), 1.58 (t, J=6.9 Hz, 3H).

Example 13: Synthesis of 3-(3'-Ethoxy-5-hydroxy-4'-(7-oxo-6,7-dihydro-3H-[1,2,3]triazolo[4,5-d]pyrimidin-5-yl)-[1,1'-biphenyl]-3-yl)propanoic acid (Compound 113)

113

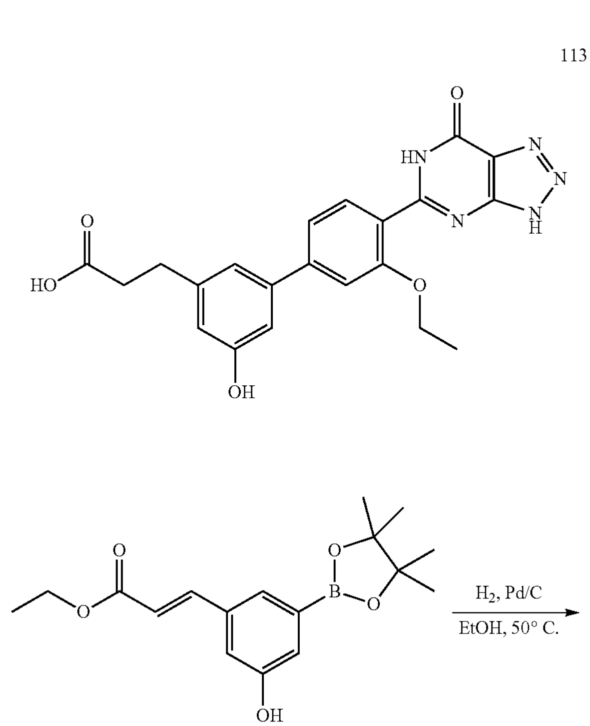

-continued

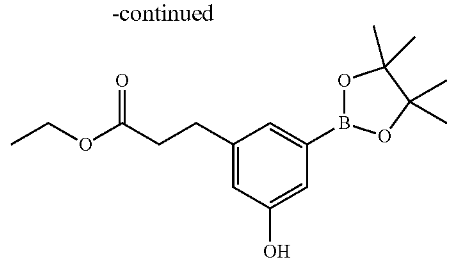

To a solution of ethyl (E)-3-(3-hydroxy-5-(4,4,5,5-tetramethyl-1,3,2-dioxaborolan-2-yl)phenyl)acrylate (100 mg, 0.314 mmol, 1.0 equiv) in 10 mL EtOH was added Pd/C (10%, 20 mg) under nitrogen. The mixture was heated at 50° C. for 16 h under a hydrogen atmosphere using a hydrogen balloon, then filtered through a Celite pad and concentrated under reduced pressure. The residue was purified by silica gel column chromatography, eluted with EA/PE (0-50%) to afford ethyl 3-(3-hydroxy-5-(4,4,5,5-tetramethyl-1,3,2-dioxaborolan-2-yl)phenyl)propanoate (100 mg, 99.4%) as a yellow oil.

3-(3'-Ethoxy-5-hydroxy-4'-(7-oxo-6,7-dihydro-3H-[1,2,3]triazolo[4,5-d]pyrimidin-5-yl)-[1,1'-biphenyl]-3-yl)propanoic acid was prepared using the procedures in Example 12. LCMS (ESI)=422.2 $[M+H]^+$. $^1$H NMR (300 MHz, DMSO-$d_6$) δ 9.55 (broad s, 1H), 7.97 (d, J=8.5 Hz, 1H), 7.35-7.26 (m, 2H), 7.06 (t, J=1.6 Hz, 1H), 6.96 (t, J=1.9 Hz, 1H), 6.69 (t, J=1.8 Hz, 1H), 4.30 (q, J=6.9 Hz, 2H), 2.83 (t, J=7.6 Hz, 2H), 1.42 (t, J=6.9 Hz, 3H).

Example 14: Synthesis of 3-(3'-Ethoxy-5-hydroxy-4'-(7-oxo-6,7-dihydro-3H-[1,2,3]triazolo[4,5-d]pyrimidin-5-yl)-[1,1'-biphenyl]-3-yl)propanamide (Compound 114)

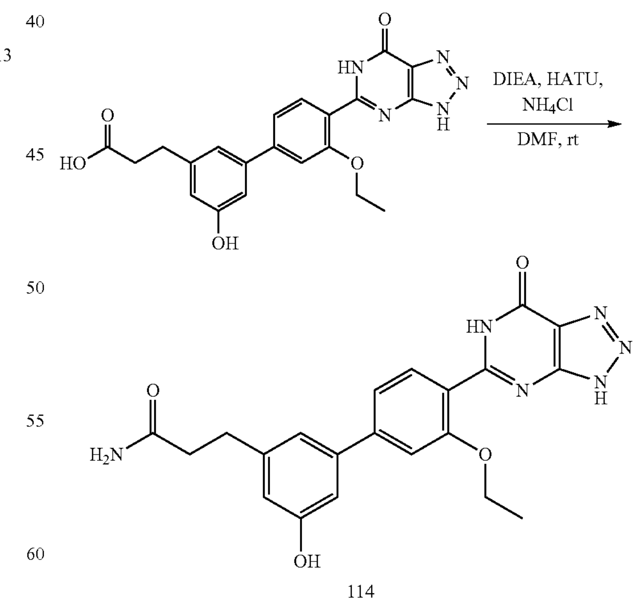

114

To a stirred solution of 3-(3'-ethoxy-5-hydroxy-4'-(7-oxo-6,7-dihydro-3H-[1,2,3]triazolo[4,5-d]pyrimidin-5-yl)-[1,1'-biphenyl]-3-yl)propanoic acid (10 mg, 0.024 mmol, 1.0 equiv) in DMF (1.0 mL) was added HATU (10.8 mg, 0.028 mmol, 1.2 equiv) and DIEA (4.6 mg, 0.036 mmol, 1.5 equiv) at rt. To the above mixture was added $NH_4Cl$ (1.9 mg, 0.036 mmol, 1.5 equiv) and the mixture was stirred for additional 5 h at rt. The mixture was purified by preparative HPLC to afford 3-(3'-ethoxy-5-hydroxy-4'-(7-oxo-6,7-dihydro-3H-[1,2,3]triazolo[4,5-d]pyrimidin-5-yl)-[1,1'-biphenyl]-3-yl)propanamide (3.1 mg, 29%) as a white solid. LCMS (ESI) =421.2 $[M+H]^+$. $^1H$ NMR (300 MHz, DMSO-$d_6$) δ 11.2 (broad s, 1H), 9.50 (broad s, 1H), 7.97 (d, J=8.0 Hz, 1H), 7.35-7.25 (m, 3H), 7.03 (s, 1H), 6.92 (s, 1H), 6.77 (broad s, 1H), 6.67 (s, 1H), 4.29 (q, J=6.9 Hz, 2H), 2.80 (t, J=7.5 Hz, 2H), 2.40 (t, J=7.5 Hz, 2H), 1.39 (t, J=6.9 Hz, 3H).

Example 15: Synthesis of 3-(5-(2-aminoethoxy)-3'-ethoxy-4'-(7-oxo-6,7-dihydro-3H-[1,2,3]triazolo[4,5-d]pyrimidin-5-yl)-[1,1'-biphenyl]-3-yl)propanoic acid (Compound 115)

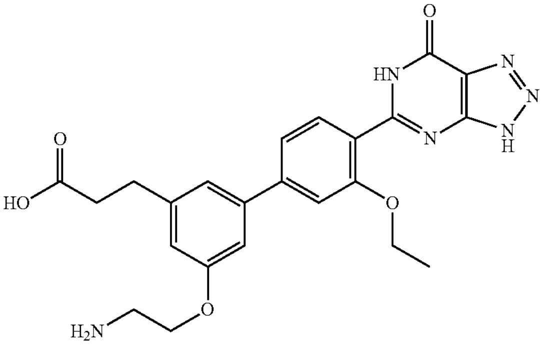

115

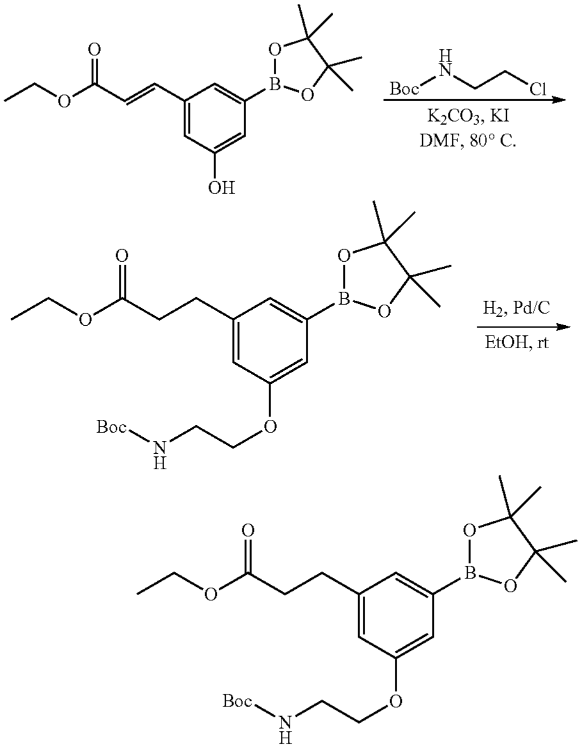

Step 1: To a solution of ethyl (E)-3-(3-hydroxy-5-(4,4,5,5-tetramethyl-1,3,2-dioxaborolan-2-yl)phenyl)acrylate (150 mg, 0.471 mmol, 1.0 equiv) and tert-butyl N-(2-chloroethyl) carbamate (101 mg, 0.566 mmol, 1.2 equiv) in DMF (2.0 mL) was added $K_2CO_3$ (130 mg, 0.943 mmol, 2.0 equiv) and KI (15.6 mg, 0.094 mmol, 0.20 equiv) at room temperature. The resulting mixture was stirred for 8 h at 80° C., then allowed to cool to room temperature. The mixture was diluted with water (20 mL) and extracted with EA (2×10 mL). The combined organic layers were washed with brine (10 mL), dried over anhydrous $Na_2SO_4$, filtered, and concentrated under reduced pressure. The residue was purified by silica gel column chromatography, eluted with EA:PE (1:3) to afford ethyl (E)-3-(3-(2-((tert-butoxycarbonyl)amino)ethoxy)-5-(4,4,5,5-tetramethyl-1,3,2-dioxaborolan-2-yl)phenyl)acrylate (250 mg) as a yellow solid, carried on directly into the next step.

Step 2: To a solution of ethyl (E)-3-(3-(2-((tert-butoxycarbonyl)amino)ethoxy)-5-(4,4,5,5-tetramethyl-1,3,2-dioxaborolan-2-yl)phenyl)acrylate (250 mg from the previous reaction) in 10 mL MeOH was added Pd/C (10%, 0.025 g) under nitrogen atmosphere. The mixture was hydrogenated at room temperature for 16 h under hydrogen atmosphere balloon, filtered through a Celite pad and concentrated under reduced pressure to afford ethyl 3-(3-(2-((tert-butoxycarbonyl)amino)ethoxy)-5-(4,4,5,5-tetramethyl-1,3,2-dioxaborolan-2-yl)phenyl)propanoate (150 mg, 69% over the two steps) as a yellow solid.

3-(5-(2-Aminoethoxy)-3'-ethoxy-4'-(7-oxo-6,7-dihydro-3H-[1,2,3]triazolo[4,5-d]pyrimidin-5-yl)-[1,1'-biphenyl]-3-yl)propanoic acid was prepared using the procedures in Example 12 and Example 8, Step 4 (TFA hydrolysis of N-Boc group). LCMS (ESI)=465.3 $[M+H]^+$. $^1H$ NMR (300 MHz, DMSO-$d_6$) δ 8.02 (d, J=8.4 Hz, 1H), 7.42-7.35 (m, 2H), 7.27 (s, 1H), 7.15 (s, 1H), 6.91 (s, 1H), 4.32 (d, J=6.9 Hz, 2H), 4.27-4.17 (m, 2H), 3.18 (s, 2H), 2.91 (t, J=7.6 Hz, 2H), 2.62 (t, J=7.6 Hz, 2H), 1.44 (t, J=6.9 Hz, 3H).

Example 16: Synthesis of 3-(4-(2-Aminoethoxy)-3'-ethoxy-4'-(7-oxo-6,7-dihydro-3H-[1,2,3]triazolo[4,5-d]pyrimidin-5-yl)-[1,1'-biphenyl]-3-yl)propanoic acid (Compound 116)

116

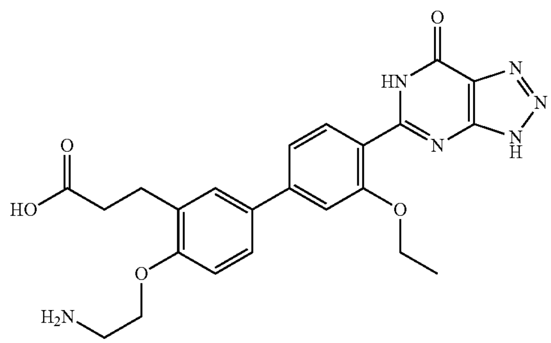

3-(4-(2-Aminoethoxy)-3'-ethoxy-4'-(7-oxo-6,7-dihydro-3H-[1,2,3]triazolo[4,5-d]pyrimidin-5-yl)-[1,1'-biphenyl]-3-yl)propanoic acid was prepared using the procedures in Example 15 starting from 5-bromo-2-hydroxybenzaldehyde. LCMS (ESI)=465.3 $[M+H]^+$. $^1H$ NMR (300 MHz, DMSO-$d_6$) δ 7.99 (d, J=8.5 Hz, 1H), 7.63 (s, 1H), 7.62-7.57 (m, 1H), 7.38-7.32 (m, 2H), 7.08 (d, J=8.5 Hz, 1H), 4.32 (q, J=6.9 Hz, 2H), 4.21 (t, J=5.0 Hz, 2H), 3.25 (d, J=5.3 Hz, 2H), 2.96 (t, J=7.2 Hz, 2H), 1.44 (t, J=6.9 Hz, 3H).

Example 17: Synthesis of 3-(3'-Ethoxy-4'-(7-oxo-6,7-dihydro-3H-[1,2,3]triazolo[4,5-d]pyrimidin-5-yl)-[1,1'-biphenyl]-3-yl)-N-hydroxypropanamide (Compound 117)

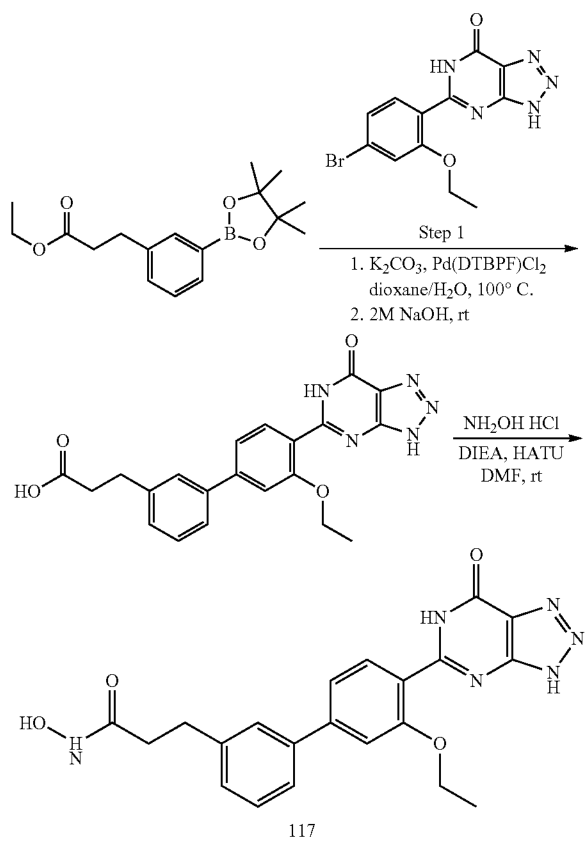

117

Step 1: Ethyl 3-(3-(4,4,5,5-tetramethyl-1,3,2-dioxaborolan-2-yl)phenyl)propanoate was prepared from ethyl (E)-3-(3-bromophenyl)acrylate using procedures in Example 12 and Example 13. To a solution of 5-(4-bromo-2-ethoxyphenyl)-3,6-dihydro-7H-[1,2,3]triazolo[4,5-d]pyrimidin-7-one (80.0 mg, 0.238 mmol, 1.0 equiv) and ethyl 3-(3-(4,4,5,5-tetramethyl-1,3,2-dioxaborolan-2-yl)phenyl)propanoate (86.9 mg, 0.286 mmol, 1.2 equiv) in dioxane (1.0 mL) and $H_2O$ (0.35 mL) was added $K_2CO_3$ (98.7 mg, 0.714 mmol, 3.0 equiv) and Pd(DTBPF)$Cl_2$ (15.5 mg, 0.024 mmol, 0.10 equiv). After stirring for 16 h at 100° C. under nitrogen, the mixture was allowed to cool to room temperature. 2M NaOH (0.48 mL, 0.96 mmol, 4.0 equiv) was added and the resulting mixture was stirred for 3 h. The resulting mixture was purified by reverse phase flash chromatography to afford 3-(3'-ethoxy-4'-(7-oxo-6,7-dihydro-3H-[1,2,3]triazolo[4,5-d]pyrimidin-5-yl)-[1,1'-biphenyl]-3-yl)propanoic acid (80 mg, 58%) as a yellow solid. LCMS (ESI)=406.2 $[M+H]^+$.

Step 2: To a stirred solution of 3-(3'-ethoxy-4'-(7-oxo-6,7-dihydro-3H-[1,2,3]triazolo[4,5-d]pyrimidin-5-yl)-[1,1'-biphenyl]-3-yl)propanoic acid (35 mg, 0.086 mmol, 1.0 equiv) and DIEA (33.5 mg, 0.259 mmol, 3.0 equiv) in DMF (1.0 mL) was added HATU (42.7 mg, 0.112 mmol, 1.3 equiv) at room temperature. To the above mixture was added hydroxylamine hydrochloride (12.0 mg, 0.173 mmol, 2.0 equiv) at room temperature, and the mixture was stirred for 16 h. The mixture was purified by preparative HPLC to afford 3-(3'-ethoxy-4'-(7-oxo-6,7-dihydro-3H-[1,2,3]triazolo[4,5-d]pyrimidin-5-yl)-[1,1'-biphenyl]-3-yl)-N-hydroxypropanamide (4.5 mg, 12%) as a white solid. LCMS (ESI)=421.2 $[M+H]^+$. $^1$H NMR (300 MHz, DMSO-$d_6$) δ 11.76 (broad s, 1H), 10.39 (s, 1H), 8.72 (s, 1H), 7.95 (d, J=8.4 Hz, 1H), 7.61 (s, 1H), 7.61-7.55 (m, 1H), 7.45-7.35 (m, 3H), 7.26 (d, J=7.8, 1H), 4.32 (q, J=6.9 Hz, 2H), 2.92 (t, J=7.5 Hz, 2H), 2.35 (t, J=7.5 Hz, 2H), 1.42 (t, J=6.9 Hz, 3H).

Example 18: Synthesis of 3-(3'-Ethoxy-4'-(7-oxo-6,7-dihydro-3H-[1,2,3]triazolo[4,5-d]pyrimidin-5-yl)-[1,1'-biphenyl]-3-yl)-N-methoxypropanamide (Compound 118)

118

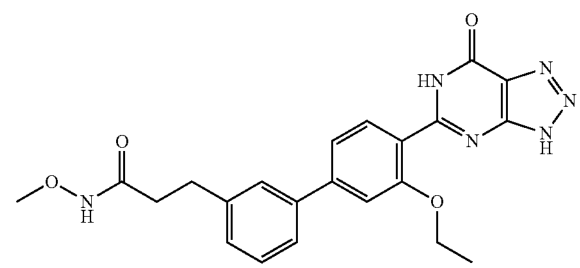

3-(3'-Ethoxy-4'-(7-oxo-6,7-dihydro-3H-[1,2,3]triazolo[4,5-d]pyrimidin-5-yl)-[1,1'-biphenyl]-3-yl)-N-methoxypropanamide was prepared using the procedures in Example 17 from O-methylhydroxylamine hydrochloride. LCMS (ESI)=435.2 $[M+H]^+$. $^1$H NMR (300 MHz, DMSO-$d_6$) δ 12.20 (s, 1H), 10.99 (s, 1H), 7.87 (d, J=7.1 Hz, 1H), 7.62 (s, 1H), 7.62-7.57 (m, 1H), 7.45-7.35 (m, 2H), 7.42 (s, 1H), d, J=7.5 Hz, 1H), 4.31 (q, J=6.9 Hz, 2H), 3.54 (s, 3H), 2.93 (t, J=7.4, 2H), 2.40-2.25 (m, 2H), 1.40 (t, J=6.9 Hz, 3H).

Example 19: Synthesis of 3-(3'-Ethoxy-4'-(7-oxo-6,7-dihydro-3H-[1,2,3]triazolo[4,5-d]pyrimidin-5-yl)-[1,1'-biphenyl]-3-yl)propanamide (Compound 119)

119

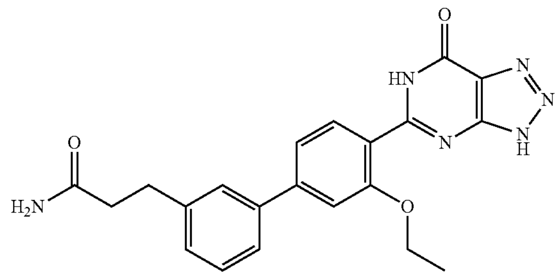

3-(3'-Ethoxy-4'-(7-oxo-6,7-dihydro-3H-[1,2,3]triazolo[4,5-d]pyrimidin-5-yl)-[1,1'-biphenyl]-3-yl)propanamide was prepared using the procedures in Example 17 from ammonium carbamate. LCMS (ESI)=405.2 $[M+H]^+$. $^1$H NMR (300 MHz, DMSO-$d_6$) δ 12.12 (s, 1H), 7.88 (d, J=8.3 Hz, 1H), 7.63 (s, 1H), 7.59 (d, J=7.6 Hz, 1H), 7.45-7.36 (m 3H), 7.31 (s, 1H), 7.28 (d, J=7.6 Hz, 1H), 6.79 (s, 1H), 4.31 (q, J=6.9 Hz, 2H), 2.91 (t, J=7.7 Hz, 2H), 2.44 (t, J=7.7 Hz, 2H), 1.40 (t, J=6.9 Hz, 3H).

Example 20: Synthesis of (Z)-5-((3'-Ethoxy-4'-(7-oxo-6,7-dihydro-3H-[1,2,3]triazolo[4,5-d]pyrimidin-5-yl)-[1,1'-biphenyl]-3-yl)methylene)thiazolidine-2,4-dione (Compound 120)

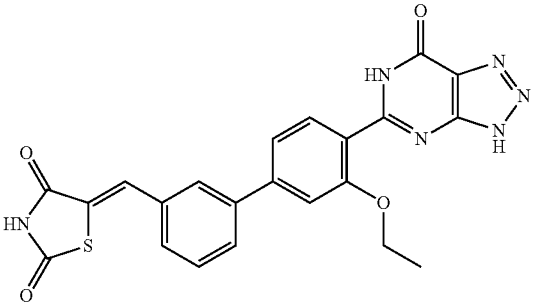

120

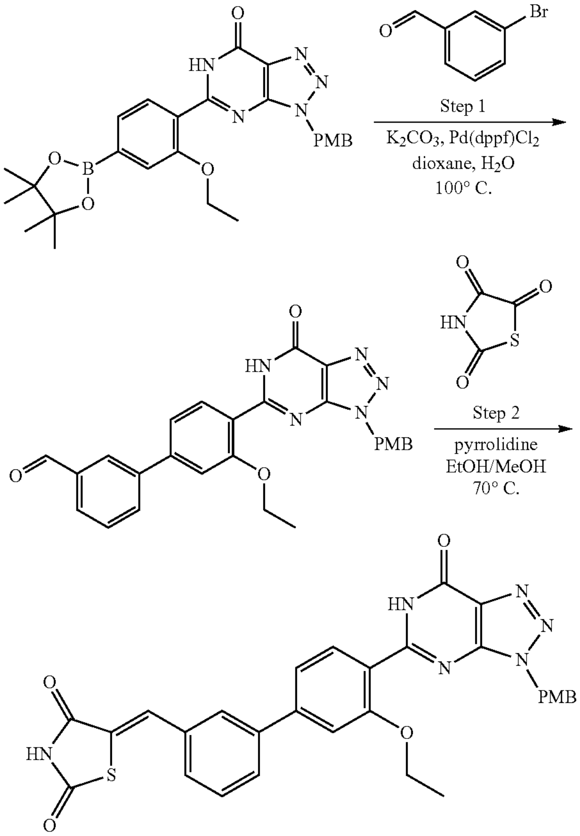

Step 1: To a solution of 5-(2-ethoxy-4-(4,4,5,5-tetramethyl-1,3,2-dioxaborolan-2-yl)phenyl)-3-(4-methoxybenzyl)-3,6-dihydro-7H-[1,2,3]triazolo[4,5-d]pyrimidin-7-one (150 mg, 0.298 mmol, 1.0 equiv) and 3-bromobenzaldehyde (66.2 mg, 0.358 mmol, 1.2 equiv) in dioxane (2.0 mL) and water (0.2 mL) was added $K_2CO_3$ (124 mg, 0.894 mmol, 3.0 equiv) and Pd(dppf)$Cl_2$ (21.8 mg, 0.030 mmol, 0.10 equiv). After stirring for 2 h at 100° C. under nitrogen, the resulting mixture was concentrated under reduced pressure. The residue was purified by silica gel column chromatography, eluted with EA/PE (0-100%) to afford 3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-carbaldehyde (110 mg, 64.1%) as a yellow solid. LCMS (ESI)=482.1 $[M+H]^+$.

Step 2: To a solution of 3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-carbaldehyde (110 mg, 0.228 mmol, 1.0 equiv) and 2,4-thiazolidinedione (32.1 mg, 0.274 mmol, 1.2 equiv) in EtOH (1.0 mL) and MeOH (1.0 mL) was added pyrrolidine (32.5 mg, 0.457 mmol, 2.0 equiv) in portions at rt. The resulting mixture was stirred for 1.5 h at 70° C. The mixture was allowed to cool to rt and concentrated under reduced pressure. The residue was purified by silica gel column chromatography, eluted with EA/PE (0-100%) to afford ((Z)-5-((3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)methylene)thiazolidine-2,4-dione (110 mg, 58.1%) as a yellow solid. LCMS (ESI)=581.3 $[M+H]^+$.

(Z)-5-((3'-Ethoxy-4'-(7-oxo-6,7-dihydro-3H-[1,2,3]triazolo[4,5-d]pyrimidin-5-yl)-[1,1'-biphenyl]-3-yl)methylene)thiazolidine-2,4-dione was prepared using the procedures in Example 4, Step 6. LCMS (ESI)=459.1 $[M-H]^+$. $^1H$ NMR (300 MHz, DMSO-$d_6$) δ 12.1 (s, 1H), 7.99 (s, 1H), 7.90 (d, J=8.0 Hz, 1H), 7.84-7.76 (m, 1H), 7.67 (s, 1H), 7.65-7.60 (m, 2H), 7.61 (s, 1H), 7.48 (s, 1H), 7.46 (d, J=8.0 Hz, 1H), 4.31 (q, J=7.0 Hz, 2H), 1.40 (t, J=6.9 Hz, 3H).

Example 21: Synthesis of 5-((3'-Ethoxy-4'-(7-oxo-6,7-dihydro-3H-[1,2,3]triazolo[4,5-d]pyrimidin-5-yl)-[1,1'-biphenyl]-3-yl)methyl)thiazolidine-2,4-dione (Compound 121)

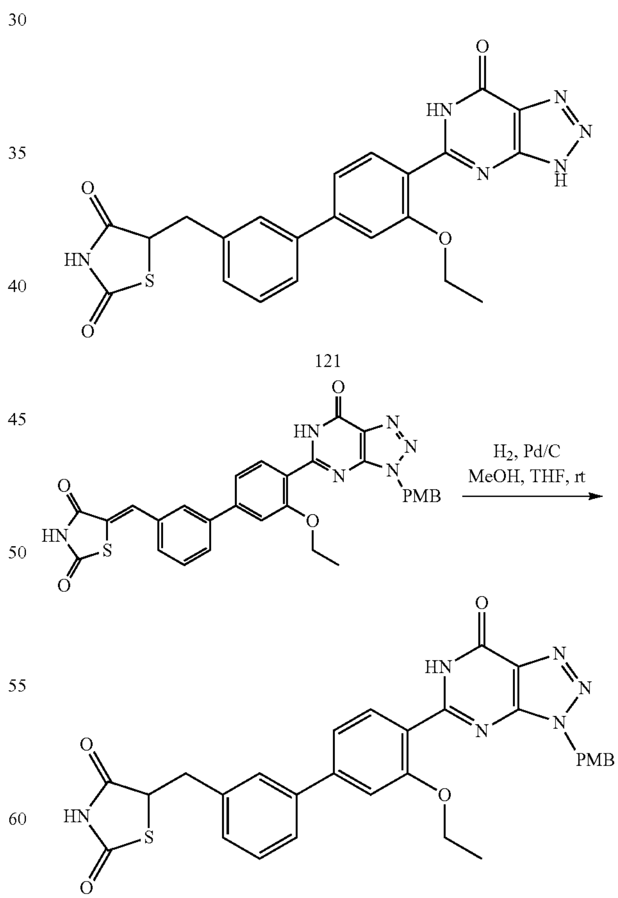

121

To a solution of ((Z)-5-((3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)methylene)thiazolidine-2,4-dione (80.0 mg, 0.138 mmol, 1.0 equiv) in 20 mL MeOH and 40 mL THF was added Pd/C (10%, 40 mg) under nitrogen atmosphere. The mixture was hydrogenated at room temperature for 24 hours using a hydrogen balloon, then filtered through a Celite pad and concentrated under reduced pressure. The residue was purified by silica gel column chromatography, eluted with EA/PE (0-100%) to afford 5-((3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)methyl)thiazolidine-2,4-dione (60 mg, 72%) as a white solid. LCMS (ESI)=583.3 [M+H]$^+$.

5-((3'-Ethoxy-4'-(7-oxo-6,7-dihydro-3H-[1,2,3]triazolo[4,5-d]pyrimidin-5-yl)-[1,1'-biphenyl]-3-yl)methyl)thiazolidine-2,4-dione was prepared using the procedures in Example 4, Step 6. LCMS (ESI)=463.1 [M+H]$^+$. $^1$H NMR (300 MHz, DMSO-$d_6$) δ 7.94 (d, J=8.2 Hz, 1H), 7.72-7.64 (m, 2H), 7.51-7.36 (m, 3H), 7.31 (d, J=7.6 Hz, 1H), 4.95 (dd, J=9.4, 4.3 Hz, 1H), 4.32 (q, J=6.8 Hz, 2H), 3.51 (dd, J=14.0, 4.4 Hz, 1H), 3.19 (dd, J=13.9, 9.4 Hz, 1H), 1.42 (t, J=6.9 Hz, 3H).

Example 22: Synthesis of 3-(2-(3'-Ethoxy-4'-(7-oxo-6,7-dihydro-3H-[1,2,3]triazolo[4,5-d]pyrimidin-5-yl)-[1,1'-biphenyl]-3-yl)ethyl)-1,2,4-oxadiazol-5(4H)-one (Compound 122)

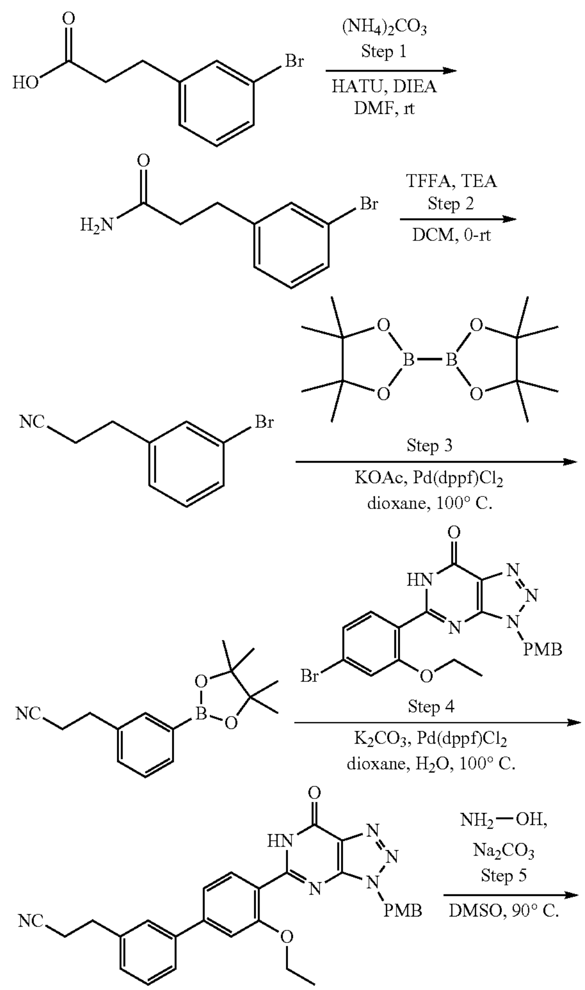

-continued

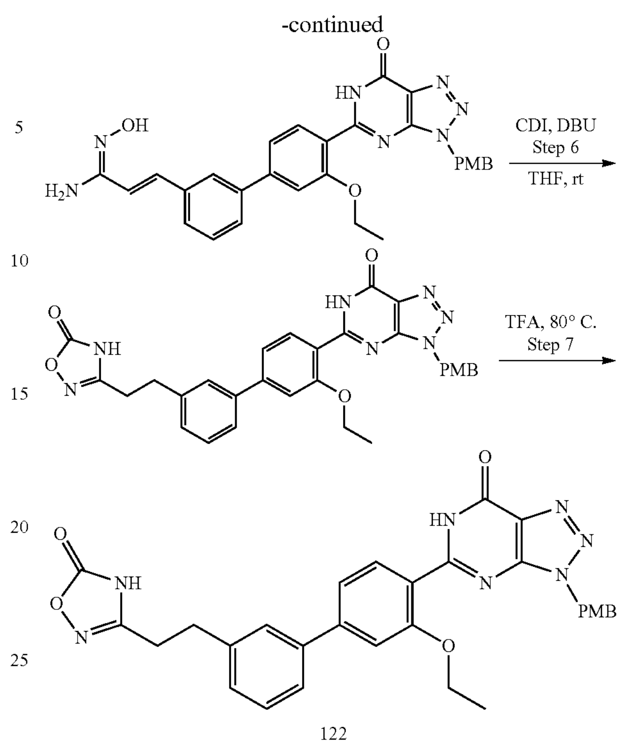

122

Step 1: To a stirred solution of 3-(3-bromophenyl)propanoic acid (1.00 g, 4.36 mmol, 1.0 equiv) and HATU (2.49 g, 6.55 mmol, 1.5 equiv) in DMF (10 mL) was added DIEA (0.85 g, 6.58 mmol, 1.5 equiv) at rt. The resulting mixture was stirred for 1 h. To the above mixture was added $(NH_4)_2CO_3$ (0.84 g, 8.73 mmol, 2.0 equiv) in portions at rt. The mixture was stirred for additional 12 h at rt. The resulting mixture was diluted with water (20 mL) and extracted with EA (3×40 mL). The combined organic layers were washed with brine (20 mL), dried over anhydrous $Na_2SO_4$, filtered, and concentrated under reduced pressure. The residue was purified by silica gel column chromatography, eluted with EA/PE (0-100%) to afford 3-(3-bromophenyl)propanamide (800 mg, 35.1%) as a yellow oil.

Step 2: To a stirred solution of 3-(3-bromophenyl)propanamide (800 mg, 3.51 mmol, 1.0 equiv) in DCM (10 mL) was added TEA (710 mg, 7.02 mmol, 2.0 equiv) and trifluoroacetic anhydride (1.47 g, 7.02 mmol, 2.0 equiv) in portions at 0° C. The resulting mixture was allowed to warm to rt then stirred for 3 h. The mixture was concentrated under vacuum and the residue purified by silica gel column chromatography, eluted with EA/PE (0-10%) to afford 3-(3-bromophenyl)propanenitrile (500 mg, 67.9%) as a yellow oil. $^1$H NMR (300 MHz, $CDCl_3$) δ 7.48-7.38 (m, 2H), 7.30-7.18 (m, 2H), 2.96 (t, J=7.5 Hz, 2H), 2.70-2.60 (m, 2H).

Step 3: To a solution of 3-(3-bromophenyl)propanenitrile (300 mg, 1.43 mmol, 1.0 equiv) and bis(pinacolato)diboron (435 mg, 1.71 mmol, 1.2 equiv) in dioxane (3.0 mL) were added KOAc (280 mg, 2.86 mmol, 2.0 equiv) and Pd(dppf)$Cl_2$ (104 mg, 0.143 mmol, 0.10 equiv). After stirring for 3 h at 100° C. under nitrogen, the mixture was concentrated under reduced pressure. The residue was purified by silica gel column chromatography, eluted with EA/PE (0-10%) to afford 3-(3-(4,4,5,5-tetramethyl-1,3,2-dioxaborolan-2-yl)phenyl)propanenitrile (280 mg, 64.8%) as a yellow oil.

Step 4: To a solution of 5-(4-bromo-2-ethoxyphenyl)-3-(4-methoxybenzyl)-3,6-dihydro-7H-[1,2,3]triazolo[4,5-d]pyrimidin-7-one (200 mg, 0.438 mmol, 1.0 equiv) and 3-(3-(4,4,5,5-tetramethyl-1,3,2-dioxaborolan-2-yl)phenyl)propanenitrile (135 mg, 0.526 mmol, 1.2 equiv) in dioxane (2.0 mL) and water (0.20 mL) was added $K_2CO_3$ (182 mg, 1.32 mmol, 3.0 equiv) and $Pd(dppf)Cl_2$ (32 mg, 0.044 mmol, 0.1 equiv). After stirring for 2 h at 100° C. under nitrogen, the resulting mixture was concentrated under reduced pressure. The residue was purified by silica gel column chromatography, eluted with EA/PE (0-100%) to afford 3-(3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)propanenitrile (160 mg, 57.5%) as a white solid. LCMS (ESI)=507.2 $[M+H]^+$.

Step 5: A solution of 3-(3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)propanenitrile (150 mg, 0.296 mmol, 1.0 equiv) and $NH_2OH.H_2O$ (152 mg, 2.96 mmol, 10 equiv) in EtOH (10 mL) was stirred for 24 h at 75° C. The resulting mixture was concentrated under reduced pressure. This resulted in 3-(3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)-N'-hydroxypropanimidamide (145 mg, 43.6%) as a white solid. LCMS (ESI)=540.5 $[M+H]^+$.

Step 6: A solution of 3-(3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)-N'-hydroxypropanimidamide (145 mg, 0.269 mmol, 1.0 equiv) and CDI (65.4 mg, 0.403 mmol, 1.5 equiv) and DBU (61.4 mg, 0.403 mmol, 1.5 equiv) in THF (4.0 mL) was stirred for 2 h at rt. The resulting mixture was concentrated under vacuum. The residue was purified by silica gel column chromatography, eluted with DCM/MeOH (0-20%) to afford 3-(2-(3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)ethyl)-1,2,4-oxadiazol-5(4H)-one (80 mg, 26%) as a white solid.

Step 7: A solution of 3-(2-(3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)ethyl)-1,2,4-oxadiazol-5(4H)-one (80 mg, 0.14 mmol, 1.0 equiv) in TFA (2.0 mL) was stirred for 2 h at 80° C. The resulting mixture was concentrated under reduced pressure. The mixture was purified by preparative HPLC to afford 3-(2-(3'-ethoxy-4'-(7-oxo-6,7-dihydro-3H-[1,2,3]triazolo[4,5-d]pyrimidin-5-yl)-[1,1'-biphenyl]-3-yl)ethyl)-1,2,4-oxadiazol-5(4H)-one (0.7 mg, 1.1%) as a white solid. LCMS (ESI)=446.2 $[M+H]^+$. $^1$H NMR (300 MHz, $CD_3OD$) δ 8.23 (d, J=8.5 Hz, 1H), 7.63-7.59 (m, 1H), 7.59 (s, 1H), 7.50-7.43 (m, 2H), 7.40 (s, 1H), 7.32 (d, J=7.9 Hz, 1H), 4.42 (d, J=6.9 Hz, 2H), 3.12-3.05 (m, 2H), 2.91 (t, J=7.7 Hz, 2H), 1.59 (t, J=6.9 Hz, 3H).

Example 23: Synthesis of N—(N,N-Dimethylsulfamoyl)-3-(3'-ethoxy-4'-(7-oxo-6,7-dihydro-3H-[1,2,3]triazolo[4,5-d]pyrimidin-5-yl)-[1,1'-biphenyl]-3-yl)propanamide (Compound 123)

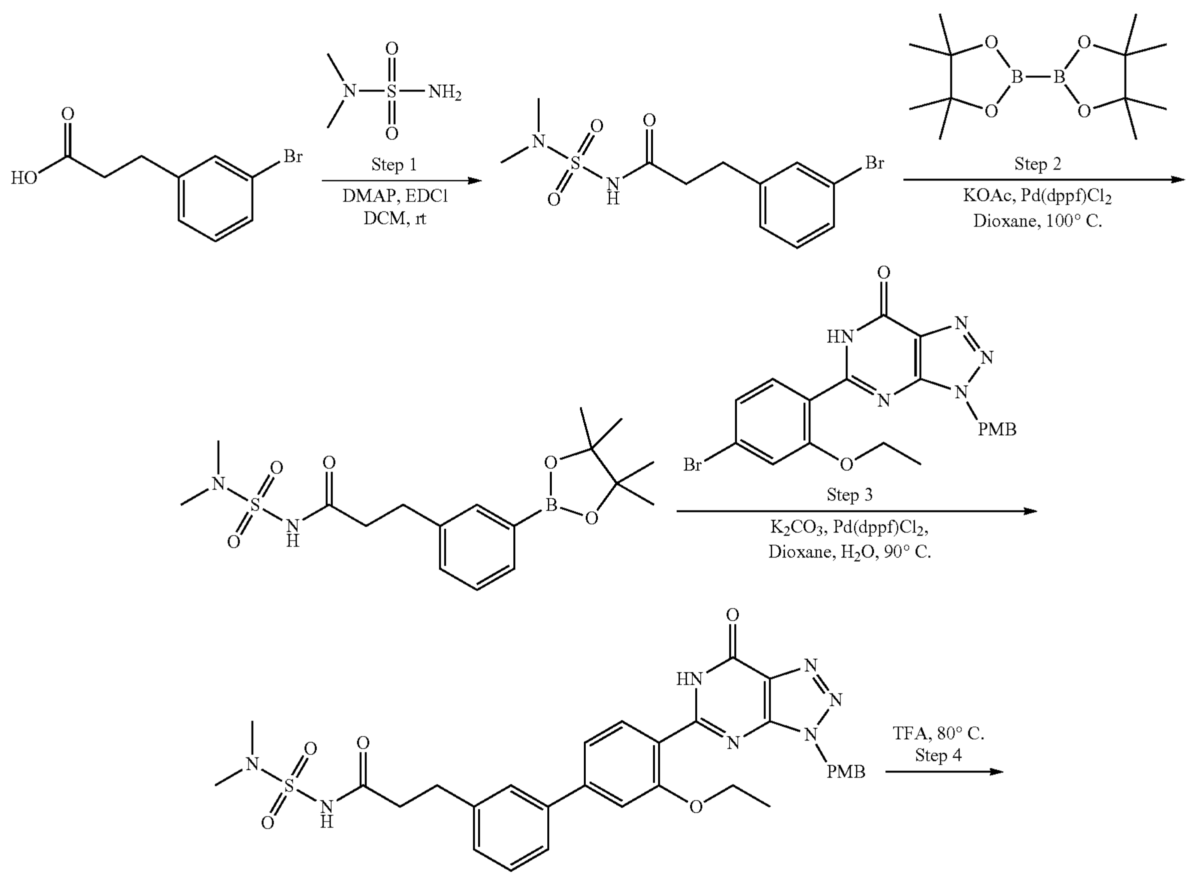

-continued

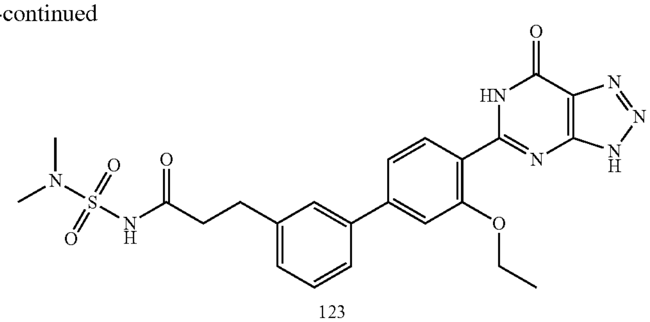

123

Step 1: To a stirred solution of 3-(3-bromophenyl)propanoic acid (500 mg, 2.18 mmol, 1.0 equiv) and dimethyl (sulfamoyl)amine (406 mg, 3.27 mmol, 1.5 equiv) in DCM (5.0 mL) was added DMAP (400 mg, 3.27 mmol, 1.5 equiv) and EDCI (628 mg, 3.27 mmol, 1.5 equiv) at room temperature under nitrogen. The resulting mixture was stirred for 16 h. The reaction was quenched by the addition of water (20 mL) and extracted with DCM (2×10 mL). The combined organic layers were washed with brine (10 mL), dried over anhydrous $Na_2SO_4$, filtered, and concentrated under reduced pressure. This resulted in 3-(3-bromophenyl)-N—(N,N-dimethylsulfamoyl)propanamide (800 mg, crude) as an off-white solid.

Step 2: To a solution of 3-(3-bromophenyl)-N—(N,N-dimethylsulfamoyl)propanamide (800 mg, 2.39 mmol, 1.0 equiv) and bis(pinacolato)diboron (909 mg, 3.58 mmol, 1.5 equiv) in dioxane (10 mL) was added KOAc (703 mg, 7.16 mmol, 3.0 equiv) and Pd(dppf)$Cl_2$-DCM (195 mg, 0.239 mmol, 0.10 equiv). After stirring for 3 h at 100° C. under nitrogen, the resulting mixture was concentrated under reduced pressure. The residue was purified by silica gel column chromatography, eluted with EA:PE (1:3) to afford N—(N,N-dimethylsulfamoyl)-3-(3-(4,4,5,5-tetramethyl-1,3,2-dioxaborolan-2-yl)phenyl)propanamide (650 mg, 71.2%) as a yellow oil.

Step 3: To a solution of 5-(4-bromo-2-ethoxyphenyl)-3-(4-methoxybenzyl)-3,6-dihydro-7H-[1,2,3]triazolo[4,5-d]pyrimidin-7-one (50.0 mg, 0.110 mmol, 1.0 equiv) and N—(N,N-dimethylsulfamoyl)-3-(3-(4,4,5,5-tetramethyl-1,3,2-dioxaborolan-2-yl)phenyl)propanamide (54.5 mg, 0.142 mmol, 1.3 equiv) in dioxane (1.0 mL) and water (0.10 mL) was added $K_2CO_3$ (37.9 mg, 0.274 mmol, 2.5 equiv) and Pd(dppf)$Cl_2$-DCM (8.9 mg, 0.011 mmol, 0.10 equiv). After stirring for 3 h at 90° C. under nitrogen, the resulting mixture was allowed to cool to room temperature. The mixture was purified by silica gel column chromatography, eluted with EA:PE (0-100%) to afford N—(N,N-dimethylsulfamoyl)-3-(3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)propanamide (45 mg, 65%) as an off-white solid.

Step 4: A solution of N—(N,N-dimethylsulfamoyl)-3-(3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)propanamide (45.0 mg, 0.071 mmol, 1.0 equiv) in TFA (1.0 mL) was stirred for 2 h at 80° C. The mixture was concentrated under reduced pressure and purified by preparative HPLC to afford N—(N,N-dimethylsulfamoyl)-3-(3'-ethoxy-4'-(7-oxo-6,7-dihydro-3H-[1,2,3]triazolo[4,5-d]pyrimidin-5-yl)-[1,1'-biphenyl]-3-yl)propanamide (12 mg, 33%) as a white solid. LCMS (ESI)=512.2 $[M+H]^+$. $^1H$ NMR (300 MHz, DMSO-$d_6$) δ 12.04 (broad s, 1H), 7.90 (d, J=8.4 Hz, 1H), 7.67-7.58 (m, 2H), 7.47-7.37 (m, 3H), 7.29 (d, J=8.0 Hz, 1H), 4.31 (q, J=6.9 Hz, 2H), 2.94 (t, J=7.5 Hz, 2H), 2.72 (s, 6H), 2.66 (t, J=7.5 Hz, 2H), 1.41 (t, J=6.9 Hz, 3H).

Example 24: Synthesis of 5-(3'-(2-(1H-Tetrazol-5-yl)ethyl)-3-ethoxy-[1,1'-biphenyl]-4-yl)-3,6-dihydro-7H-[1,2,3]triazolo[4,5-d]pyrimidin-7-one (Compound 124)

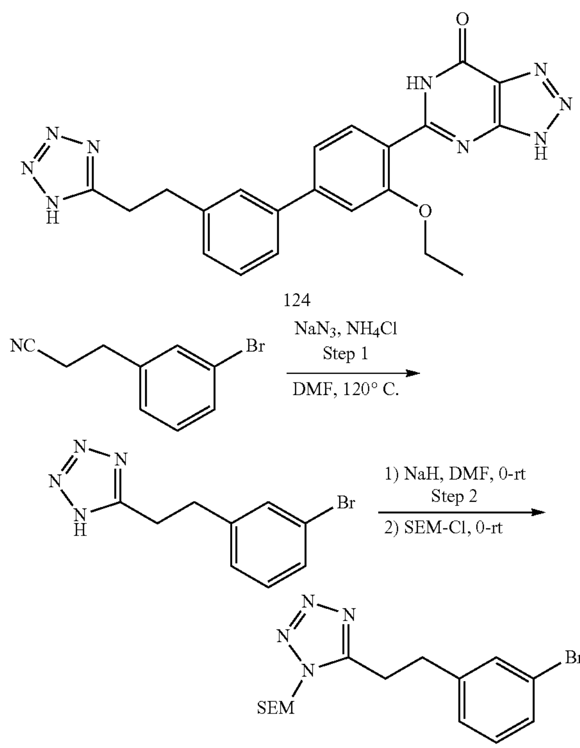

124

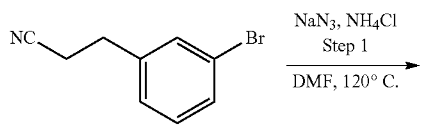

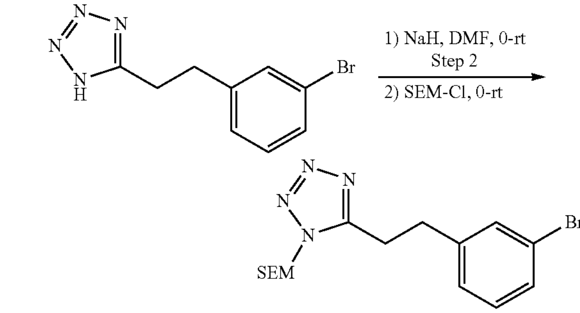

Step 1: A solution of 3-(3-bromophenyl)propanenitrile (200 mg, 0.952 mmol, 1.0 equiv) and $NH_4Cl$ (153 mg, 2.85 mmol, 3.0 equiv) and $NaN_3$ (186 mg, 2.86 mmol, 3.0 equiv) in DMF (5.0 mL) was stirred for 24 h at 120° C. The mixture was concentrated under reduced pressure and the residue purified by reverse phase flash chromatography to afford 5-(3-bromophenethyl)-1H-tetrazole (150 mg, 70%) as a yellow solid.

Step 2: To a stirred solution of 5-(3-bromophenethyl)-1H-tetrazole (150 mg, 0.593 mmol, 1.0 equiv) in DMF (5.0 mL) was added NaH (21.3 mg, 0.889 mmol, 1.5 equiv) dropwise at 0° C. The resulting mixture was allowed to warm to rt and was stirred for 1 h. The mixture was cooled to 0° C., then SEM-Cl (148 mg, 0.889 mmol, 1.5 equiv) was added dropwise at 0° C. The resulting mixture was allowed to warm to rt and stirred for 12 h. The reaction was quenched by the addition of water (20 mL) and the mixture was extracted with EA (2×20 mL). The combined organic layers were washed with brine (20 mL), dried over anhydrous $Na_2SO_4$, filtered, and concentrated under reduced pressure. The residue was purified by silica gel column chromatography, eluted with EA/PE (0-20%) to afford 5-(3-bromophenethyl)-1-((2-(trimethylsilyl)ethoxy)methyl)-1H-tetrazole (200 mg, 81.0%) as a yellow oil.

5-(3'-(2-(1H-Tetrazol-5-yl)ethyl)-3-ethoxy-[1,1'-biphenyl]-4-yl)-3,6-dihydro-7H-[1,2,3]triazolo[4,5-d]pyrimidin-7-one was prepared using the procedures in Example 23. LCMS (ESI)=430.2 $[M+H]^+$. $^1H$ NMR (300 MHz, DMSO-$d_6$) δ 7.91 (d, J=8.3 Hz, 1H), 7.62 (s, 1H), 7.62-7.56 (m, 1H), 7.45-7.38 (m, 2H), 7.37 (s, 1H), 7.28 (d, J=7.5 Hz, 1H), 4.32 (q, J=6.9 Hz, 2H), 3.30-3.20 (m, 2H), 3.20-3.10 (m, 2H), 1.42 (t, J=6.9 Hz, 3H).

Example 25: Synthesis of 5-((3'-Ethoxy-4'-(7-oxo-6,7-dihydro-3H-[1,2,3]triazolo[4,5-d]pyrimidin-5-yl)-[1,1'-biphenyl]-3-yl)methyl)oxazolidine-2,4-dione (Compound 125)

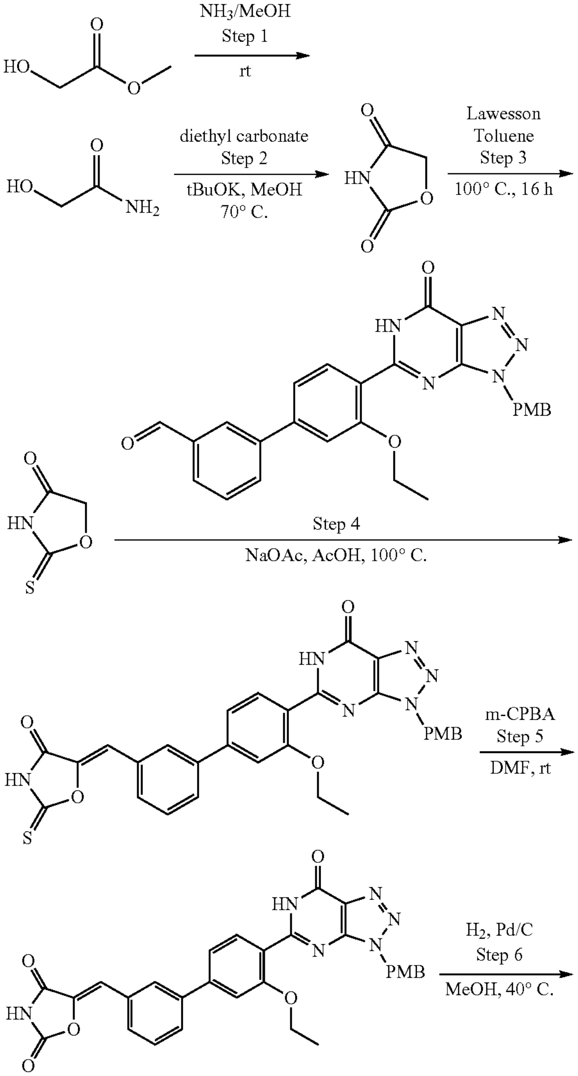

-continued

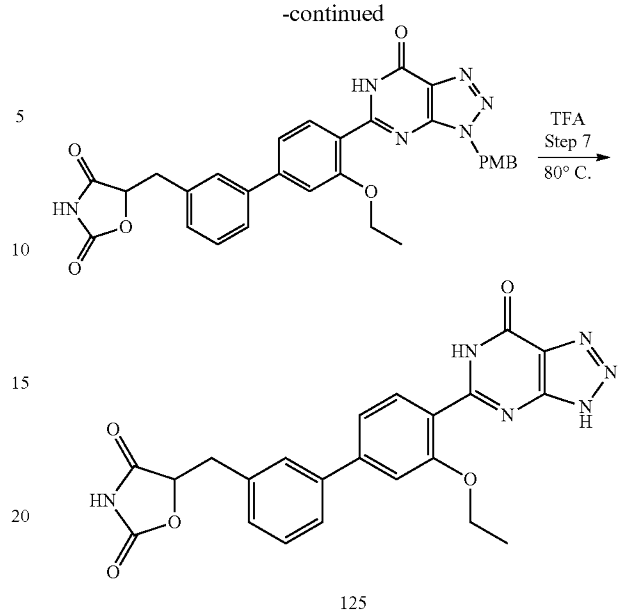

125

Step 1: A solution of methyl 2-hydroxyacetate (1.00 g, 11.1 mmol, 1.0 equiv) in a saturated solution of $NH_3$(g) in MeOH (10 mL) was stirred for 16 h at room temperature. The resulting mixture was concentrated under reduced pressure. This resulted in glycolamide (1 g, crude) as a white solid. $^1H$ NMR (300 MHz, DMSO-$d_6$) δ 7.17 (broad s, 2H), 5.43 (broad s, 2H), 3.73 (s, 2H).

Step 2: To a stirred solution of glycolamide (1.0 g crude, 1.0 equiv) and diethyl carbonate (2.00 mL, 2.05 g, 17.4 mmol) in MeOH (10 mL) was added t-BuOK (1.80 g, 16.0 mmol) at room temperature under a nitrogen. The resulting mixture was stirred for 16 h at 70° C. The mixture was allowed to cool to room temperature and was concentrated under reduced pressure. The residue was dissolved in water (50 mL). The mixture was acidified to pH 3-4 with conc. HCl and was extracted with EA (2×20 mL). The combined organic layers were washed with brine (20 mL), dried over anhydrous $Na_2SO_4$, filtered and concentrated under reduced pressure. The residue was purified by silica gel column chromatography, eluted with EA:PE (1:1) to afford oxazolidine-2,4-dione (330 mg, 29.4% for the two steps) as a white solid. $^1H$ NMR (300 MHz, DMSO-$d_6$) δ 11.81 (broad s, 1H), 4.76 (s, 2H).

Step 3: A solution of oxazolidine-2,4-dione (210 mg, 2.08 mmol, 1.0 equiv) and 2,4-bis(4-methoxyphenyl)-2,4-dithioxo-1,3,2,4-dithiadiphosphetane (Lawesson reagent, 504 mg, 1.25 mmol, 0.60 equiv) in toluene (3.0 mL) was stirred for 16 h at 100° C. The mixture was allowed to cool to room temperature and the resulting mixture was concentrated under reduced pressure. The residue was purified by silica gel column chromatography, eluted with EA:PE (1:10) to afford 2-thioxooxazolidin-4-one (200 mg, 82.2%) as a yellow solid. $^1H$ NMR (300 MHz, DMSO-$d_6$) δ 13.42 (broad s, 1H), 5.09 (s, 2H).

Step 4: To a stirred solution of 3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-carbaldehyde (105 mg, 0.218 mmol, 1.0 equiv) and 2-thioxooxazolidin-4-one (38.3 mg, 0.327 mmol, 1.5 equiv) in AcOH (1.0 mL) was added NaOAc (53.7 mg, 0.654 mmol, 3.0 equiv) at room temperature. The mixture was stirred for 16 h at 100° C., then allowed to cool to room temperature. The resulting mixture was diluted with water (5 mL) and the precipitated solids were collected by filtration and washed with water (3×2 mL). The resulting solid was dried by a heat lamp to afford (Z)-5-((3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)methylene)-2-thioxooxazolidin-4-one (110 mg, crude) as a yellow solid.

Step 5: A solution of (Z)-5-((3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)methylene)-2-thioxooxazolidin-4-one (110 mg, 0.189 mmol, 1.0 equiv) and m-CPBA (98.1 mg, 0.568 mmol, 3.0 equiv) in DMF (1.5 mL) was stirred for 2 h at room temperature. The resulting mixture was diluted with water (5 mL). The precipitated solids were collected by filtration and washed with water (3×1 mL). The resulting solid was dried under a heat lamp to afford (Z)-5-((3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)methylene)oxazolidine-2,4-dione (40 mg, 37%) as a yellow solid.

Step 6: To a solution of (Z)-5-((3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)methylene)oxazolidine-2,4-dione (40 mg, 0.071 mmol, 1.0 equiv) in 10 mL MeOH was added Pd/C (10%, 10 mg) under nitrogen atmosphere. The mixture was hydrogenated for 5 h at 40° C. under hydrogen atmosphere (balloon), filtered through a Celite pad and concentrated under reduced pressure. This resulted in 5-((3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)methyl)oxazolidine-2,4-dione (33 mg, 82.2%) as an off-white solid.

Step 7: A solution of 5-((3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)methyl)oxazolidine-2,4-dione (33 mg, 0.058 mmol, 1.0 equiv) in TFA (1.0 mL) was stirred for 2 h at 80° C. The mixture was allowed to cool to room temperature. The resulting mixture was concentrated under reduced pressure and the residue was purified by preparative HPLC to afford 5-((3'-ethoxy-4'-(7-oxo-6,7-dihydro-3H-[1,2,3]triazolo[4,5-d]pyrimidin-5-yl)-[1,1'-biphenyl]-3-yl)methyl)oxazolidine-2,4-dione (6 mg, 23%) as a white solid. LCMS (ESI)=447.2 $[M+H]^+$. $^1$H NMR (300 MHz, DMSO-$d_6$) δ 11.89 (broad s, 1H), 11.89 (broad s, 1H), 7.91 (d, J=7.9 Hz, 1H), 7.72-7.63 (m, 2H), 7.46 (t, J=7.6, 1H), 7.40 (s, 1H), 7.40-7.35 (m, 1H), 7.29 (d, J=7.6 Hz, 1H), 5.34 (dd, J=6.8, 4.3 Hz, 1H), 4.31 (q, J=6.9 Hz, 2H), 3.23-3.13 (m, 2H), 1.41 (t, J=6.9 Hz, 3H).

Example 26: Synthesis of 4-((3'-Ethoxy-4'-(7-oxo-6,7-dihydro-3H-[1,2,3]triazolo[4,5-d]pyrimidin-5-yl)-[1,1'-biphenyl]-3-yl)methyl)-3-methylisoxazol-5(2H)-one (Compound 126)

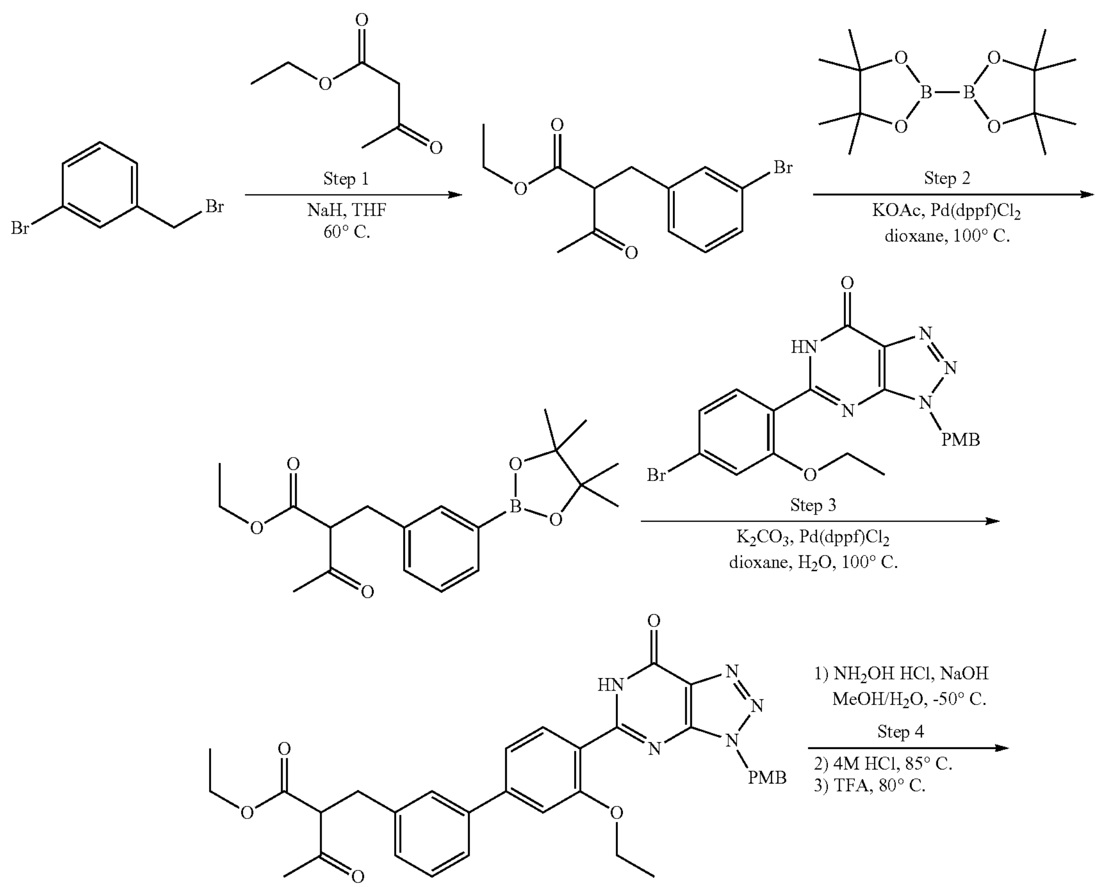

-continued

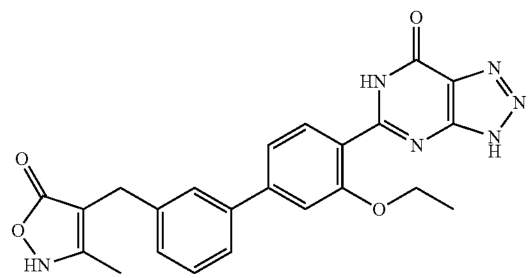

126

Step 1: To a stirred solution of ethyl acetoacetate (10.0 g, 76.8 mmol, 1.0 equiv) in THF (100 mL) was added NaH (3.07 g, 76.8 mmol, 1.0 equiv, 60%) in portions at room temperature under nitrogen. The mixture was stirred for 10 min then 1-bromo-3-(bromomethyl)benzene (15.4 g, 61.5 mmol, 0.80 equiv) was added. The resulting mixture was stirred for 16 h at 60° C. The mixture was allowed to cool to room temperature. The reaction was quenched by the addition of water (100 mL) and the mixture was acidified to pH 4-5 with conc. HCl. The resulting mixture was extracted with EA (2×30 mL). The combined organic layers were washed with brine (50 mL), dried over anhydrous $Na_2SO_4$, filtered, and concentrated under reduced pressure. The residue was purified by silica gel column chromatography, eluted with EA:PE (1:10) to afford ethyl 2-(3-bromobenzyl)-3-oxobutanoate (7 g, 30%) as a colorless liquid.

Step 2: To a solution of ethyl 2-(3-bromobenzyl)-3-oxobutanoate (1.00 g, 3.34 mmol, 1.0 equiv) and bis(pinacolato)diboron (1.27 g, 5.01 mmol, 1.5 equiv) in dioxane (10 mL) was added KOAc (0.66 g, 6.68 mmol, 2.0 equiv) and $Pd(dppf)Cl_2$-DCM (0.27 g, 0.33 mmol, 0.10 equiv). After stirring for 2 h at 100° C. under nitrogen, the resulting mixture was concentrated under reduced pressure. The residue was purified by silica gel column chromatography, eluted with EA/PE (0-10%) to afford ethyl 3-oxo-2-(3-(4,4,5,5-tetramethyl-1,3,2-dioxaborolan-2-yl)benzyl)butanoate (600 mg, 51.8%) as a colorless semi-solid.

Step 3: To a solution of 5-(4-bromo-2-ethoxyphenyl)-3-(4-methoxybenzyl)-3,6-dihydro-7H-[1,2,3]triazolo[4,5-d]pyrimidin-7-one (150 mg, 0.329 mmol, 1.0 equiv) and ethyl 3-oxo-2-(3-(4,4,5,5-tetramethyl-1,3,2-dioxaborolan-2-yl)benzyl)butanoate (228 mg, 0.657 mmol, 2.0 equiv) in dioxane (2.0 mL) and water (0.20 mL) was added $K_2CO_3$ (90.9 mg, 0.657 mmol, 2.0 equiv) and $Pd(dppf)Cl_2$-DCM (26.8 mg, 0.033 mmol, 0.10 equiv). After stirring for 2 h at 100° C. under nitrogen, the resulting mixture was concentrated under reduced pressure. The residue was purified by silica gel column chromatography, eluted with EA/PE (0-100%) to afford ethyl 2-((3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)methyl)-3-oxobutanoate (200 mg, crude) as an off-white solid.

Step 4: To a solution of hydroxylamine hydrochloride (39.7 mg, 0.571 mmol, 2.0 equiv) in MeOH (0.5 mL) heated to 60° C. was added a solution of NaOH (0.29 mL, 0.57 mmol, 2.0 equiv). The mixture was cooled to −50° C. To a solution of ethyl 2-((3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)methyl)-3-oxobutanoate (170 mg, 0.285 mmol, 1.0 equiv) in MeOH (1.5 mL) was added a solution of NaOH (0.14 mL, 0.285 mmol, 1.00 equiv) in water (0.5 mL). This mixture was cooled to −50° C., stirred for 10 min, and added to the above hydroxylamine solution. The reaction mixture was stirred at −50° C. for 2 h. The reaction mixture was then quickly added to 4 M HCl (2 mL) heated to 85° C. and stirred for 20 min at 85° C. The mixture was allowed to cool to room temperature. The precipitated solids were collected by filtration and washed with water (2×1 mL).

The resulting solid was dried under a heat lamp to afford 5-(3-ethoxy-3'-((3-hydroxy-5-methylisoxazol-4-yl)methyl)-[1,1'-biphenyl]-4-yl)-3-(4-methoxybenzyl)-3,6-dihydro-7H-[1,2,3]triazolo[4,5-d]pyrimidin-7-one (110 mg, 68.3%) as a yellow solid.

The above material was dissolved in trifluoroacetic acid (2.0 mL) was stirred for 3 h at 80° C. The mixture was allowed to cool to room temperature and the resulting mixture was concentrated under reduced pressure. The crude product was purified by preparative HPLC to afford 4-((3'-ethoxy-4'-(7-oxo-6,7-dihydro-3H-[1,2,3]triazolo[4,5-d]pyrimidin-5-yl)-[1,1'-biphenyl]-3-yl)methyl)-3-methylisoxazol-5(2H)-one (5.8 mg, 5.2%) as a white solid. LCMS (ESI)=445.2 $[M+H]^+$. $^1H$ NMR (300 MHz, DMSO-$d_6$) δ 12.17 (broad s, 1H), 7.87 (d, J=7.9 Hz, 1H), 7.62 (s, 1H), 7.62-7.57 (m, 1H), 7.45-7.35 (m, 2H), 7.38 (s, 1H), 7.26 (d, J=7.8 Hz, 1H), 4.30 (q, J=7.0 Hz, 2H), 3.56 (s, 2H), 2.11 (s, 3H), 1.40 (t, J=7.0 Hz, 3H).

Example 27: Synthesis of 5-(3-Ethoxy-3'-(2,2,2-trifluoro-1,1-dihydroxyethyl)-[1,1'-biphenyl]-4-yl)-3,6-dihydro-7H-[1,2,3]triazolo[4,5-d]pyrimidin-7-one (Compound 127)

127

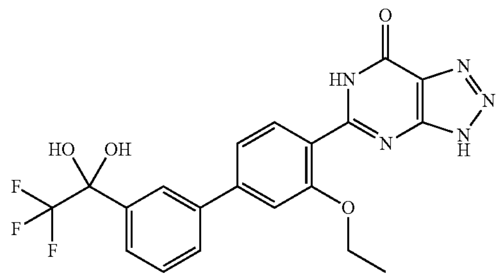

5-(3-Ethoxy-3'-(2,2,2-trifluoro-1,1-dihydroxyethyl)-[1,1'-biphenyl]-4-yl)-3,6-dihydro-7H-[1,2,3]triazolo[4,5-d]pyrimidin-7-one was prepared using the procedures in Example 4 from 1-(3-bromophenyl)-2,2,2-trifluoroethan-1-one. LCMS (ESI)=446.1 $[M-H]^-$. $^1H$ NMR (300 MHz, DMSO-$d_6$+$D_2O$ exchange) δ 7.99 (d, J=8.4 Hz, 1H), 7.93 (s, 1H), 7.83 (dt, J=7.8, 1.5 Hz, 1H), 7.67 (d, J=6.8 Hz, 3H), 7.56 (t, J=7.7 Hz, 1H), 7.40-7.33 (m, 2H), 4.31 (q, J=6.8 Hz, 2H), 1.42 (t, J=6.9 Hz, 3H).

Example 28: Synthesis of 5-(3-Ethoxy-4'-(2,2,2-trifluoro-1,1-dihydroxyethyl)-[1,1'-biphenyl]-4-yl)-3,6-dihydro-7H-[1,2,3]triazolo[4,5-d]pyrimidin-7-one (Compound 128)

128

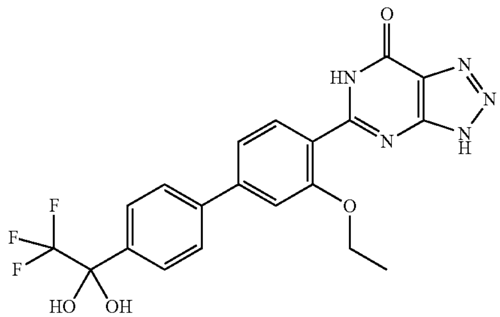

5-(3-Ethoxy-4'-(2,2,2-trifluoro-1,1-dihydroxyethyl)-[1,1'-biphenyl]-4-yl)-3,6-dihydro-7H-[1,2,3]triazolo[4,5-d]pyrimidin-7-one was prepared using the procedures in Example 4 from 1-(4-bromophenyl)-2,2,2-trifluoroethan-1-one. LCMS (ESI)=446.1 $[M-H]^-$. $^1H$ NMR (300 MHz, DMSO-$d_6$+D20 exchange) δ 7.93 (d, J=8.5 Hz, 1H), 7.83 (d, J=8.4 Hz, 2H), 7.72 (d, J=8.4 Hz, 2H), 7.46-7.41 (m, 2H), 4.31 (q, J=6.9 Hz, 2H), 1.40 (t, J=6.9 Hz, 3H).

Example 29: Beta-Arrestin Assay

Human GPR35 expressing JumpIn (Thermo Fisher) 294S Tango U2OS cells were plated in 384-well format in clear bottom plates at a cell density of 10,000 cells/well and allowed to adhere for 5 hours. Cells were then treated with serially diluted test compounds overnight. The next day, LiveBLAzer-FRET B/G (CCF4-AM) detection reagents were added, and cells were allowed to incubate for 4 hours in the dark at room temp before reading plates on a BioTek Cytation 5 plate reader. To determine EC50 values, data were fit to a four-parameter dose-response curves. EC50 values are shown in Table 1.

TABLE 1

| Compound | $EC_{50}$ |
|---|---|
| 101 | A |
| 102 | A |
| 103 | B |
| 104 | A |
| 105 | A |
| 106 | B |
| 107 | B |
| 108 | A |
| 109 | A |
| 110 | B |
| 111 | A |
| 112 | A |
| 113 | A |
| 114 | A |
| 115 | B |
| 116 | A |
| 117 | B |

TABLE 1-continued

| Compound | $EC_{50}$ |
|---|---|
| 118 | B |
| 119 | B |
| 120 | A |
| 121 | A |
| 122 | A |
| 123 | A |
| 124 | A |
| 125 | A |
| 126 | A |
| 127 | A |
| 128 | A |

A: $EC_{50}$ of less than or equal to 1 μM;
B: $EC_{50}$ of greater than 1 μM and less than or equal to 10 μM.

Example 30: Phase I/II Clinical Trial for Mild to Moderate Ulcerative Colitis

A double blind, randomized, placebo controlled, clinical study to evaluate the safety, tolerability and pilot therapeutic activity of Compound Formula (I) (hereinafter, "Compound"), was performed. Subjects with mild to moderate Ulcerative Colitis are administered the Compound as capsules by mouth, for 6 weeks.

Eligible subjects will be randomly assigned to either Compound or placebo, respectively. Sigmoidoscopies with biopsies will be performed at the first treatment visit and week 6. Subjects are treated for 12 weeks, with clinical evaluation on weeks 2, 4, 6 and between weeks 10-12.

Inclusion Criteria

1. Subject has a documented diagnosis of mild to moderate ulcerative colitis, as demonstrated clinically and by endoscopy at Visit 2.
2. Baron score greater than or equal to 2 at baseline.
3. Truelove-Witt (modified) score of 14 or less.
4. At least 6 months duration of disease
5. At baseline the subject should have either stable disease or stable disease requiring 5-ASA treatment
6. If on a 5-ASA treatment, subject must have been on stable dose for at least two weeks prior to screening and is expected to continue on that dose until the study is completed
7. Subject has normally functioning major organ systems (aside from gastrointestinal tract) as indicated by medical history, vital signs, physical exam and clinical laboratories (including hematology, coagulation, chemistries and urinalysis).
8. Male or female subjects 18-70 years old
9. Subject has provided voluntary written informed consent to participate in this study.
10. Subject may be of child-bearing potential, but is not pregnant, nursing, or planning a pregnancy for the duration of the study and has a negative pregnancy test prior to enrollment.
11. Subject agrees to use a medically-acceptable form of contraception from screening through 30 days after the final dose of study drug. Female partners of male subjects enrolled into this study are also recommended to use an acceptable method of birth control. Males must agree to not donate sperm during the entire study and for 90 days after the last dose of study drug.

Exclusion Criteria

1. A clinically significant medical history, medical finding or an ongoing medical or psychiatric condition which, in the opinion of the Investigator, could jeopardize the safety of the subject, impact the validity of the study results, or interfere with the completion of treatment according to this protocol.

2. Subject has an ALT or serum creatinine greater than 1.5 times the upper limit of normal range for the reference lab at screening.
3. Subject who, in the opinion of the investigator, is febrile at screening.
4. Subject had used the following treatments for IBD: steroids or any or biologic immunomodulators or any topical treatments (e.g. enemas) within the last 4 weeks prior to baseline, immunosuppressants or antimetabolites within the preceding 6 weeks, antibiotic use within the previous 7 days or chronic use of any anti-inflammatory drugs (except aminosalicylates) within 7 days.
5. History of illicit drug abuse or positive urine screen for drugs of abuse or history of alcohol abuse if acknowledged at the screening visit or noted in the subject's medical record at screening.
6. Subject has a positive blood screen for HIV, Hepatitis B (HBsAg), or Hepatitis C. 7. Subject has evidence of infectious colitis, e.g., *Clostridium difficile*, Amoebiasis, *Giardia lamblia* by stool examination of at screening.
8. Subject has evidence for gastrointestinal parasites as per stool ova and parasites testing at screening.
9. Subject has evidence of tuberculosis by blood interferon gamma release assay at screening.
10. Any uncontrolled, intercurrent illness (e.g., active infection).
11. History of gastrointestinal cancer.
12. Abdominal surgery or any major surgery within the preceding 28 days of the screening visit.

Primary Outcome Measure

The safety and tolerability of Compound in subjects with ulcerative colitis as demonstrated by the frequency and severity of adverse events [Time Frame: 6 Week].

Secondary Outcome Measure

1. Change in the modified Baron Score from Baseline to Week 6 [Time Frame: 6 Week]
2. Change in the Ulcerative Colitis Clinical Score from Baseline [Time Frame: 6 Week]
3. Change in the partial Mayo Score from baseline [Time Frame: 6 week]
4. Calprotectin concentrations [Time Frame: 6 week]
5. Riley Acute Inflammation Scale (histology) [Time Frame: 6 week]
6. Clinical remission [Time Frame: Week 6]

Example 31: Treating a Subject with Ulcerative Colitis

A subject diagnosed with mild to moderate ulcerative colitis (UC), as demonstrated clinically and by endoscopy at visit 2, is treated with a compound of Formula (I) (hereinafter, "Compound"). The Compound is administered to the subject intravenously or orally at least once, but in some cases, multiple times per week. After a period of time (e.g., six weeks) the subject may show reduced symptoms associated with UC, including rectal bleeding, bloody diarrhea, abdominal cramps, or pain. Additionally, the subject may show a reduced modified Baron Score, Ulcerative Colitis Clinical Score, partial Mayo Score (endoscopic), or Rily Acute Inflammation Scale (histology). In some cases, the subject shows clinical remission. In some cases, biomarkers such as Calprotectin concentrations are reduced, as measured in a fecal sample collected from the subject following treatment as compared to baseline (collected prior to treatment).

The examples and embodiments described herein are for illustrative purposes only and in some embodiments, various modifications or changes are to be included within the purview of disclosure and scope of the appended claims.

What is claimed is:

1. A compound having the structure of Formula (I):

Formula (I)

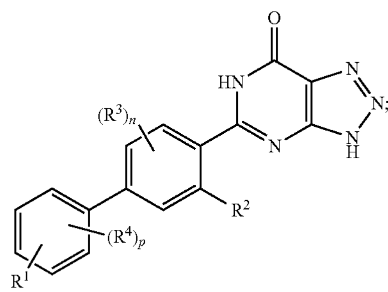

wherein:

$R^1$ is —$C_{1-6}$alkyl-C(O)N($R^{10}$)$_2$, —$C_{1-6}$alkyl-C(O)N(H)(OH), —$C_{1-6}$alkyl-C(O)N(H)($OCH_3$), —$C_{1-6}$alkyl-C(O)N(H)S(O)$_2$N($R^{10}$)$_2$, —O—$C_{1-6}$alkyl-C(O)N($R^{10}$)$_2$, —O—$C_{1-6}$alkyl-C(O)N(H)(OH), —O—$C_{1-6}$alkyl-C(O)N(H)($OCH_3$), —O—$C_{1-6}$alkyl-C(O)N(H)S(O)$_2$N($R^{10}$)$_2$, —C(H)═$R^5$, —$C_{1-6}$alkyl-$R^5$, or —$C_{1-6}$alkyl-$C_{2-9}$heteroaryl, wherein —$C_{1-6}$alkyl-$C_{2-9}$heteroaryl is optionally substituted on the heteroaryl with one, two, or three groups independently selected from halogen, $C_{1-6}$alkyl, $C_{1-6}$haloalkyl, and —C(O)O$R^{10}$;

$R^2$ is H, —OH, —N($R^{10}$)$_2$, —O—$C_{1-6}$alkyl, —$C_{1-6}$alkyl-OH, —$C_{1-6}$alkyl-O$R^9$, —$C_{1-6}$alkyl-N($R^{10}$)$_2$, $C_{1-6}$haloalkyl;

each $R^3$ is independently selected from halogen, —CN, —OH, —O$R^9$, —S$R^9$, —N($R^{10}$)$_2$, —$NO_2$, —S(O)$R^9$, —S(O)$_2R^9$, —NHS(O)$_2R^9$, —S(O)$_2$N($R^{10}$)$_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each $R^4$ is independently selected from halogen, —CN, —OH, —O$R^9$, —S$R^9$, —N($R^{10}$)$_2$, —S(O)$R^9$, —S(O)$_2R^9$, —NHS(O)$_2R^9$, —S(O)$_2$N($R^{10}$)$_2$, —C(O)NHS(O)$_2$N($R^{10}$)$_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-$R^9$, —$C_{1-6}$alkyl-OH, —$C_{1-6}$alkyl-O$R^9$, —$C_{1-6}$alkyl-N($R^{10}$)$_2$, —$C_{1-6}$alkyl-C(O)O$R^{10}$, $C_{2-6}$alkenyl, —$C_{2-6}$alkenyl-C(O)O$R^{10}$, $C_{2-6}$alkynyl, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, and $C_{1-9}$heteroaryl; wherein $C_{3-8}$cycloalkyl, —$C_{1-6}$ alkyl-$C_{3-8}$cycloalkyl, phenyl, —$C_{1-6}$alkyl-phenyl, and $C_{1-9}$heteroaryl are optionally substituted on the ring structure with one, two, or three groups independently selected from halogen, —C(O)OR$^{10}$, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl and —$C_{1-6}$alkyl-$C_{2-9}$heterocycloalkyl are optionally substituted on the ring structure with one, two, or three groups independently selected from halogen, —C(O)OR$^{10}$, $C_{1-6}$alkyl, $C_{1-6}$haloalkyl, and oxo;

$R^5$ is $C_{2-9}$heterocycloalkyl optionally substituted on the heterocycloalkyl with one, two, or three groups independently selected from halogen, $C_{1-6}$alkyl, $C_{1-6}$haloalkyl, —C(O)OR$^{10}$, and oxo;

each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted on the ring structure with one or two groups independently selected from $C_{1-6}$alkyl, —OR$^{11}$, —N(R$^{11}$)$_2$, $C_{1-6}$alkyl, $C_{3-8}$cycloalkyl, —N(R$^{11}$)C(O)R$^{12}$, —C(O)R$^{12}$, and —C(O)OR$^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted on the ring stucture with one or two groups independently selected from halogen, $C_{1-6}$alkyl, —N(R$^{11}$)$_2$, and —C(O)OR$^{12}$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each $R^{11}$ is independently selected from H and $C_{1-6}$alkyl;

each $R^{12}$ is independently selected from H and $C_{1-6}$alkyl;

n is 0, 1, 2, or 3; and p is 0, 1, 2, 3, or 4;

or a pharmaceutically acceptable salt or solvate thereof.

2. The compound of claim 1, or a pharmaceutically acceptable salt or solvate thereof, wherein $R^1$ is —$C_{1-6}$alkyl-$R^5$.

3. The compound of any one of claims 1, or a pharmaceutically acceptable salt or solvate thereof, wherein $R^5$ is $C_{2-9}$heterocycloalkyl substituted on the heterocycloalkyl with one, two, or three groups independently selected from $C_{1-6}$alkyl and oxo.

4. The compound of any one of claims 1, or a pharmaceutically acceptable salt or solvate thereof, wherein $R^5$ is $C_{2-9}$heterocycloalkyl substituted on the heteroalkyl with one, two, or three groups independently selected from $C_{1-6}$alkyl, $C_{1-6}$haloalkyl, and oxo.

5. The compound of claim 1, or a pharmaceutically acceptable salt or solvate thereof, wherein $R^1$ is

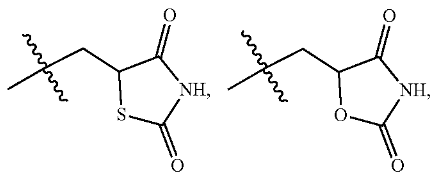

-continued

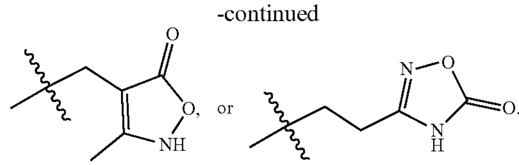

6. The compound of claim 1, or a pharmaceutically acceptable salt or solvate thereof, wherein $R^1$ is

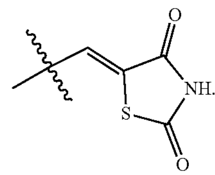 [SMILES: */C=C1\SC(=O)NC1=O]

7. The compound of claim 1, or a pharmaceutically acceptable salt or solvate thereof, wherein $R^1$ is —$C_{1-6}$alkyl-C(O)N(H)S(O)$_2$N(R$^{10}$)$_2$, or —CH$_2$CH$_2$—C(O)N(H)S(O)$_2$N(CH$_3$)$_2$.

8. The compound of claim 1, or a pharmaceutically acceptable salt or solvate thereof, wherein $R^1$ is —$C_{1-6}$alkyl-$C_{2-9}$heteroaryl optionally substituted with one, two, or three groups independently selected from halogen, $C_{1-6}$alkyl, $C_{1-6}$haloalkyl, and —C(O)OR$^{10}$.

9. The compound of any one of claims 1, or a pharmaceutically acceptable salt or solvate thereof, wherein each $R^4$ is independently selected from halogen, —OH, —OR$^9$, —N(R$^{10}$)$_2$, —C(O)OR$^{10}$, —C(O)N(R$^{10}$)$_2$, $C_{1-6}$alkyl, —$C_{1-6}$alkyl-OH, —$C_{1-6}$alkyl-OR$^9$, —$C_{1-6}$alkyl-N(R$^{10}$)$_2$, —$C_{1-6}$alkyl-C(O)OR$^{10}$, and $C_{1-9}$heteroaryl.

10. The compound of any one of claims 1, or a pharmaceutically acceptable salt or solvate thereof, wherein each $R^4$ is independently selected from halogen, —OH, —OR$^9$, $C_{1-6}$alkyl, and —$C_{1-6}$alkyl-OH.

11. The compound of any one of claims 1, or a pharmaceutically acceptable salt or solvate thereof, wherein p is 0, 1, or 2.

12. The compound of any one of claims 1, or a pharmaceutically acceptable salt or solvate thereof, wherein $R^2$ is H, —OH, —N(R$^{10}$)$_2$, or —O—$C_{1-6}$alkyl.

13. The compound of any one of claims 1, or a pharmaceutically acceptable salt or solvate thereof, wherein $R^2$ is —O—$C_{1-6}$alkyl.

14. The compound of any one of claims 1, or a pharmaceutically acceptable salt or solvate thereof, wherein $R^2$ is —OCH$_2$CH$_3$.

15. The compound of any one of claims 1, or a pharmaceutically acceptable salt or solvate thereof, wherein n is 0.

16. A compound selected from:

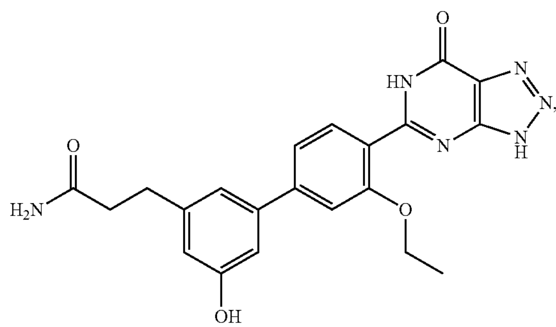

-continued
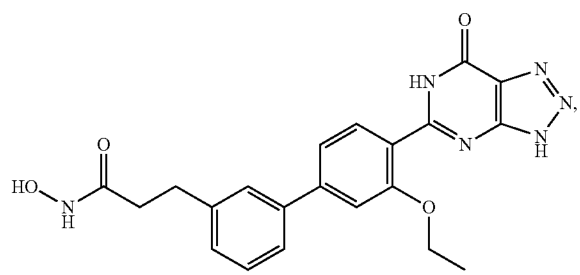
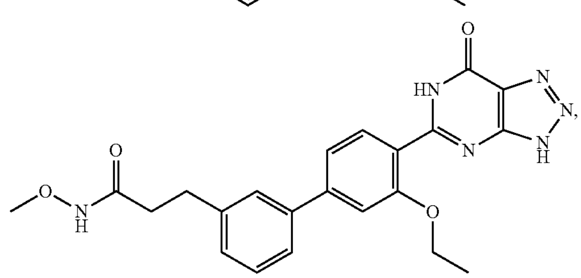
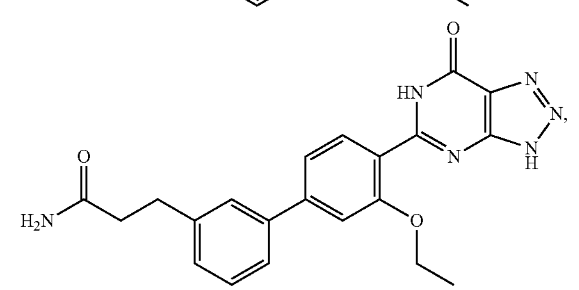
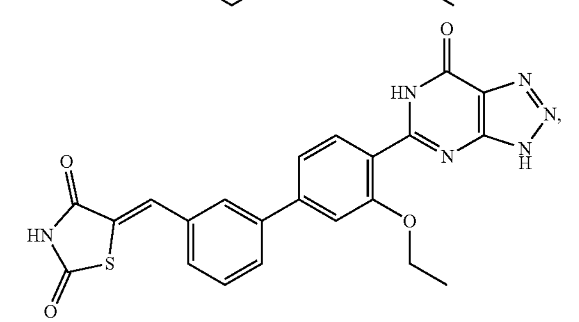
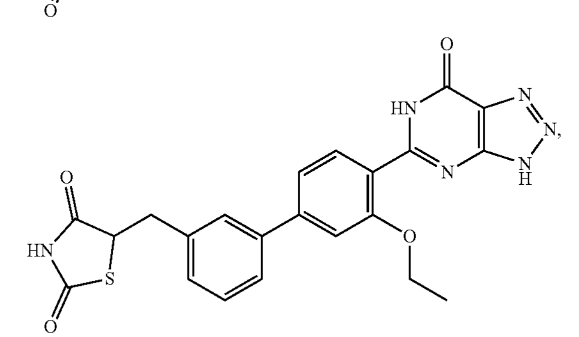
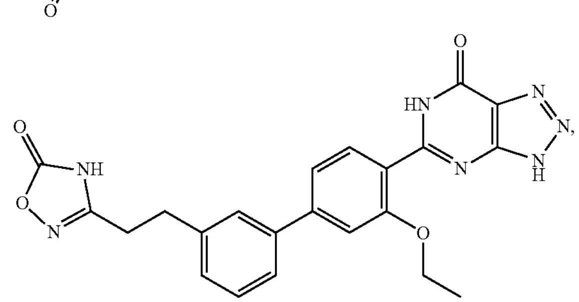
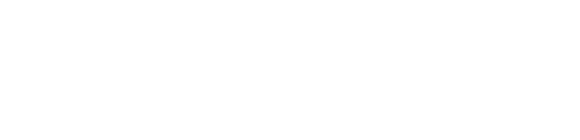
-continued
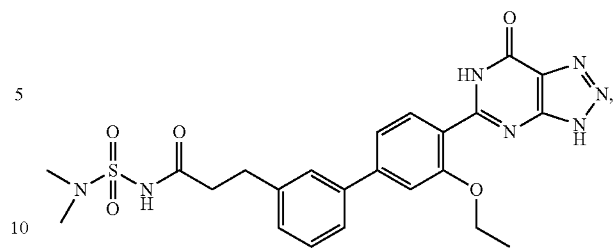
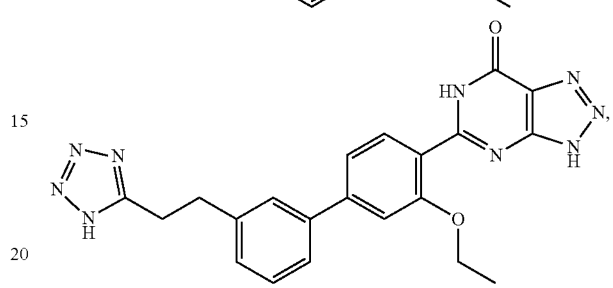
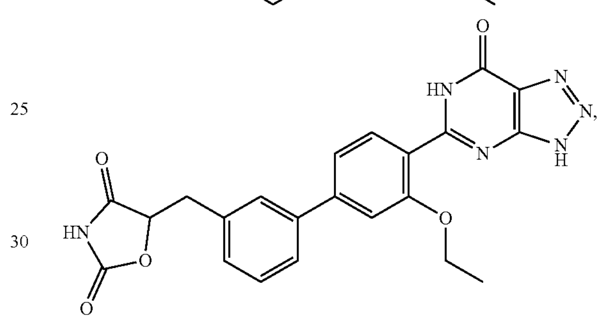
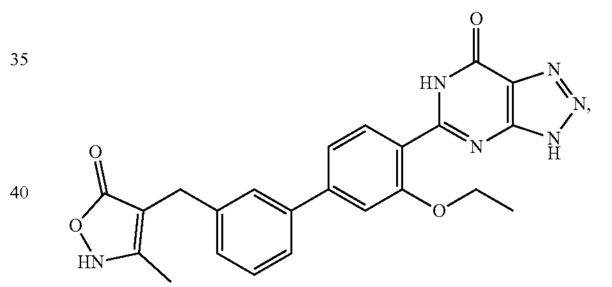
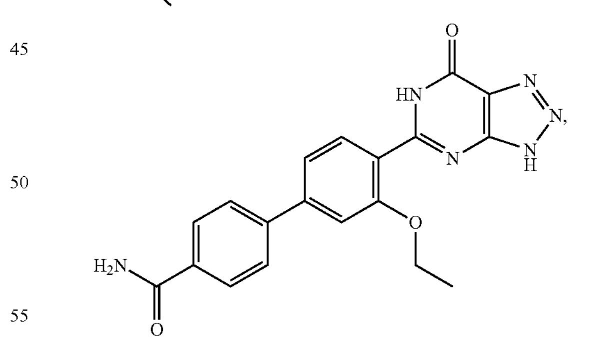
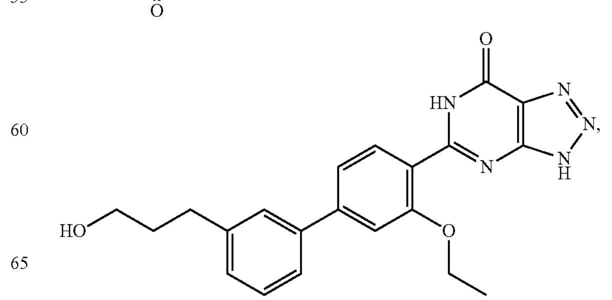
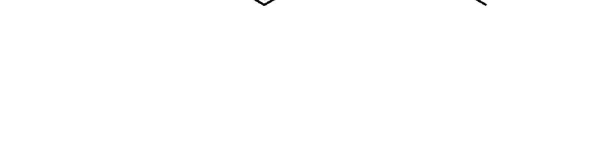

-continued
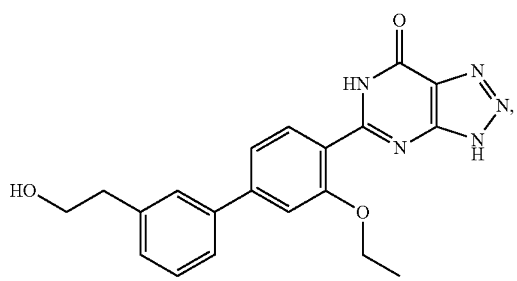
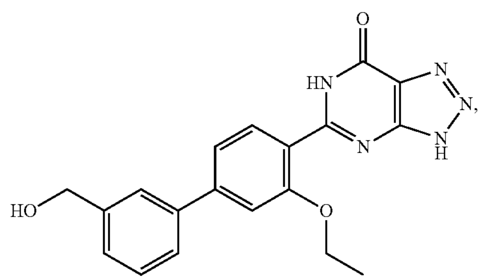
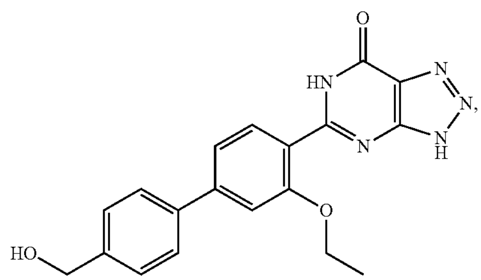
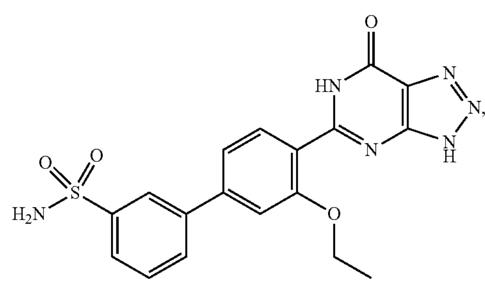
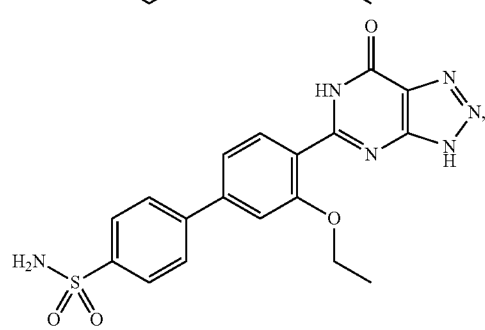
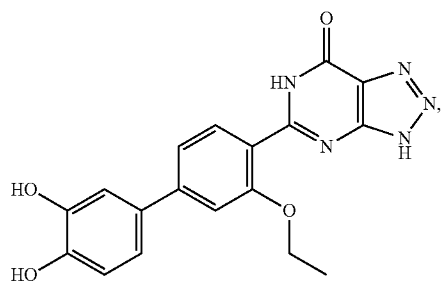
-continued
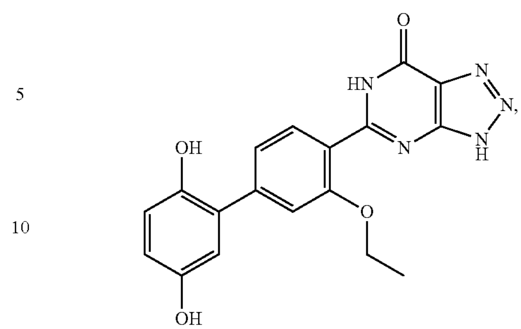
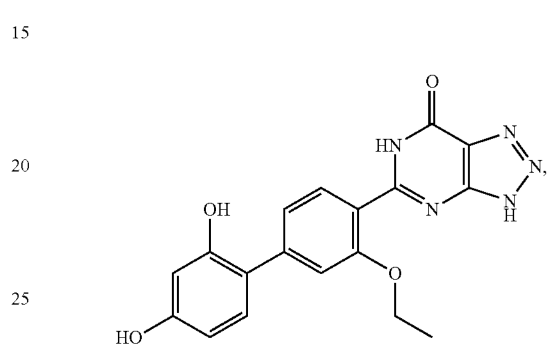
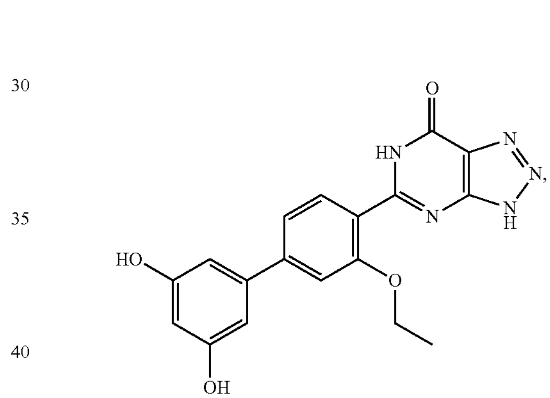
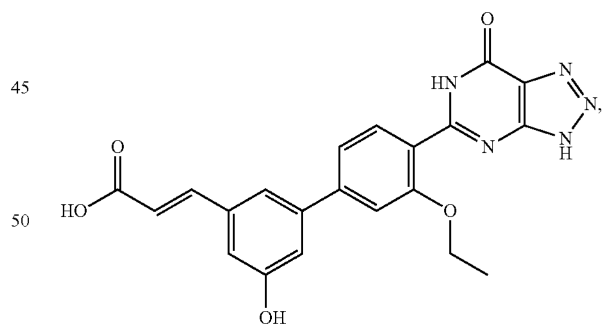
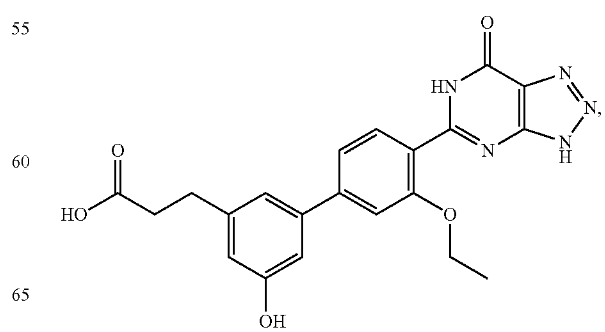

-continued

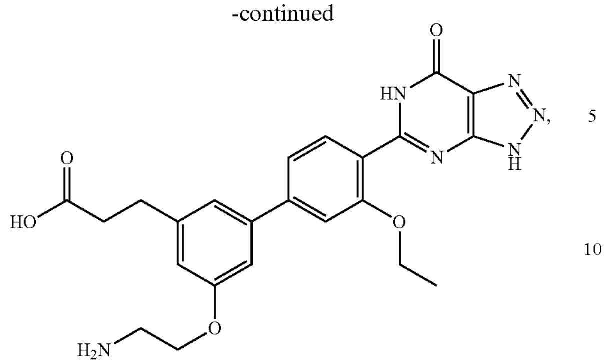

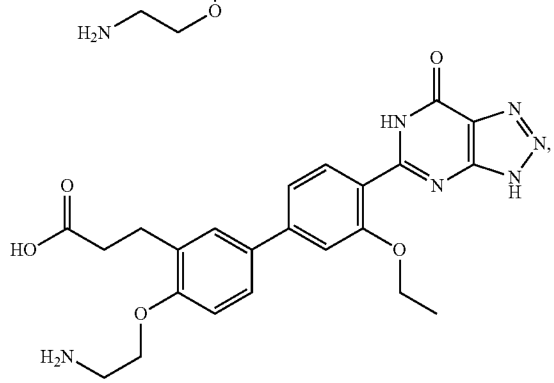

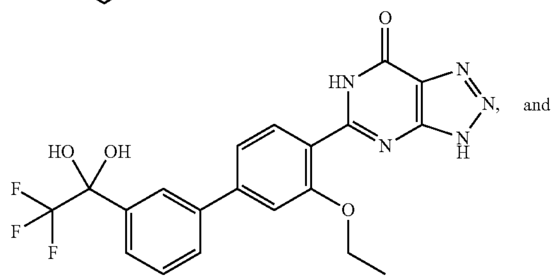

and

-continued

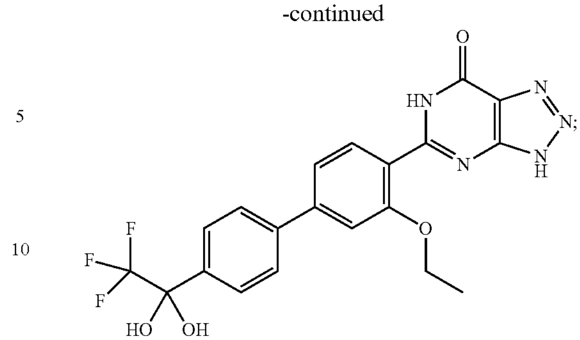

or a pharmaceutically acceptable salt or solvate thereof.

17. A pharmaceutical composition comprising a compound of any one of claims 1, or a pharmaceutically acceptable salt or solvate thereof, and a pharmaceutically acceptable excipient.

18. A method of treating an inflammatory bowel disease in a patient in need thereof, comprising administering to the patient a therapeutically effective amount of a compound of any one of claims 1, or a pharmaceutically acceptable salt or solvate thereof.

19. The method of claim 18, wherein the inflammatory bowel disease is selected from Crohn's disease, ulcerative colitis, and perianal Crohn's disease.

20. A method of modulating GPR35 activity comprising contacting GPR35, or portion thereof, with a compound of any one of claims 1, or a pharmaceutically acceptable salt or solvate thereof.

* * * * *